United States Patent
Wang et al.

(10) Patent No.: US 10,988,458 B2
(45) Date of Patent: *Apr. 27, 2021

(54) APOPTOSIS SIGNAL-REGULATING KINASE 1 INHIBITORS AND METHODS OF USE THEREOF

(71) Applicant: Enanta Pharmaceuticals, Inc., Watertown, MA (US)

(72) Inventors: Guoqiang Wang, Belmont, MA (US); Ruichao Shen, Belmont, MA (US); Jiang Long, Wayland, MA (US); Jun Ma, Belmont, MA (US); Xuechao Xing, Wilmington, MA (US); Yong He, Lexington, MA (US); Brett Granger, Sudbury, MA (US); Jing He, Somerville, MA (US); Bin Wang, Newton, MA (US); Yat Sun Or, Waltham, MA (US)

(73) Assignee: Enanta Pharmaceuticals, Inc., Watertown, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/866,778

(22) Filed: May 5, 2020

(65) Prior Publication Data

US 2020/0331890 A1 Oct. 22, 2020

Related U.S. Application Data

(63) Continuation of application No. 15/979,128, filed on May 14, 2018, now Pat. No. 10,683,279.

(60) Provisional application No. 62/505,202, filed on May 12, 2017, provisional application No. 62/523,472, filed on Jun. 22, 2017, provisional application No. 62/550,960, filed on Aug. 28, 2017.

(51) Int. Cl.
| | |
|---|---|
| *C07D 401/14* | (2006.01) |
| *C07D 405/14* | (2006.01) |
| *C07D 403/14* | (2006.01) |
| *C07D 413/14* | (2006.01) |
| *C07D 417/14* | (2006.01) |
| *C07D 403/12* | (2006.01) |

(52) U.S. Cl.
CPC ........ *C07D 401/14* (2013.01); *C07D 403/12* (2013.01); *C07D 403/14* (2013.01); *C07D 405/14* (2013.01); *C07D 413/14* (2013.01); *C07D 417/14* (2013.01)

(58) Field of Classification Search
CPC .. C07D 401/14; C07D 405/14; C07D 403/14; C07D 413/14; C07D 417/14
See application file for complete search history.

(56) References Cited

U.S. PATENT DOCUMENTS

| | | | |
|---|---|---|---|
| 6,140,347 A | 10/2000 | Castro et al. | |
| 6,534,651 B2 | 3/2003 | Jagtap et al. | |
| 7,678,792 B2 | 3/2010 | Chianelli et al. | |
| 8,378,108 B2 | 2/2013 | Corkey et al. | |
| 8,653,075 B2 | 2/2014 | Grundl et al. | |
| 8,895,745 B2 | 11/2014 | Berdini et al. | |
| 9,067,933 B2 | 6/2015 | Corkey et al. | |
| 9,132,140 B2 | 9/2015 | Reddy et al. | |
| 9,254,284 B2 | 2/2016 | Notte | |

(Continued)

FOREIGN PATENT DOCUMENTS

| | | |
|---|---|---|
| CN | 107793400 A | 3/2018 |
| WO | 2004018428 A1 | 3/2004 |

(Continued)

OTHER PUBLICATIONS

Wermuth, C.G. "Molecular Variations Based on Isosteric Replacements" in "The Practice of Medicinal Chemistry" 1996, Academic Press Limited, pp. 203-237 (Year: 1996).*

(Continued)

*Primary Examiner* — Matthew P Coughlin
(74) *Attorney, Agent, or Firm* — Edgar W. Harlan; Carolyn S. Elmore; Elmore Patent Law Group, P.C.

(57) ABSTRACT

The present invention discloses compounds of Formula (I), or pharmaceutically acceptable salts, ester, stereoisomer, tautomer, solvate, hydrate, or combination thereof:

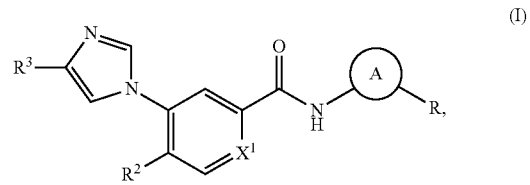

which inhibit the Apoptosis signal-regulating kinase 1 (ASK-1), which associated with autoimmune disorders, neurodegenerative disorders, inflammatory diseases, chronic kidney disease, cardiovascular disease. The present invention further relates to pharmaceutical compositions comprising the aforementioned compounds for administration to a subject suffering from ASK-1 related disease. The invention also relates to methods of treating an ASK-1 related disease in a subject by administering a pharmaceutical composition comprising the compounds of the present invention. The present invention specifically relates to methods of treating ASK-1 associated with hepatic steatosis, including non-alcoholic fatty liver disease (NAFLD) and non-alcohol steatohepatitis disease (NASH).

23 Claims, No Drawings

(56) References Cited

U.S. PATENT DOCUMENTS

| | | |
|---|---|---|
| 9,751,885 B2 | 9/2017 | Tomita et al. |
| 10,246,439 B2 | 4/2019 | Granger et al. |
| 10,253,018 B2 | 4/2019 | Wang et al. |
| 10,450,301 B2 | 10/2019 | Granger et al. |
| 10,597,382 B2 | 3/2020 | Wang et al. |
| 10,683,279 B2 * | 6/2020 | Wang .................. A61P 9/00 |
| 10,683,289 B2 | 6/2020 | Granger et al. |
| 2005/0113450 A1 | 5/2005 | Thorarensen et al. |
| 2009/0318425 A1 | 12/2009 | Chang et al. |
| 2010/0029619 A1 | 2/2010 | Uchikawa et al. |
| 2011/0009410 A1 * | 1/2011 | Corkey .................. A61P 3/10 514/236.2 |
| 2012/0004267 A1 * | 1/2012 | Corkey ................ A61P 11/08 514/333 |
| 2013/0203731 A1 | 8/2013 | Chang et al. |
| 2013/0210810 A1 | 8/2013 | Singh et al. |
| 2014/0018370 A1 | 1/2014 | Corkey et al. |
| 2014/0249135 A1 | 9/2014 | Burger et al. |
| 2014/0329850 A1 | 11/2014 | Chang |
| 2015/0005280 A1 | 1/2015 | Sasmal et al. |
| 2017/0210748 A1 | 7/2017 | Witty et al. |
| 2018/0327388 A1 | 11/2018 | Wang et al. |
| 2018/0362501 A1 | 12/2018 | Wang et al. |
| 2018/0362502 A1 | 12/2018 | Granger et al. |
| 2018/0362503 A1 | 12/2018 | Granger et al. |
| 2019/0062310 A1 | 2/2019 | Wang et al. |
| 2019/0337923 A1 | 11/2019 | Wang et al. |
| 2019/0337935 A1 | 11/2019 | Granger et al. |
| 2020/0062727 A1 | 2/2020 | He et al. |
| 2020/0157095 A1 | 5/2020 | Granger et al. |
| 2020/0308193 A1 | 10/2020 | Granger et al. |

FOREIGN PATENT DOCUMENTS

| | | | |
|---|---|---|---|
| WO | 2005009470 A1 | 2/2005 | |
| WO | 2005103288 A1 | 11/2005 | |
| WO | 2007000339 A1 | 1/2007 | |
| WO | 2008082579 A1 | 7/2008 | |
| WO | 2009011850 A2 | 1/2009 | |
| WO | 2009027283 A1 | 3/2009 | |
| WO | 2009123986 A1 | 10/2009 | |
| WO | 2010008843 A1 | 1/2010 | |
| WO | 2011008709 A1 | 1/2011 | |
| WO | 2011041293 A1 | 4/2011 | |
| WO | 2011097079 A1 | 8/2011 | |
| WO | 2012003387 A1 | 1/2012 | |
| WO | 2012011548 A1 | 1/2012 | |
| WO | 2012080735 A1 | 6/2012 | |
| WO | 2013112741 A1 | 8/2013 | |
| WO | 2014100541 A1 | 6/2014 | |
| WO | 2014106019 A2 | 7/2014 | |
| WO | 2014137728 A1 | 9/2014 | |
| WO | 2015095059 A1 | 6/2015 | |
| WO | 2015187499 A1 | 12/2015 | |
| WO | 2016049069 A1 | 3/2016 | |
| WO | 2016049070 A1 | 3/2016 | |
| WO | 2016105453 A1 | 6/2016 | |
| WO | 2016106384 A1 | 6/2016 | |
| WO | 2018090869 A1 | 5/2018 | |
| WO | 2018133856 A1 | 7/2018 | |
| WO | 2018133865 A1 | 7/2018 | |
| WO | 2018133866 A1 | 7/2018 | |
| WO | 2018148204 A1 | 8/2018 | |
| WO | 2018149284 A1 | 8/2018 | |
| WO | 2018151830 A1 | 8/2018 | |
| WO | WO-2018151830 A1 * | 8/2018 | ......... A61K 31/4439 |
| WO | 2018157277 A1 | 9/2018 | |
| WO | 2018157856 A1 | 9/2018 | |
| WO | 2018157857 A1 | 9/2018 | |
| WO | 2018160406 A1 | 9/2018 | |
| WO | 2018169742 A1 | 9/2018 | |
| WO | 2018183122 A1 | 10/2018 | |
| WO | 2018187506 A1 | 10/2018 | |
| WO | 2018218051 A1 | 11/2018 | |
| WO | 2018233553 A1 | 12/2018 | |
| WO | 2019034096 A1 | 2/2019 | |
| WO | 2019050794 A1 | 3/2019 | |
| WO | 2019051265 A1 | 3/2019 | |
| WO | 2019070742 A1 | 4/2019 | |

OTHER PUBLICATIONS

Pubmed Compound Summary for CID 53276841, '2-Methyl-1,1,3-trioxo-N-pyridin-2-yl-1,2-benzolhiazole-6-carboxamide', U.S. National library of Medicine, Aug. 1, 2011 (Aug. 1, 2011), p. 1-7; p. 2 (https://lpubchem.ncbi.nlm.nih.gov/compound/53276841).

Burger, A. et al., "Isosteric Compounds. I. Acyl Derivatives of Dibenzothiophene", J. Am. Chem. Soc., vol. 60, 11, 1938, 2628-2630.

Dudkin, V. Y., "Bioisosteric Equivalence of Five-Membered Heterocycles", Chemistry of Heterocyclic Compounds, vol. 48, No. 1, 2012, 27-32.

Gibson, et al., "Structure-based drug design of novel ASK1 inhibitors using an integrated lead optimization strategy", Bioorganic & Medicinal Chemistry Letters, 2017, 1-5.

Kawarazaki, et al., "Apoptosis signal-regulating kinase 1 as a therapeutic target", Expert Opinion on Therapeutic Targets, 18(6), 2014, 651-664.

Lanier, M. et al., "Structure-Based Design of ASK1 Inhibitors as Potential Agents for Heart Failure", ACS Medicinal Chemistry Letters, vol. 8, 2017, 316-320.

Loomba, et al., "The ASK1 Inhibitor Selonsertib in Patients with Nonalcoholic Steatohepatitis: A Randomized, Phase 2 Trial", Hepatology 67(2), 2018, 549-559.

Lovering, et al., "Rational approach to highly potent and selective apoptosis signal regulating kinase 1 (ASK1) inhibitors", European Journal of Medicinal Chemistry, 145, 2018, 606-621.

Monastyrsky, et al., "Discovery of 2-arylquinazoline derivatives as a new class of ASK1 inhibitors", Bioorganic & Medicinal Chemistry Letters, 28, 2018, 400-404.

Patani, George A. et al., "Bioisosterism: A Rational Approach in Drug Design", Chem. Rev., 96, 1996, 3147-3176.

Sheridan, Robert P., "The Most Common Chemical Replacements in Drug-Like Compounds", J. Chem. Info. Comput. Sci. 2002, vol. 42, 2002, 103-108.

Silverman, R. B., "The Organic Chemistry of Drug Design and Drug Action", Elsevier Academic Press, 2004, 29-32.

Starosyla, S. et al., "ASK1 Pharmacophore Model Derived from Diverse Classes of Inhibitors", Bioorganic & Medicinal Chemistry Letters, 24, 2014, 4418-4423.

Terao, et al., "Design and biological evaluation of imidazo[1,2-a]pyridines as novel and potent ASK1 inhibitors", Bioorganic & Medicinal Chemistry Letters, 22, 2012, 7326-7329.

Volynets, et al., "Identification of 3H-Naphtho[1,2,3-de]quinoline-2,7-diones as Inhibitors of Apoptosis Signal-Regulating Kinase 1 (ASK1)", Journal of Medicinal Chemistry, 54, 2011, 2680-2686.

Volynets, et al., "Rational design of apoptosis signal-regulating kinase 1 inhibitors: Discovering novel structural scaffold", European Journal of Medicinal Chemistry 61, 2013, 104-115.

Wermuth, C. G., "Molecular Variations Based on Isosteric Replacements", in "The Practice of Medicinal Chemistry", Academic Press Limited, 1996, 203-237.

Ali, et al., "Recent advances in the development of farnesoid X receptor agonists", Ann Transl Med, 3(1), 2015, 1-16.

Okamoto, M., "Identification of novel ASK1 inhibitors using virtual screening", Bioorganic & Medicinal Chemistry, vol. 19, 2011, 486-489.

Starosyla, S. et al., "Identification of apoptosis signal-regulating kinase 1 (ASK1) inhibitors among the derivatives of benzothiazol-2-yl-3-hydroxy-5-phenyl-1,5-dihydro-pyrrol-2-one", Bioorganic & Medicinal Chemistry, vol. 23., 2015, 2489-2497.

* cited by examiner

APOPTOSIS SIGNAL-REGULATING KINASE 1 INHIBITORS AND METHODS OF USE THEREOF

RELATED APPLICATIONS

This application is a continuation application of U.S. application Ser. No. 15/979,128, filed on May 14, 2018, which claims the benefit of U.S. Provisional Applications No. 62/505,202, filed on May 12, 2017, No. 62/523,472, filed on Jun. 22, 2017, and 62/550,960, filed on Aug. 28, 2017. The entire teachings of the above applications are incorporated herein by reference.

TECHNICAL FIELD

The present invention relates generally to compounds and pharmaceutical compositions useful as ASK-1 inhibitors. Specifically, the present invention relates to compounds useful as inhibitors of ASK-1 and methods for their preparation and use.

BACKGROUND OF THE INVENTION

Apoptosis signal-regulating kinase 1 (ASK-1) is a member of the mitogen-activated protein kinase kinase kinase (MAPKKK, MAP3K) family, which when activated phosphorylates downstream MAP kinase kinases (MAPKK, MAP2K), which in turn activate MAP kinases (MAPK). MAPKs elicit a response by phosphorylating cellular substrates, thus regulating the activity of transcription factors that ultimately control gene expression. Specifically ASK-1, also known as MAPKKK5, phosphorylates MAPKK4/MAPKK7 or MAPKK3/MAPKK6, which subsequently phosphorylates and activates the c-Jun N-terminal protein kinase (JNK) and p38 MAPKs, respectively (H. Ichijo, et al., *Cell Comm. Signal* 2009, 7, 1-10; K. Takeda, et al., *Annu. Rev. Pharmacol. Toxicol.* 2008, 48, 199-225; H. Nagai, et al., *J. Biochem. Mol. Biol.* 2007, 40, 1-6). Activation of the JNK and p38 pathways triggers a downstream stress response such as apoptosis, inflammation, or differentiation (H. Ichijo, et al., *Science* 1997, 275, 90-94; K. Takeda, et al., *J. Biol. Chem.* 2000, 275, 9805-9813; K. Tobiume, et al., *EMBO Rep.* 2001, 2, 222-228; K. Sayama et al., *J. Biol. Chem.* 2001, 276, 999-1004).

The activity of ASK-1 is regulated by thioredoxin (Trx), which binds to the N-terminal end of ASK-1 (M. Saitoh, et al., *EMBO J.* 1998, 17, 2596-2606). ASK-1 is activated succeeding autophosphorylation at Thr838 in response to environmental stimuli including oxidative stress, lipopolysaccharides (LPS), reactive oxygen species (ROS), endoplasmic reticulum (ER) stress, an increase in cellular calcium ion concentrations, Fas ligand, and various cytokines such as tumor necrosis factor (TNF) (H. Nishitoh, et al., *Genes Dev.* 2002, 16, 1345-1355; K. Takeda, et al., *EMBO Rep.* 2004, 5, 161-166; A. Matsuzawa, et al., *Nat. Immunol.* 2005, 6, 587-592).

ASK-1 has been associated with autoimmune disorders, neurodegenerative disorders, inflammatory diseases, chronic kidney disease, cardiovascular disease, metabolic disorders, and acute and chronic liver diseases (R. Hayakawa, et al., *Proc. Jpn. Acad, Ser. B* 2012, 88, 434-453).

More specifically, ASK-1 has been associated with hepatic steatosis, including non-alcoholic fatty liver disease (NAFLD) and non-alcohol steatohepatitis (NASH). In a mouse model, high fat diets have caused induction of hepatic steatosis, ultimately causing fat accumulation and fatty acid oxidation. This led to the generation of ROS which caused hepatocyte dysfunction and death (S. K. Mantena, et al., *Free Radic. Biol. Med* 2008, 44, 1259-1272; S. K. Mantena, et al., *Biochem. J.* 2009, 417, 183-193). Moreover, TNF was shown to be critical for apoptosis of hepatocytes through the ASK-1-JNK pathway, and TNF deficient mice showed reduced hepatic steatosis and fibrosis (W. Zhang, et al., *Biochem. Biophys. Res. Commun.* 2010, 391, 1731-1736).

Small molecule compounds which act as ASK-1 inhibitors have been disclosed in the following publications: WO 2008/016131, WO 2009/027283, WO 2009/0318425, WO 2009/123986, US 2009/0318425, WO 2011/041293, WO 2011/097079, US 2011/0009410, G. P. Volynets, et al., *J. Med Chem.* 2011, 54, 2680-2686, WO 2012/003387, WO 2012/011548, WO 2012/080735, Y. Terao, et al., *Bioorg. Med Chem. Lett.* 2012, 22, 7326-7329, WO 2013/112741, G. P. Volynets, et al., *Eur. J. Med Chem.* 2013, 16, 104-115, US 2014/0018370, WO 2014/100541, WO 2015/095059, WO 2016/049069, WO 2016/049070.

There is a need for the development of ASK-1 inhibitors for the treatment and prevention of disease. The present invention has identified compounds which inhibit ASK-1 as well as methods of using these compounds to treat disease.

SUMMARY OF THE INVENTION

The present invention relates to compounds and pharmaceutical compositions useful as ASK-1 inhibitors. Specifically, the present invention relates to compounds useful as inhibitors of ASK-1 and methods for their preparation and use. In addition, the present invention includes the process for the preparation of the said compounds.

In its principal aspect, the present invention provides a compound of Formula (I), or a pharmaceutically acceptable salt or ester thereof:

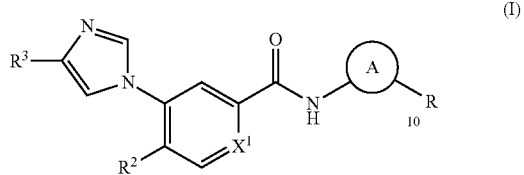

(I)

wherein:

is selected from

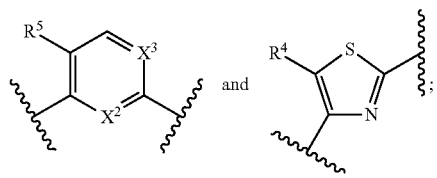

$X^1$, $X^2$ and $X^3$ are each independently selected from N and $C(R^5)$;

$R^3$, $R^4$ and $R^5$ are each independently selected from the group consisting of:

1) Hydrogen;
2) Halogen;
3) —NO$_2$;
4) Cyano;
5) Optionally substituted —C$_1$-C$_8$ alkyl;
6) Optionally substituted —C$_3$-C$_8$ cycloalkyl;
7) Optionally substituted 3- to 8-membered heterocycloalkyl; and
8) Optionally substituted —C$_1$-C$_8$ alkoxy;

R is selected from the groups:

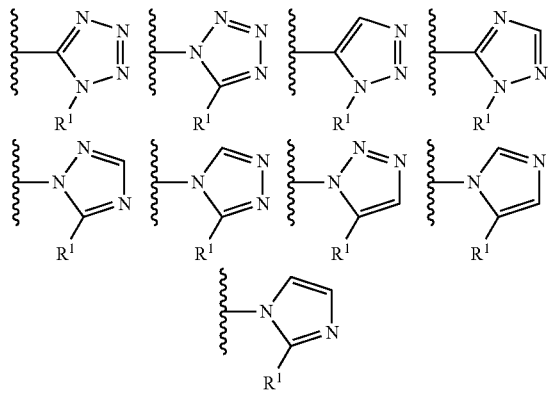

wherein each triazole or imidazole ring is optionally further substituted;

R$^1$ is selected from the group consisting of:
1) Hydrogen;
2) Optionally substituted —C$_1$-C$_8$ alkyl;
3) Optionally substituted —C$_2$-C$_8$ alkenyl;
4) Optionally substituted —C$_2$-C$_8$ alkynyl;
5) Optionally substituted —C$_3$-C$_8$ cycloalkyl;
6) Optionally substituted aryl;
7) Optionally substituted arylalkyl;
8) Optionally substituted 3- to 8-membered heterocycloalkyl;
9) Optionally substituted heteroaryl;
10) Optionally substituted heteroarylalkyl; and
11) —N(R$^6$)(R$^7$), wherein R$^6$ and R$^7$ are independently selected from the group consisting of hydrogen, —C$_1$-C$_{15}$ alkyl, preferably C$_1$-C$_8$-alkyl; cycloalkyl, heterocycloalkyl, aryl, and heteroaryl, wherein each alkyl, cycloalkyl, heterocycloalkyl, aryl and heteroaryl is optionally substituted with 1-3 substituents independently selected from halo, alkyl, alkylamino, dialkylamino, alkylC(O)NH—, aryC(O)NH—, heteroarylC(O)—NH, —CN, alkoxy, —CF$_3$, aryl, and heteroaryl, alternatively, R$^7$ and R$^8$ are taken together with the nitrogen atom to which they are attached to form a heterocyclic;

provided that when R is

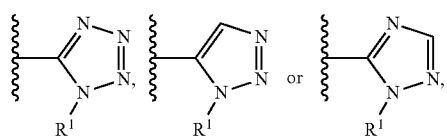

R$^1$ is not —N(R$^6$)(R$^7$);
R$^2$ is selected from the group consisting of:

1) Hydrogen;
2) Halogen;
3) —NO$_2$;
4) Cyano;
5) Optionally substituted —C$_1$-C$_8$ alkyl;
6) Optionally substituted —C$_2$-C$_8$ alkenyl;
7) Optionally substituted —C$_2$-C$_8$ alkynyl;
8) Optionally substituted —C$_3$-C$_8$ cycloalkyl;
9) Optionally substituted aryl;
10) Optionally substituted arylalkyl;
11) Optionally substituted 3- to 8-membered heterocycloalkyl;
12) Optionally substituted heteroaryl;
13) Optionally substituted heteroarylalkyl;
14) —N(R$^6$)(R$^7$);
15) —S(O)$_2$N(R$^6$)(R$^7$);
16) —N(R$^6$)C(O)(R$^7$); and
17) —N(R$^6$)S(O)$_2$(R$^7$);
wherein R$^6$ and R$^7$ are as previously defined.

In another embodiment, the present invention provides a pharmaceutical composition comprising a therapeutically effective amount of a compound or combination of compounds of the present invention, or a pharmaceutically acceptable salt form, stereoisomer, solvate, hydrate or combination thereof, in combination with a pharmaceutically acceptable carrier or excipient.

In another embodiment, the present invention provides a method for the prevention or treatment of an ASK-1 mediated disease or condition. The method comprises administering a therapeutically effective amount of a compound of Formula (I). The present invention also provides the use of a compound of Formula (I) for the preparation of a medicament for the prevention or treatment of an ASK-1 mediated disease or condition. Such diseases include autoimmune disorders, neurodegenerative disorders, inflammatory diseases, chronic kidney disease, cardiovascular disease, metabolic disorders, and acute and chronic liver diseases.

DETAILED DESCRIPTION OF THE INVENTION

A first embodiment of the invention is a compound represented by Formula (I) as described above, or a pharmaceutically acceptable salt or ester thereof.

In certain embodiments, the present invention relates to compounds of Formula (I), and pharmaceutically acceptable salts, ester, stereoisomer, tautomer, solvate, hydrate or combination thereof, wherein

is selected from the groups below:

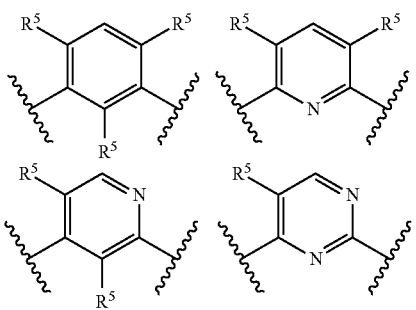

-continued

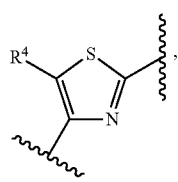

wherein each of these groups is optionally substituted when possible, and each $R^5$ and $R^4$ is as previously defined.

In certain embodiments, the present invention relates to compounds of Formula (I), and pharmaceutically acceptable salts and esters thereof, wherein $X^1$ is —N—, —C(F) or —C(OMe)-.

In certain embodiments, the present invention relates to compounds of Formula (I), and pharmaceutically acceptable salts and esters thereof, wherein $R^1$ is selected from the groups below:

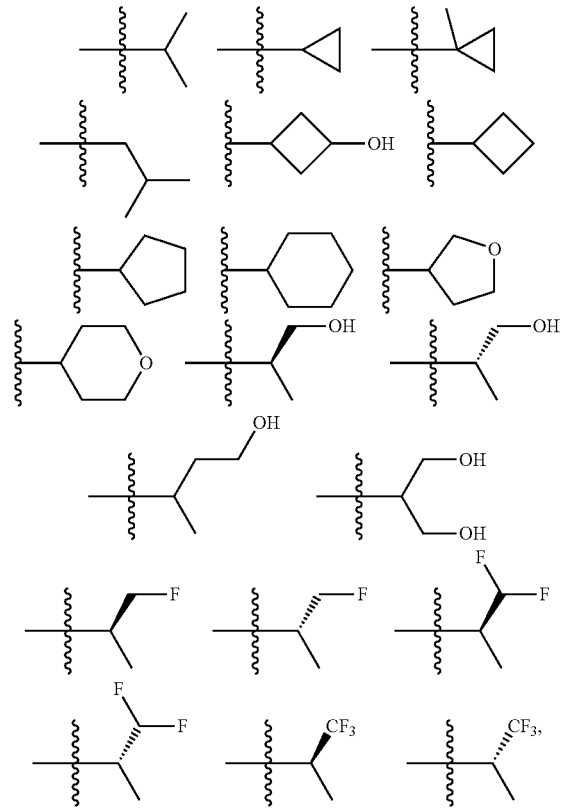

wherein each of these groups is optionally substituted.

In certain embodiments, the present invention relates to compounds of Formula (I), and pharmaceutically acceptable salts and esters thereof, wherein $R^2$ is selected from the groups below:

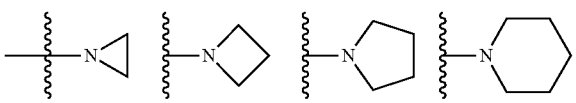

-continued

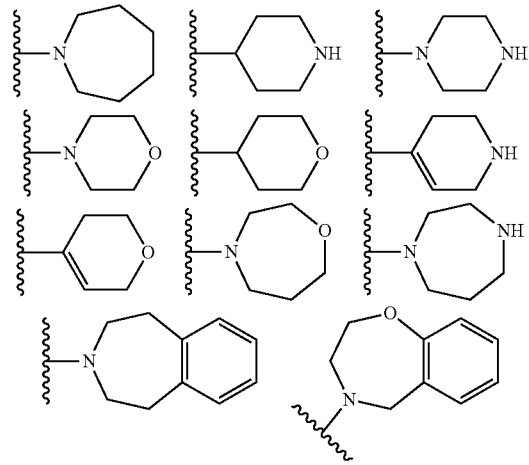

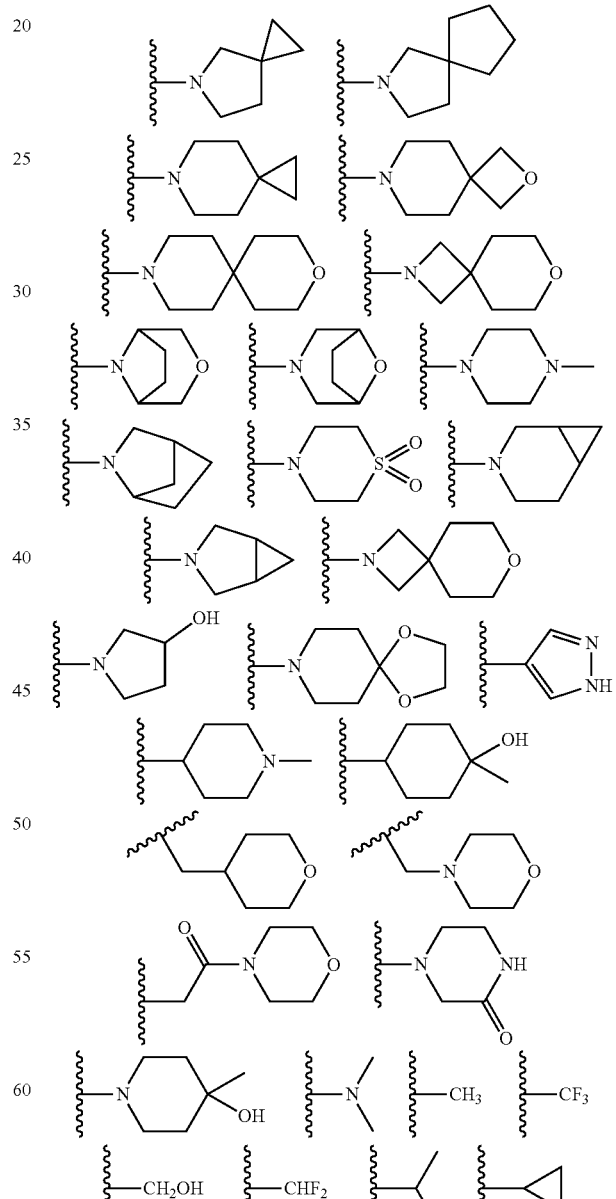

wherein each of these groups is optionally substituted.

In certain embodiments, the present invention relates to compounds of Formula (I), and pharmaceutically acceptable salts and esters thereof, wherein $R^3$ is selected from the groups below:

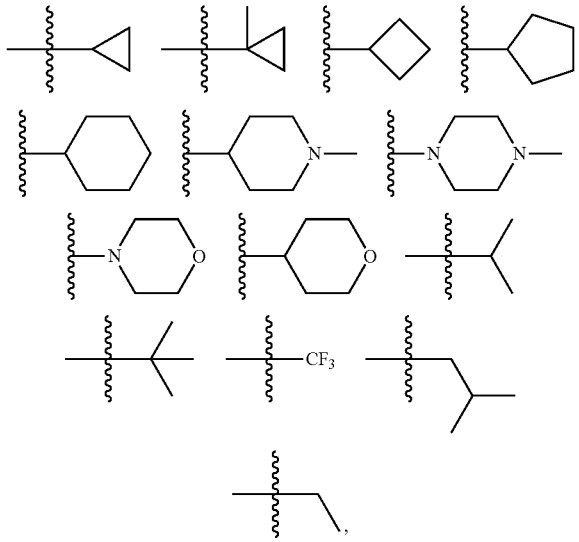

wherein each of these groups is optionally substituted.

In one embodiment, the invention provides a compound represented by Formula (Ia), (Ib), (Ic), or (Id), or a pharmaceutically acceptable salt or ester thereof:

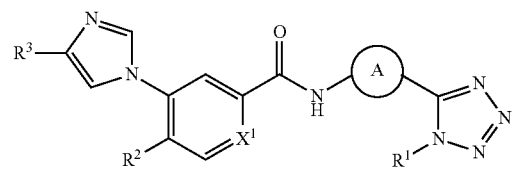
(Ia)

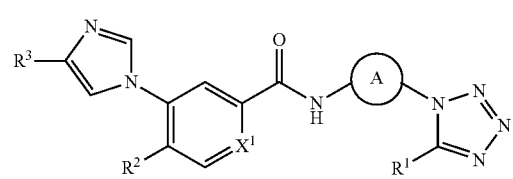
(Ib)

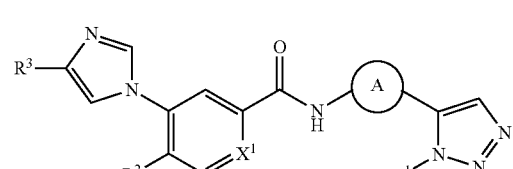
(Ic)

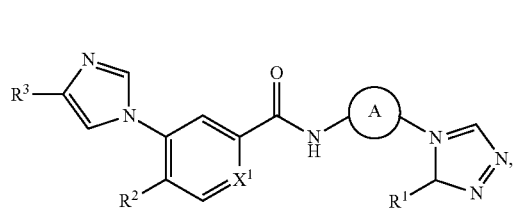
(Id)

wherein

$R^1$, $R^2$, $R^3$ and $X^1$ are as previously defined.

In one embodiment, the invention provides a compound represented by Formula (IIa), or (IIb), or a pharmaceutically acceptable salt or ester thereof:

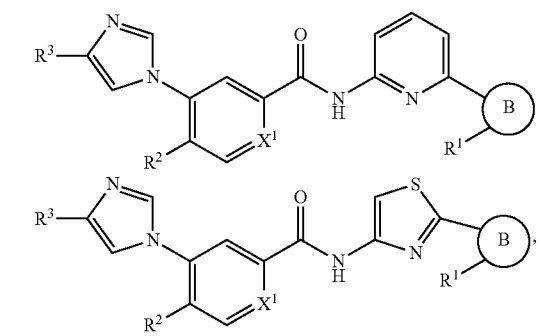

wherein $R^1$, $R^2$, $R^3$ and $X^1$ are as previously defined.

is selected from the groups below,

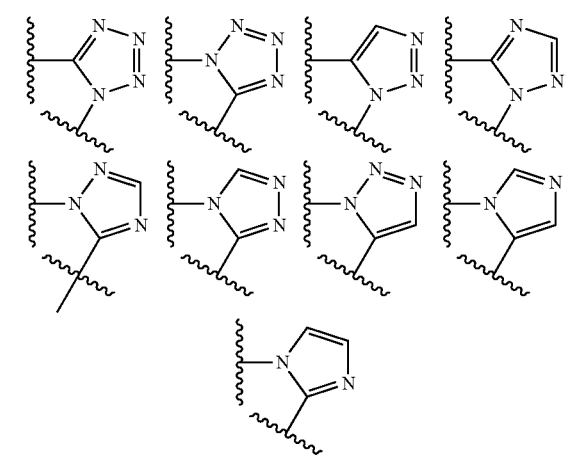

where the valence marked

is attached to the pyridine or thiazole ring, the valence marked

is attached to $R^1$, and each triazole or imidazole ring is optionally further substituted. Preferably,

is not further substituted.

In one embodiment, the invention provides a compound represented by one of Formulas (IIa-1)~(IIa-4), and (IIb-1)~(IIb-4), or a pharmaceutically acceptable salt or ester thereof:

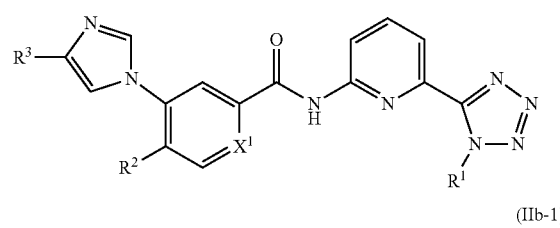

(IIa-1)

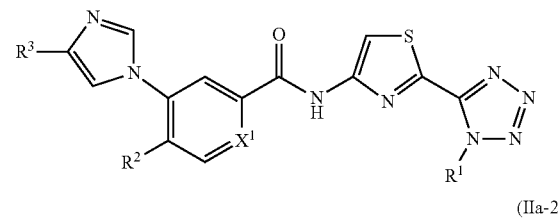

(IIb-1)

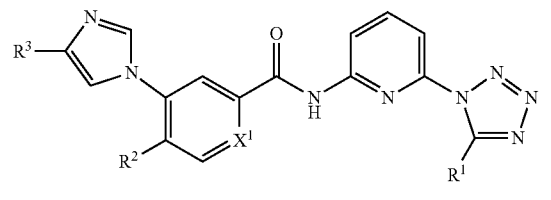

(IIa-2)

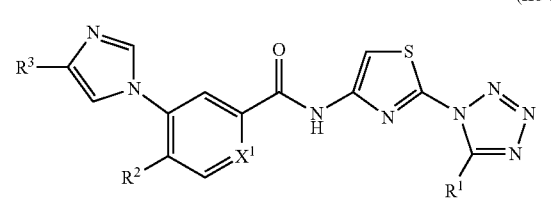

(IIb-2)

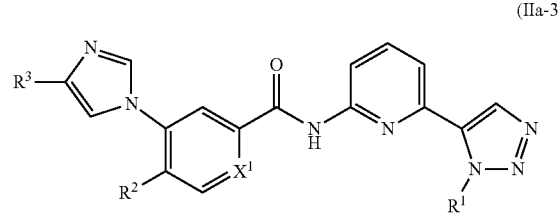

(IIa-3)

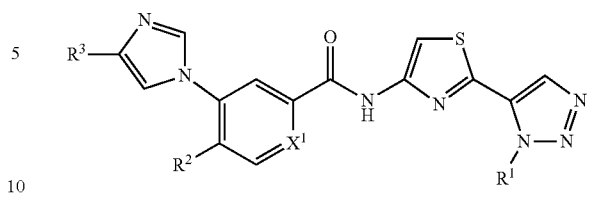

(IIb-3)

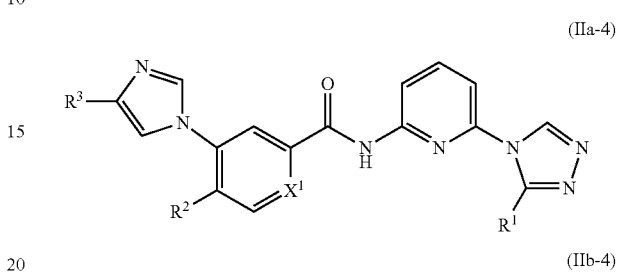

(IIa-4)

(IIb-4)

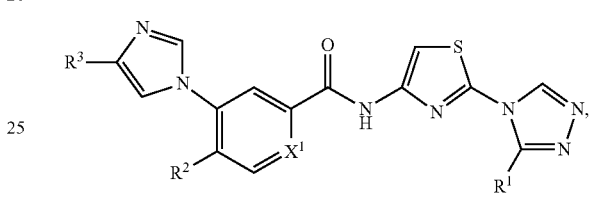

wherein $R^1$, $R^2$ and $X^1$ are as previously defined.

In one embodiment, the invention provides a compound represented by Formulas (IIIa) or (IIIb), or a pharmaceutically acceptable salt or ester thereof:

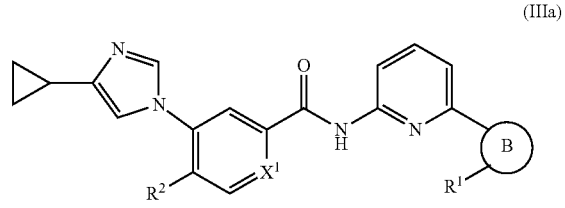

(IIIa)

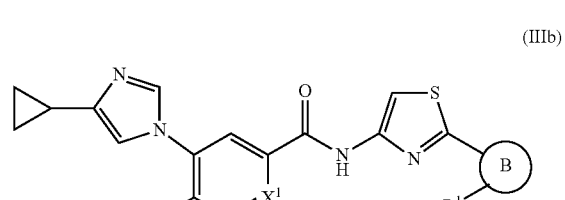

(IIIb)

wherein

$R^1$, $R^2$ and $X^1$ are as previously defined.

In one embodiment, the invention provides a compound represented by one of Formulas (IIIa-1)~(IIIa-4), and (IIIb-1)~(IIIb-4), or a pharmaceutically acceptable salt or ester thereof:

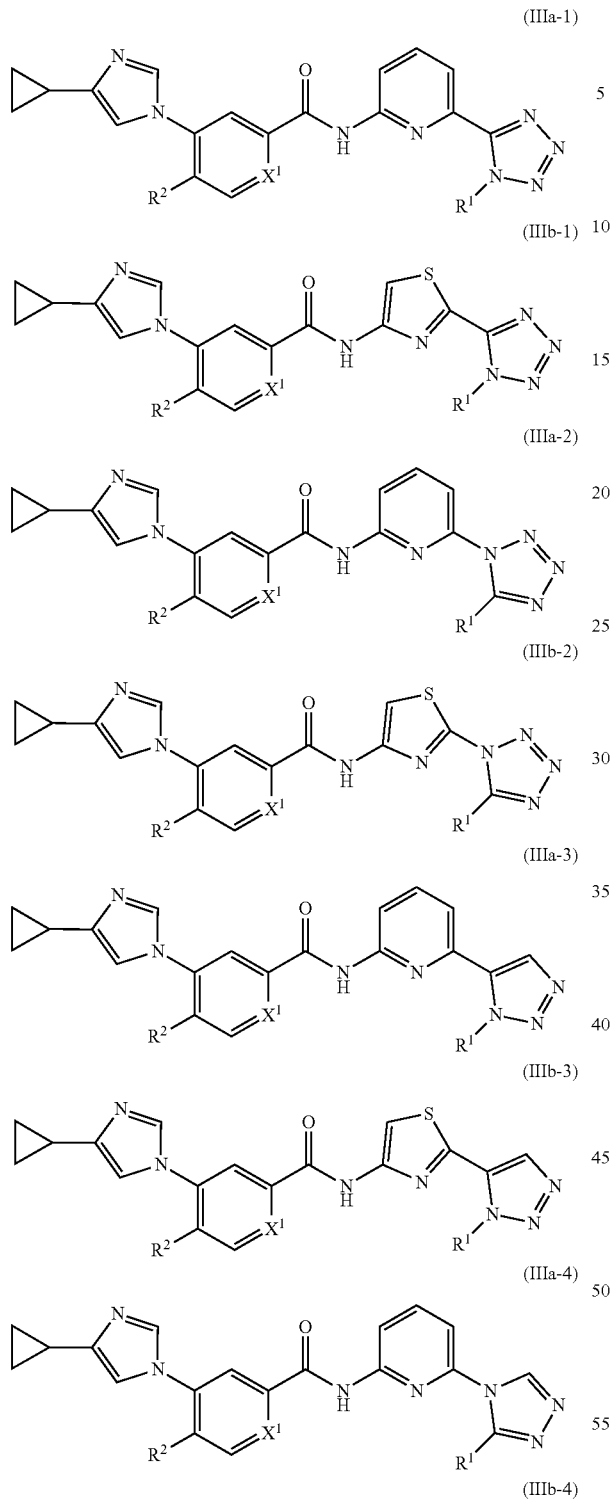

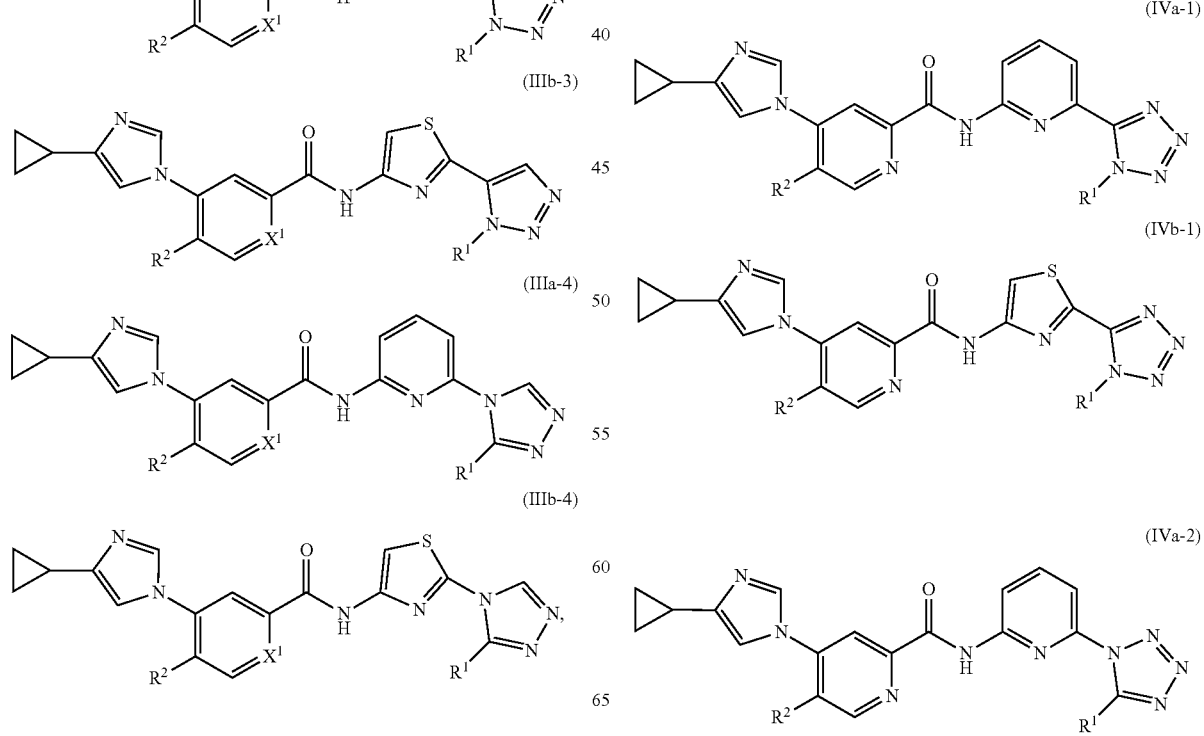

wherein $R^1$, $R^2$, and $X^1$ are as previously defined.

In one embodiment, the invention provides a compound represented by Formula (IVa) or (IV), or a pharmaceutically acceptable salt or ester thereof:

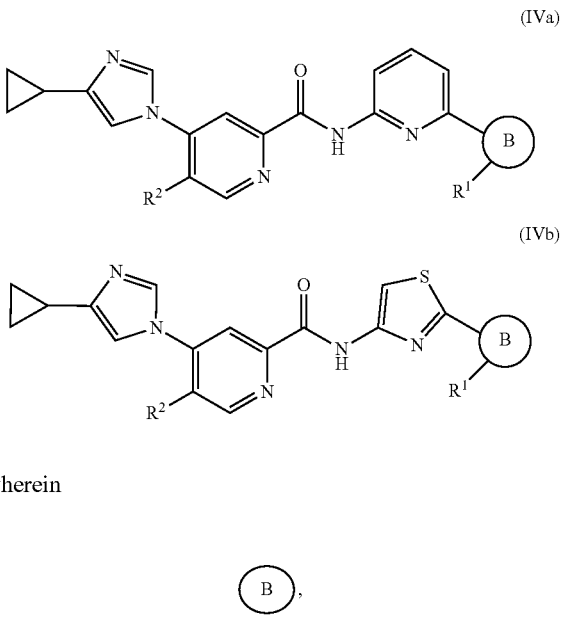

wherein (B), $R^1$, and $R^2$ as previously defined.

In one embodiment, the invention provides a compound represented by one of Formulas (IVa-1)~(IVa-4), and (IVb-1)~(IVb-4), or a pharmaceutically acceptable salt or ester thereof.

-continued

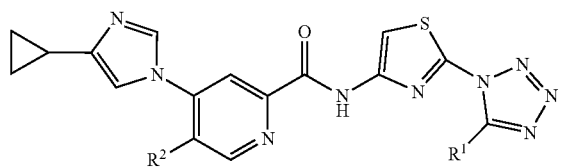
(IVb-2)

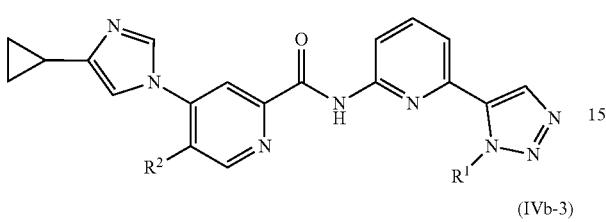
(IVa-3)

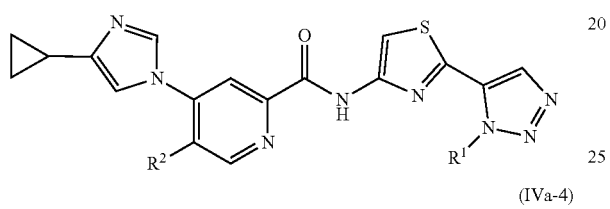
(IVb-3)

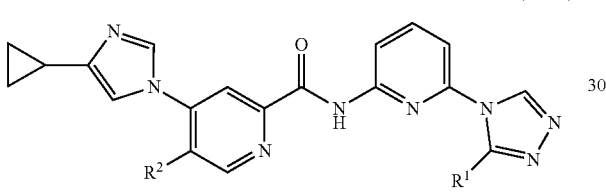
(IVa-4)

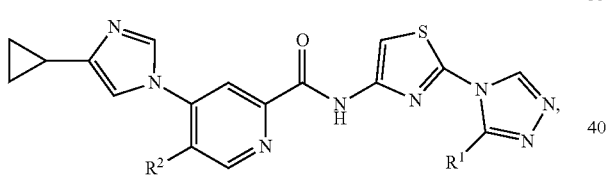
(IVb-4)

wherein $R^1$, and $R^2$ are as previously defined.

In one embodiment, the invention provides a compound represented by Formula (Va) or (Vb), or a pharmaceutically acceptable salt or ester thereof:

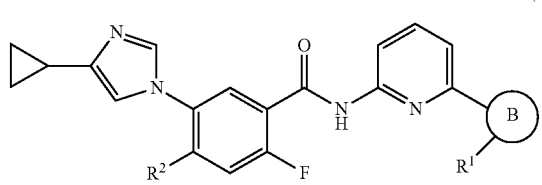
(Va)

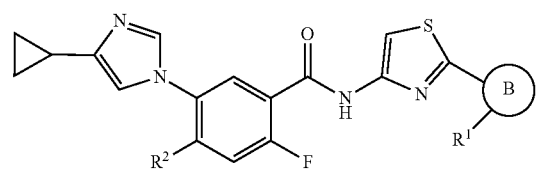
(Vb)

wherein

$R^1$, and $R^2$ are as previously defined.

In one embodiment, the invention provides a compound represented by one of (Formulas (Va-1)~(Va-4), and (Vb-1)~(Vb-4), or a pharmaceutically acceptable salt or ester thereof.

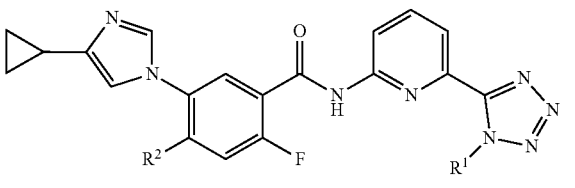
(Va-1)

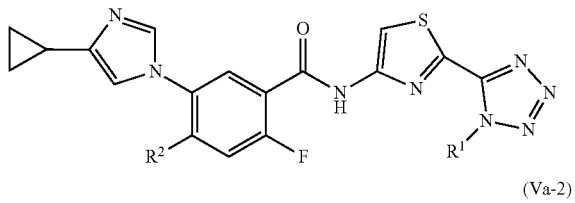
(Va-2)

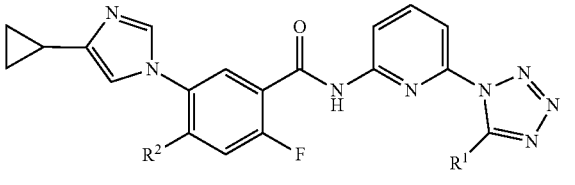
(Va-3)

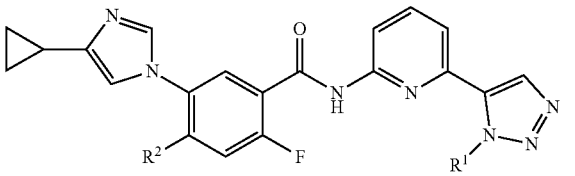
(Vb-1)

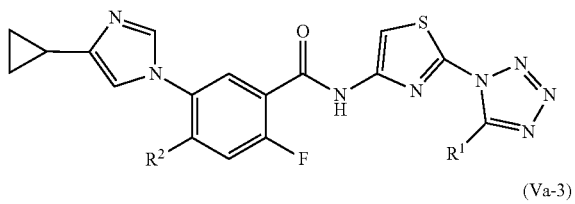
(Vb-2)

(Vb-3)

wherein R¹, and R² are as previously defined.

In one embodiment, the invention provides a compound represented by Formula (VIa) or (VIb), or a pharmaceutically acceptable salt or ester thereof:

(VIa)

(VIb)

wherein (B),

R¹, and R² are as previously defined.

In one embodiment, the invention provides a compound represented by one of Formulas (VIa-1)~(VIa-4), and (VIb-1)~(VIb-4), or a pharmaceutically acceptable salt or ester thereof:

(VIa-1)

(VIa-2)

(VIa-3)

(VIa-4)

(VIb-1)

(VIb-2)

(VIb-3)

(VIb-4)

wherein R¹, and R² are as previously defined.

Representative compounds of the invention include, but are not limited to, the following compounds (Entry 1 to Entry 100 in Table 1) according to Formula (IVa), wherein R¹ and R² are delineated for each compound in Table 1, and

is as previously defined and is not further substituted.

(IVa)

TABLE 1

| Entry | R¹ | R² |
|---|---|---|
| 1 | cyclopropyl | Me |
| 2 | 1-methylcyclopropyl | Me |
| 3 | isopropyl | Me |
| 4 | cyclopentyl | Me |
| 5 | CH(Me)CH₂OH | Me |
| 6 | CH(Me)CH₂OH (epimer) | Me |
| 7 | CH(Me)CH₂F | Me |
| 8 | CH(Me)CH₂F (epimer) | Me |
| 9 | CH(Me)CHF₂ | Me |
| 10 | CH(Me)CHF₂ (epimer) | Me |
| 11 | cyclopropyl | CF₃ |
| 12 | 1-methylcyclopropyl | CF₃ |
| 13 | isopropyl | CF₃ |
| 14 | cyclopentyl | CF₃ |
| 15 | CH(Me)CH₂OH | CF₃ |
| 16 | CH(Me)CH₂OH (epimer) | CF₃ |
| 17 | CH(Me)CH₂F | CF₃ |
| 18 | CH(Me)CH₂F (epimer) | CF₃ |
| 19 | CH(Me)CHF₂ | CF₃ |
| 20 | CH(Me)CHF₂ (epimer) | CF₃ |
| 21 | cyclopropyl | NMe₂ |
| 22 | 1-methylcyclopropyl | NMe₂ |
| 23 | isopropyl | NMe₂ |
| 24 | cyclopentyl | NMe₂ |

TABLE 1-continued

| Entry | R¹ | R² |
|---|---|---|
| 25 | CH(CH₃)CH₂OH (wedge) | N(CH₃)₂ |
| 26 | CH(CH₃)CH₂OH (dash) | N(CH₃)₂ |
| 27 | CH(CH₃)CH₂F (wedge) | N(CH₃)₂ |
| 28 | CH(CH₃)CH₂F (dash) | N(CH₃)₂ |
| 29 | CH(CH₃)CHF₂ (wedge) | N(CH₃)₂ |
| 30 | CH(CH₃)CHF₂ (dash) | N(CH₃)₂ |
| 31 | cyclopropyl | azetidinyl |
| 32 | 1-methylcyclopropyl | azetidinyl |
| 33 | isopropyl | azetidinyl |
| 34 | cyclopentyl | azetidinyl |
| 35 | CH(CH₃)CH₂OH (wedge) | azetidinyl |
| 36 | CH(CH₃)CH₂OH (dash) | azetidinyl |
| 37 | CH(CH₃)CH₂F (wedge) | azetidinyl |
| 38 | CH(CH₃)CH₂F (dash) | azetidinyl |

TABLE 1-continued

| Entry | R¹ | R² |
|---|---|---|
| 39 | CH(CH₃)CHF₂ (wedge) | azetidinyl |
| 40 | CH(CH₃)CHF₂ (dash) | azetidinyl |
| 41 | cyclopropyl | piperidinyl |
| 42 | 1-methylcyclopropyl | piperidinyl |
| 43 | isopropyl | piperidinyl |
| 44 | cyclopentyl | piperidinyl |
| 45 | CH(CH₃)CH₂OH (wedge) | piperidinyl |
| 46 | CH(CH₃)CH₂OH (dash) | piperidinyl |
| 47 | CH(CH₃)CH₂F (wedge) | piperidinyl |
| 48 | CH(CH₃)CH₂F (dash) | piperidinyl |
| 49 | CH(CH₃)CHF₂ (wedge) | piperidinyl |
| 50 | CH(CH₃)CHF₂ (dash) | piperidinyl |
| 51 | cyclopropyl | morpholinyl |
| 52 | cyclopropyl | morpholinyl |

TABLE 1-continued

| Entry | R¹ | R² |
|---|---|---|
| 53 | isopropyl | N-morpholine |
| 54 | cyclopentyl | N-morpholine |
| 55 | -CH(CH₃)-CH₂OH (S) | N-morpholine |
| 56 | -CH(CH₃)-CH₂OH (R) | N-morpholine |
| 57 | -CH(CH₃)-CH₂F (S) | N-morpholine |
| 58 | -CH(CH₃)-CH₂F (R) | N-morpholine |
| 59 | -CH(CH₃)-CHF₂ (S) | N-morpholine |
| 60 | -CH(CH₃)-CHF₂ (R) | N-morpholine |
| 61 | cyclopropyl | N-pyrrolidine |
| 62 | 1-methylcyclopropyl | N-pyrrolidine |
| 63 | isopropyl | N-pyrrolidine |
| 64 | cyclopentyl | N-pyrrolidine |
| 65 | -CH(CH₃)-CH₂OH (S) | N-pyrrolidine |
| 66 | -CH(CH₃)-CH₂OH (R) | N-pyrrolidine |
| 67 | -CH(CH₃)-CH₂F (S) | N-pyrrolidine |
| 68 | -CH(CH₃)-CH₂F (R) | N-pyrrolidine |
| 69 | -CH(CH₃)-CHF₂ (S) | N-pyrrolidine |
| 70 | -CH(CH₃)-CHF₂ (R) | N-pyrrolidine |
| 71 | cyclopropyl | 3-hydroxypyrrolidin-1-yl |
| 72 | 1-methylcyclopropyl | 3-hydroxypyrrolidin-1-yl |
| 73 | isopropyl | 3-hydroxypyrrolidin-1-yl |
| 74 | cyclopentyl | 3-hydroxypyrrolidin-1-yl |
| 75 | -CH(CH₃)-CH₂OH (S) | 3-hydroxypyrrolidin-1-yl |
| 76 | -CH(CH₃)-CH₂OH (R) | 3-hydroxypyrrolidin-1-yl |
| 77 | -CH(CH₃)-CH₂F (S) | 3-hydroxypyrrolidin-1-yl |
| 78 | -CH(CH₃)-CH₂F (R) | 3-hydroxypyrrolidin-1-yl |
| 79 | -CH(CH₃)-CHF₂ (S) | 3-hydroxypyrrolidin-1-yl |
| 80 | -CH(CH₃)-CHF₂ (R) | 3-hydroxypyrrolidin-1-yl |

TABLE 1-continued

| Entry | R¹ | R² |
|---|---|---|
| 81 | cyclopropyl | piperazinyl-N-methyl |
| 82 | 1-methylcyclopropyl | piperazinyl-N-methyl |
| 83 | isopropyl | piperazinyl-N-methyl |
| 84 | cyclopentyl | piperazinyl-N-methyl |
| 85 | (S)-CH(CH₃)CH₂OH | piperazinyl-N-methyl |
| 86 | (R)-CH(CH₃)CH₂OH | piperazinyl-N-methyl |
| 87 | (S)-CH(CH₃)CH₂F | piperazinyl-N-methyl |
| 88 | (R)-CH(CH₃)CH₂F | piperazinyl-N-methyl |
| 89 | (S)-CH(CH₃)CHF₂ | piperazinyl-N-methyl |
| 90 | (R)-CH(CH₃)CHF₂ | piperazinyl-N-methyl |
| 91 | cyclopropyl | 4-methyl-4-hydroxypiperidinyl |
| 92 | 1-methylcyclopropyl | 4-methyl-4-hydroxypiperidinyl |
| 93 | isopropyl | 4-methyl-4-hydroxypiperidinyl |
| 94 | cyclopentyl | 4-methyl-4-hydroxypiperidinyl |
| 95 | (S)-CH(CH₃)CH₂OH | 4-methyl-4-hydroxypiperidinyl |
| 96 | (R)-CH(CH₃)CH₂OH | 4-methyl-4-hydroxypiperidinyl |
| 97 | (S)-CH(CH₃)CH₂F | 4-methyl-4-hydroxypiperidinyl |
| 98 | (R)-CH(CH₃)CH₂F | 4-methyl-4-hydroxypiperidinyl |
| 99 | (S)-CH(CH₃)CHF₂ | 4-methyl-4-hydroxypiperidinyl |
| 100 | (R)-CH(CH₃)CHF₂ | 4-methyl-4-hydroxypiperidinyl |

Representative compounds of the invention include, but are not limited to, the following compounds (Entry 101 to Entry 200 in Table 2) according to Formula (IVb), wherein R¹ and R² are delineated for each compound in Table 2, and (B)

is as previously defined and is not further substituted.

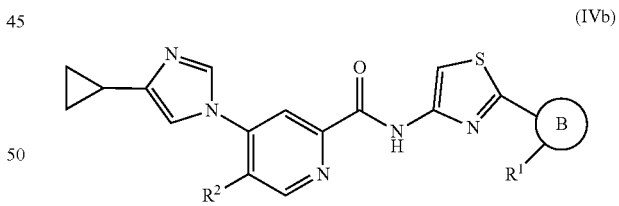

(IVb)

TABLE 2

| Entry | R¹ | R² |
|---|---|---|
| 101 | cyclopropyl | Me |
| 102 | 1-methylcyclopropyl | Me |

TABLE 2-continued

| Entry | R¹ | R² |
|---|---|---|
| 103 | isopropyl | Me |
| 104 | cyclopentyl | Me |
| 105 | CH(CH₃)CH₂OH (wedge) | Me |
| 106 | CH(CH₃)CH₂OH (dash) | Me |
| 107 | CH(CH₃)CH₂F (wedge) | Me |
| 108 | CH(CH₃)CH₂F (dash) | Me |
| 109 | CH(CH₃)CHF₂ (wedge) | Me |
| 110 | CH(CH₃)CHF₂ (dash) | Me |
| 111 | cyclopropyl | CF₃ |
| 112 | 1-methylcyclopropyl | CF₃ |
| 113 | isopropyl | CF₃ |
| 114 | cyclopentyl | CF₃ |
| 115 | CH(CH₃)CH₂OH (wedge) | CF₃ |
| 116 | CH(CH₃)CH₂OH (dash) | CF₃ |
| 117 | CH(CH₃)CH₂F (wedge) | CF₃ |
| 118 | CH(CH₃)CH₂F (dash) | CF₃ |
| 119 | CH(CH₃)CHF₂ (wedge) | CF₃ |
| 120 | CH(CH₃)CHF₂ (dash) | CF₃ |
| 121 | cyclopropyl | N(CH₃)₂ |
| 122 | 1-methylcyclopropyl | N(CH₃)₂ |
| 123 | isopropyl | N(CH₃)₂ |
| 124 | cyclopentyl | N(CH₃)₂ |
| 125 | CH(CH₃)CH₂OH (wedge) | N(CH₃)₂ |
| 126 | CH(CH₃)CH₂OH (dash) | N(CH₃)₂ |
| 127 | CH(CH₃)CH₂F (wedge) | N(CH₃)₂ |
| 128 | CH(CH₃)CH₂F (dash) | N(CH₃)₂ |
| 129 | CH(CH₃)CHF₂ (wedge) | N(CH₃)₂ |
| 130 | CH(CH₃)CHF₂ (dash) | N(CH₃)₂ |

TABLE 2-continued

| Entry | R¹ | R² |
|---|---|---|
| 131 | cyclopropyl | N-azetidinyl |
| 132 | 1-methylcyclopropyl | N-azetidinyl |
| 133 | isopropyl | N-azetidinyl |
| 134 | cyclopentyl | N-azetidinyl |
| 135 | -CH(CH₃)CH₂OH (wedge) | N-azetidinyl |
| 136 | -CH(CH₃)CH₂OH (dash) | N-azetidinyl |
| 137 | -CH(CH₃)CH₂F (wedge) | N-azetidinyl |
| 138 | -CH(CH₃)CH₂F (dash) | N-azetidinyl |
| 139 | -CH(CH₃)CHF₂ (wedge) | N-azetidinyl |
| 140 | -CH(CH₃)CHF₂ (dash) | N-azetidinyl |
| 141 | cyclopropyl | N-piperidinyl |
| 142 | 1-methylcyclopropyl | N-piperidinyl |
| 143 | isopropyl | N-piperidinyl |
| 144 | cyclopentyl | N-piperidinyl |
| 145 | -CH(CH₃)CH₂OH (wedge) | N-piperidinyl |
| 146 | -CH(CH₃)CH₂OH (dash) | N-piperidinyl |
| 147 | -CH(CH₃)CH₂F (wedge) | N-piperidinyl |
| 148 | -CH(CH₃)CH₂F (dash) | N-piperidinyl |
| 149 | -CH(CH₃)CHF₂ (wedge) | N-piperidinyl |
| 150 | -CH(CH₃)CHF₂ (dash) | N-piperidinyl |
| 151 | cyclopropyl | N-morpholinyl |
| 152 | 1-methylcyclopropyl | N-morpholinyl |
| 153 | isopropyl | N-morpholinyl |
| 154 | cyclopentyl | N-morpholinyl |
| 155 | -CH(CH₃)CH₂OH (wedge) | N-morpholinyl |
| 156 | -CH(CH₃)CH₂OH (dash) | N-morpholinyl |
| 157 | -CH(CH₃)CH₂F (wedge) | N-morpholinyl |
| 158 | -CH(CH₃)CH₂F (dash) | N-morpholinyl |
| 159 | -CH(CH₃)CHF₂ (wedge) | N-morpholinyl |
| 160 | -CH(CH₃)CHF₂ (dash) | N-morpholinyl |

TABLE 2-continued

| Entry | R¹ | R² |
|---|---|---|
| 161 | cyclopropyl | pyrrolidin-1-yl |
| 162 | 1-methylcyclopropyl | pyrrolidin-1-yl |
| 163 | isopropyl | pyrrolidin-1-yl |
| 164 | cyclopentyl | pyrrolidin-1-yl |
| 165 | CH(CH₃)CH₂OH (R) | pyrrolidin-1-yl |
| 166 | CH(CH₃)CH₂OH (S) | pyrrolidin-1-yl |
| 167 | CH(CH₃)CH₂F (R) | pyrrolidin-1-yl |
| 168 | CH(CH₃)CH₂F (S) | pyrrolidin-1-yl |
| 169 | CH(CH₃)CHF₂ (R) | pyrrolidin-1-yl |
| 170 | CH(CH₃)CHF₂ (S) | pyrrolidin-1-yl |
| 171 | cyclopropyl | 3-hydroxypyrrolidin-1-yl |
| 172 | 1-methylcyclopropyl | 3-hydroxypyrrolidin-1-yl |
| 173 | isopropyl | 3-hydroxypyrrolidin-1-yl |
| 174 | cyclopentyl | 3-hydroxypyrrolidin-1-yl |
| 175 | CH(CH₃)CH₂OH (R) | 3-hydroxypyrrolidin-1-yl |
| 176 | CH(CH₃)CH₂OH (S) | 3-hydroxypyrrolidin-1-yl |
| 177 | CH(CH₃)CH₂F (R) | 3-hydroxypyrrolidin-1-yl |
| 178 | CH(CH₃)CH₂F (S) | 3-hydroxypyrrolidin-1-yl |
| 179 | CH(CH₃)CHF₂ (R) | 3-hydroxypyrrolidin-1-yl |
| 180 | CH(CH₃)CHF₂ (S) | 3-hydroxypyrrolidin-1-yl |
| 181 | cyclopropyl | 4-methylpiperazin-1-yl |
| 182 | 1-methylcyclopropyl | 4-methylpiperazin-1-yl |
| 183 | isopropyl | 4-methylpiperazin-1-yl |
| 184 | cyclopentyl | 4-methylpiperazin-1-yl |
| 185 | CH(CH₃)CH₂OH (R) | 4-methylpiperazin-1-yl |
| 186 | CH(CH₃)CH₂OH (S) | 4-methylpiperazin-1-yl |
| 187 | CH(CH₃)CH₂F (R) | 4-methylpiperazin-1-yl |
| 188 | CH(CH₃)CH₂F (S) | 4-methylpiperazin-1-yl |
| 189 | CH(CH₃)CHF₂ (R) | 4-methylpiperazin-1-yl |
| 190 | CH(CH₃)CHF₂ (S) | 4-methylpiperazin-1-yl |
| 191 | cyclopropyl | 4-hydroxy-4-methylpiperidin-1-yl |
| 192 | 1-methylcyclopropyl | 4-hydroxy-4-methylpiperidin-1-yl |
| 193 | isopropyl | 4-hydroxy-4-methylpiperidin-1-yl |
| 194 | cyclopentyl | 4-hydroxy-4-methylpiperidin-1-yl |

TABLE 2-continued

| Entry | R¹ | R² |
|---|---|---|
| 195 | -CH(CH₃)CH₂OH | 4-methyl-4-hydroxypiperidinyl |
| 196 | -CH(CH₃)CH₂OH (epimer) | 4-methyl-4-hydroxypiperidinyl |
| 197 | -CH(CH₃)CH₂F | 4-methyl-4-hydroxypiperidinyl |
| 198 | -CH(CH₃)CH₂F (epimer) | 4-methyl-4-hydroxypiperidinyl |
| 199 | -CH(CH₃)CHF₂ | 4-methyl-4-hydroxypiperidinyl |
| 200 | -CH(CH₃)CHF₂ (epimer) | 4-methyl-4-hydroxypiperidinyl |

Representative compounds of the invention include, but are not limited to, the following compounds (Entry 201 to Entry 300 in Table 3) according to Formula (Va), wherein R and R² are delineated for each compound in Table 3, and

is as previously defined and is not further substituted.

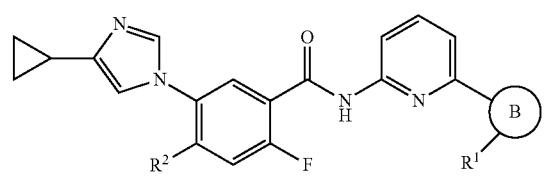

(Va)

TABLE 3

| Entry | R¹ | R² |
|---|---|---|
| 201 | cyclopropyl | Me |
| 202 | 1-methylcyclopropyl | Me |
| 203 | isopropyl | Me |
| 204 | cyclopentyl | Me |
| 205 | -CH(CH₃)CH₂OH | Me |
| 206 | -CH(CH₃)CH₂OH (epimer) | Me |
| 207 | -CH(CH₃)CH₂F | Me |
| 208 | -CH(CH₃)CH₂F (epimer) | Me |
| 209 | -CH(CH₃)CHF₂ | Me |
| 210 | -CH(CH₃)CHF₂ (epimer) | Me |
| 211 | cyclopropyl | CF₃ |
| 212 | 1-methylcyclopropyl | CF₃ |
| 213 | isopropyl | CF₃ |
| 214 | cyclopentyl | CF₃ |
| 215 | -CH(CH₃)CH₂OH | CF₃ |
| 216 | -CH(CH₃)CH₂OH (epimer) | CF₃ |
| 217 | -CH(CH₃)CH₂F | CF₃ |

TABLE 3-continued

| Entry | R¹ | R² |
|---|---|---|
| 218 | CH₂F (wedge down methyl) | CF₃ |
| 219 | CHF₂ (wedge methyl) | CF₃ |
| 220 | CHF₂ (wedge down methyl) | CF₃ |
| 221 | cyclopropyl | N(CH₃)₂ |
| 222 | 1-methylcyclopropyl | N(CH₃)₂ |
| 223 | isopropyl | N(CH₃)₂ |
| 224 | cyclopentyl | N(CH₃)₂ |
| 225 | CH₂OH (wedge methyl) | N(CH₃)₂ |
| 226 | CH₂OH (wedge down methyl) | N(CH₃)₂ |
| 227 | CH₂F (wedge methyl) | N(CH₃)₂ |
| 228 | CH₂F (wedge down methyl) | N(CH₃)₂ |
| 229 | CHF₂ (wedge methyl) | N(CH₃)₂ |
| 230 | CHF₂ (wedge down methyl) | N(CH₃)₂ |
| 231 | cyclopropyl | azetidinyl |

TABLE 3-continued

| Entry | R¹ | R² |
|---|---|---|
| 232 | 1-methylcyclopropyl | azetidinyl |
| 233 | isopropyl | azetidinyl |
| 234 | cyclopentyl | azetidinyl |
| 135 | CH₂OH (wedge methyl) | azetidinyl |
| 236 | CH₂OH (wedge down methyl) | azetidinyl |
| 237 | CH₂F (wedge methyl) | azetidinyl |
| 238 | CH₂F (wedge down methyl) | azetidinyl |
| 239 | CHF₂ (wedge methyl) | azetidinyl |
| 240 | CHF₂ (wedge down methyl) | azetidinyl |
| 241 | cyclopropyl | piperidinyl |
| 242 | 1-methylcyclopropyl | piperidinyl |
| 243 | isopropyl | piperidinyl |
| 244 | cyclopentyl | piperidinyl |
| 245 | CH₂OH (wedge methyl) | piperidinyl |

TABLE 3-continued

| Entry | R¹ | R² |
|---|---|---|
| 246 | CH₂OH, CH₃ (stereo) | piperidine (N-linked) |
| 247 | CH₂F, CH₃ (wedge) | piperidine (N-linked) |
| 248 | CH₂F, CH₃ (dash) | piperidine (N-linked) |
| 249 | CHF₂, CH₃ (wedge) | piperidine (N-linked) |
| 250 | CHF₂, CH₃ (dash) | piperidine (N-linked) |
| 251 | cyclopropyl | morpholine (N-linked) |
| 252 | 1-methylcyclopropyl | morpholine (N-linked) |
| 253 | isopropyl | morpholine (N-linked) |
| 254 | cyclopentyl | morpholine (N-linked) |
| 255 | CH₂OH, CH₃ (wedge) | morpholine (N-linked) |
| 256 | CH₂OH, CH₃ (dash) | morpholine (N-linked) |
| 257 | CH₂F, CH₃ (wedge) | morpholine (N-linked) |
| 258 | CH₂F, CH₃ (dash) | morpholine (N-linked) |
| 259 | CHF₂, CH₃ (wedge) | morpholine (N-linked) |
| 260 | CHF₂, CH₃ (dash) | morpholine (N-linked) |
| 261 | cyclopropyl | pyrrolidine (N-linked) |
| 262 | 1-methylcyclopropyl | pyrrolidine (N-linked) |
| 263 | isopropyl | pyrrolidine (N-linked) |
| 264 | cyclopentyl | pyrrolidine (N-linked) |
| 265 | CH₂OH, CH₃ (wedge) | pyrrolidine (N-linked) |
| 266 | CH₂OH, CH₃ (dash) | pyrrolidine (N-linked) |
| 267 | CH₂F, CH₃ (wedge) | pyrrolidine (N-linked) |
| 268 | CH₂F, CH₃ (dash) | pyrrolidine (N-linked) |
| 269 | CHF₂, CH₃ (wedge) | pyrrolidine (N-linked) |
| 270 | CHF₂, CH₃ (dash) | pyrrolidine (N-linked) |
| 271 | cyclopropyl | 3-hydroxypyrrolidine (N-linked) |
| 272 | 1-methylcyclopropyl | 3-hydroxypyrrolidine (N-linked) |
| 273 | isopropyl | 3-hydroxypyrrolidine (N-linked) |

TABLE 3-continued

| Entry | R¹ | R² |
|---|---|---|
| 274 | cyclopentyl | N-pyrrolidinyl-3-OH |
| 275 | CH(CH₃)CH₂OH (wedge) | N-pyrrolidinyl-3-OH |
| 276 | CH(CH₃)CH₂OH (dash) | N-pyrrolidinyl-3-OH |
| 277 | CH(CH₃)CH₂F (wedge) | N-pyrrolidinyl-3-OH |
| 278 | CH(CH₃)CH₂F (dash) | N-pyrrolidinyl-3-OH |
| 279 | CH(CH₃)CHF₂ (wedge) | N-pyrrolidinyl-3-OH |
| 280 | CH(CH₃)CHF₂ (dash) | N-pyrrolidinyl-3-OH |
| 281 | cyclopropyl | N-methylpiperazinyl |
| 282 | 1-methylcyclopropyl | N-methylpiperazinyl |
| 283 | isopropyl | N-methylpiperazinyl |
| 284 | cyclopentyl | N-methylpiperazinyl |
| 285 | CH(CH₃)CH₂OH (wedge) | N-methylpiperazinyl |
| 286 | CH(CH₃)CH₂OH (dash) | N-methylpiperazinyl |
| 287 | CH(CH₃)CH₂F (wedge) | N-methylpiperazinyl |
| 288 | CH(CH₃)CH₂F (dash) | N-methylpiperazinyl |
| 289 | CH(CH₃)CHF₂ (wedge) | N-methylpiperazinyl |
| 290 | CH(CH₃)CHF₂ (dash) | N-methylpiperazinyl |
| 291 | cyclopropyl | 4-methyl-4-hydroxypiperidinyl |
| 292 | 1-methylcyclopropyl | 4-methyl-4-hydroxypiperidinyl |
| 293 | isopropyl | 4-methyl-4-hydroxypiperidinyl |
| 294 | cyclopentyl | 4-methyl-4-hydroxypiperidinyl |
| 295 | CH(CH₃)CH₂OH (wedge) | 4-methyl-4-hydroxypiperidinyl |
| 296 | CH(CH₃)CH₂OH (dash) | 4-methyl-4-hydroxypiperidinyl |
| 297 | CH(CH₃)CH₂F (wedge) | 4-methyl-4-hydroxypiperidinyl |
| 298 | CH(CH₃)CH₂F (dash) | 4-methyl-4-hydroxypiperidinyl |
| 299 | CH(CH₃)CHF₂ (wedge) | 4-methyl-4-hydroxypiperidinyl |
| 300 | CH(CH₃)CHF₂ (dash) | 4-methyl-4-hydroxypiperidinyl |

Representative compounds of the invention include, but are not limited to, the following compounds (Entry 301 to Entry 400 in Table 4) according to Formula (Vb), wherein R¹ and R² are delineated for each compound in Table 4, and

is as previously defined and is not further substituted.

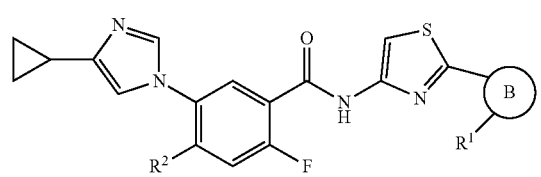

TABLE 4

| Entry | R¹ | R² |
|---|---|---|
| 301 | cyclopropyl-CH< | Me |
| 302 | 1-methylcyclopropyl | Me |
| 303 | isopropyl | Me |
| 304 | cyclopentyl | Me |
| 305 | -CH(Me)-CH₂OH | Me |
| 306 | -CH(Me)-CH₂OH | Me |
| 307 | -CH(Me)-CH₂F | Me |
| 308 | -CH(Me)-CH₂F | Me |
| 309 | -CH(Me)-CHF₂ | Me |
| 310 | -CH(Me)-CHF₂ | Me |

TABLE 4-continued

| Entry | R¹ | R² |
|---|---|---|
| 311 | cyclopropyl-CH< | CF₃ |
| 312 | 1-methylcyclopropyl | CF₃ |
| 313 | isopropyl | CF₃ |
| 314 | cyclopentyl | CF₃ |
| 315 | -CH(Me)-CH₂OH | CF₃ |
| 316 | -CH(Me)-CH₂OH | CF₃ |
| 317 | -CH(Me)-CH₂F | CF₃ |
| 318 | -CH(Me)-CH₂F | CF₃ |
| 319 | -CH(Me)-CHF₂ | CF₃ |
| 320 | -CH(Me)-CHF₂ | CF₃ |
| 321 | cyclopropyl-CH< | -N(Me)₂ |
| 322 | 1-methylcyclopropyl | -N(Me)₂ |
| 323 | isopropyl | -N(Me)₂ |
| 324 | cyclopentyl | -N(Me)₂ |

TABLE 4-continued

| Entry | R¹ | R² |
|---|---|---|
| 325 | CH(CH₃)CH₂OH (wedge) | N(CH₃)₂ |
| 326 | CH(CH₃)CH₂OH (dash) | N(CH₃)₂ |
| 327 | CH(CH₃)CH₂F (wedge) | N(CH₃)₂ |
| 328 | CH(CH₃)CH₂F (dash) | N(CH₃)₂ |
| 329 | CH(CH₃)CHF₂ (wedge) | N(CH₃)₂ |
| 330 | CH(CH₃)CHF₂ (dash) | N(CH₃)₂ |
| 331 | cyclopropyl | azetidinyl |
| 332 | 1-methylcyclopropyl | azetidinyl |
| 333 | isopropyl | azetidinyl |
| 334 | cyclopentyl | azetidinyl |
| 335 | CH(CH₃)CH₂OH (wedge) | azetidinyl |
| 336 | CH(CH₃)CH₂OH (dash) | azetidinyl |
| 337 | CH(CH₃)CH₂F (wedge) | azetidinyl |
| 338 | CH(CH₃)CH₂F (dash) | azetidinyl |
| 339 | CH(CH₃)CHF₂ (wedge) | azetidinyl |
| 340 | CH(CH₃)CHF₂ (dash) | azetidinyl |
| 341 | cyclopropyl | piperidinyl |
| 342 | 1-methylcyclopropyl | piperidinyl |
| 343 | isopropyl | piperidinyl |
| 344 | cyclopentyl | piperidinyl |
| 345 | CH(CH₃)CH₂OH (wedge) | piperidinyl |
| 346 | CH(CH₃)CH₂OH (dash) | piperidinyl |
| 347 | CH(CH₃)CH₂F (wedge) | piperidinyl |
| 348 | CH(CH₃)CH₂F (dash) | piperidinyl |
| 349 | CH(CH₃)CHF₂ (wedge) | piperidinyl |
| 350 | CH(CH₃)CHF₂ (dash) | piperidinyl |
| 351 | cyclopropyl | morpholinyl |
| 352 | 1-methylcyclopropyl | morpholinyl |

TABLE 4-continued

| Entry | R¹ | R² |
|---|---|---|
| 353 | isopropyl | morpholine (N-linked) |
| 354 | cyclopentyl | morpholine (N-linked) |
| 355 | -CH(CH₃)-CH₂OH (wedge) | morpholine (N-linked) |
| 356 | -CH(CH₃)-CH₂OH (dash) | morpholine (N-linked) |
| 357 | -CH(CH₃)-CH₂F (wedge) | morpholine (N-linked) |
| 358 | -CH(CH₃)-CH₂F (dash) | morpholine (N-linked) |
| 359 | -CH(CH₃)-CHF₂ (wedge) | morpholine (N-linked) |
| 360 | -CH(CH₃)-CHF₂ (dash) | morpholine (N-linked) |
| 361 | cyclopropyl | pyrrolidine (N-linked) |
| 362 | 1-methylcyclopropyl | pyrrolidine (N-linked) |
| 363 | isopropyl | pyrrolidine (N-linked) |
| 364 | cyclopentyl | pyrrolidine (N-linked) |
| 365 | -CH(CH₃)-CH₂OH (wedge) | pyrrolidine (N-linked) |
| 366 | -CH(CH₃)-CH₂OH (dash) | pyrrolidine (N-linked) |
| 367 | -CH(CH₃)-CH₂F (wedge) | pyrrolidine (N-linked) |
| 368 | -CH(CH₃)-CH₂F (dash) | pyrrolidine (N-linked) |
| 369 | -CH(CH₃)-CHF₂ (wedge) | pyrrolidine (N-linked) |
| 370 | -CH(CH₃)-CHF₂ (dash) | pyrrolidine (N-linked) |
| 371 | cyclopropyl | 3-hydroxypyrrolidine (N-linked) |
| 372 | 1-methylcyclopropyl | 3-hydroxypyrrolidine (N-linked) |
| 373 | isopropyl | 3-hydroxypyrrolidine (N-linked) |
| 374 | cyclopentyl | 3-hydroxypyrrolidine (N-linked) |
| 375 | -CH(CH₃)-CH₂OH (wedge) | 3-hydroxypyrrolidine (N-linked) |
| 376 | -CH(CH₃)-CH₂OH (dash) | 3-hydroxypyrrolidine (N-linked) |
| 377 | -CH(CH₃)-CH₂F (wedge) | 3-hydroxypyrrolidine (N-linked) |
| 378 | -CH(CH₃)-CH₂F (dash) | 3-hydroxypyrrolidine (N-linked) |
| 379 | -CH(CH₃)-CHF₂ (wedge) | 3-hydroxypyrrolidine (N-linked) |
| 380 | -CH(CH₃)-CHF₂ (dash) | 3-hydroxypyrrolidine (N-linked) |

TABLE 4-continued

| Entry | R¹ | R² |
|---|---|---|
| 381 | cyclopropyl | N-methylpiperazinyl |
| 382 | 1-methylcyclopropyl | N-methylpiperazinyl |
| 383 | isopropyl | N-methylpiperazinyl |
| 384 | cyclopentyl | N-methylpiperazinyl |
| 385 | CH(CH₃)CH₂OH (R) | N-methylpiperazinyl |
| 386 | CH(CH₃)CH₂OH (S) | N-methylpiperazinyl |
| 387 | CH(CH₃)CH₂F (R) | N-methylpiperazinyl |
| 388 | CH(CH₃)CH₂F (S) | N-methylpiperazinyl |
| 389 | CH(CH₃)CHF₂ (R) | N-methylpiperazinyl |
| 390 | CH(CH₃)CHF₂ (S) | N-methylpiperazinyl |
| 391 | cyclopropyl | 4-methyl-4-hydroxypiperidinyl |
| 392 | 1-methylcyclopropyl | 4-methyl-4-hydroxypiperidinyl |
| 393 | isopropyl | 4-methyl-4-hydroxypiperidinyl |
| 394 | cyclopentyl | 4-methyl-4-hydroxypiperidinyl |
| 395 | CH(CH₃)CH₂OH (R) | 4-methyl-4-hydroxypiperidinyl |
| 396 | CH(CH₃)CH₂OH (S) | 4-methyl-4-hydroxypiperidinyl |
| 397 | CH(CH₃)CH₂F (R) | 4-methyl-4-hydroxypiperidinyl |
| 398 | CH(CH₃)CH₂F (S) | 4-methyl-4-hydroxypiperidinyl |
| 399 | CH(CH₃)CHF₂ (R) | 4-methyl-4-hydroxypiperidinyl |
| 400 | CH(CH₃)CHF₂ (S) | 4-methyl-4-hydroxypiperidinyl |

Representative compounds of the invention include, but are not limited to, the following compounds (Entry 401 to Entry 500 in Table 5) according to Formula (VIa), wherein R and R² are delineated for each compound in Table 5, and

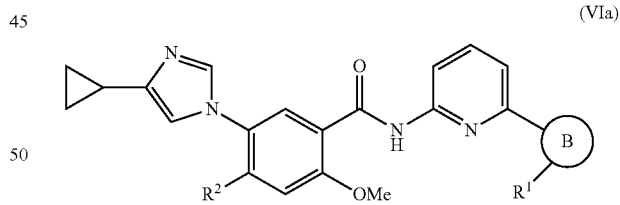

is as previously defined.

(VIa)

[Structure of Formula (VIa): 4-cyclopropyl-imidazolyl attached to a benzamide bearing R² and OMe substituents, linked via NH to a pyridine with ring B bearing R¹]

TABLE 5

| Entry | R¹ | R² |
|---|---|---|
| 401 | cyclopropyl | Me |
| 402 | 1-methylcyclopropyl | Me |

TABLE 5-continued

| Entry | R¹ | R² |
|---|---|---|
| 403 | isopropyl | Me |
| 404 | cyclopentyl | Me |
| 405 | CH(CH₃)CH₂OH (R) | Me |
| 406 | CH(CH₃)CH₂OH (S) | Me |
| 407 | CH(CH₃)CH₂F (R) | Me |
| 408 | CH(CH₃)CH₂F (S) | Me |
| 409 | CH(CH₃)CHF₂ (R) | Me |
| 410 | CH(CH₃)CHF₂ (S) | Me |
| 411 | cyclopropyl | CF₃ |
| 412 | 1-methylcyclopropyl | CF₃ |
| 413 | isopropyl | CF₃ |
| 414 | cyclopentyl | CF₃ |
| 415 | CH(CH₃)CH₂OH (R) | CF₃ |
| 416 | CH(CH₃)CH₂OH (S) | CF₃ |
| 417 | CH(CH₃)CH₂F (R) | CF₃ |
| 418 | CH(CH₃)CH₂F (S) | CF₃ |
| 419 | CH(CH₃)CHF₂ (R) | CF₃ |
| 420 | CH(CH₃)CHF₂ (S) | CF₃ |
| 421 | cyclopropyl | N(CH₃)₂ |
| 422 | 1-methylcyclopropyl | N(CH₃)₂ |
| 423 | isopropyl | N(CH₃)₂ |
| 424 | cyclopentyl | N(CH₃)₂ |
| 425 | CH(CH₃)CH₂OH (R) | N(CH₃)₂ |
| 426 | CH(CH₃)CH₂OH (S) | N(CH₃)₂ |
| 427 | CH(CH₃)CH₂F (R) | N(CH₃)₂ |
| 428 | CH(CH₃)CH₂F (S) | N(CH₃)₂ |
| 429 | CH(CH₃)CHF₂ (R) | N(CH₃)₂ |
| 430 | CH(CH₃)CHF₂ (S) | N(CH₃)₂ |

TABLE 5-continued

| Entry | R¹ | R² |
|---|---|---|
| 430 | cyclopropyl | N-azetidinyl |
| 432 | 1-methylcyclopropyl | N-azetidinyl |
| 433 | isopropyl | N-azetidinyl |
| 434 | cyclopentyl | N-azetidinyl |
| 435 | -CH(CH₃)CH₂OH (wedge) | N-azetidinyl |
| 436 | -CH(CH₃)CH₂OH (dash) | N-azetidinyl |
| 437 | -CH(CH₃)CH₂F (wedge) | N-azetidinyl |
| 438 | -CH(CH₃)CH₂F (dash) | N-azetidinyl |
| 439 | -CH(CH₃)CHF₂ (wedge) | N-azetidinyl |
| 440 | -CH(CH₃)CHF₂ (dash) | N-azetidinyl |
| 441 | cyclopropyl | N-piperidinyl |
| 442 | 1-methylcyclopropyl | N-piperidinyl |
| 443 | isopropyl | N-piperidinyl |
| 444 | cyclopentyl | N-piperidinyl |
| 445 | -CH(CH₃)CH₂OH (wedge) | N-piperidinyl |
| 446 | -CH(CH₃)CH₂OH (dash) | N-piperidinyl |
| 447 | -CH(CH₃)CH₂F (wedge) | N-piperidinyl |
| 448 | -CH(CH₃)CH₂F (dash) | N-piperidinyl |
| 449 | -CH(CH₃)CHF₂ (wedge) | N-piperidinyl |
| 450 | -CH(CH₃)CHF₂ (dash) | N-piperidinyl |
| 451 | cyclopropyl | N-morpholinyl |
| 452 | 1-methylcyclopropyl | N-morpholinyl |
| 453 | isopropyl | N-morpholinyl |
| 454 | cyclopentyl | N-morpholinyl |
| 455 | -CH(CH₃)CH₂OH (wedge) | N-morpholinyl |
| 456 | -CH(CH₃)CH₂OH (dash) | N-morpholinyl |
| 457 | -CH(CH₃)CH₂F (wedge) | N-morpholinyl |
| 458 | -CH(CH₃)CH₂F (dash) | N-morpholinyl |

TABLE 5-continued

| Entry | R¹ | R² |
|---|---|---|
| 459 | CHF₂, CH (wedge bond) | morpholine (N-O ring) |
| 460 | CHF₂, CH (dashed bond) | morpholine |
| 461 | cyclopropyl | pyrrolidine |
| 462 | 1-methylcyclopropyl | pyrrolidine |
| 463 | isopropyl | pyrrolidine |
| 464 | cyclopentyl | pyrrolidine |
| 465 | CH(CH₃)CH₂OH (wedge) | pyrrolidine |
| 466 | CH(CH₃)CH₂OH (dashed) | pyrrolidine |
| 467 | CH(CH₃)CH₂F (wedge) | pyrrolidine |
| 468 | CH(CH₃)CH₂F (dashed) | pyrrolidine |
| 469 | CH(CH₃)CHF₂ (wedge) | pyrrolidine |
| 470 | CH(CH₃)CHF₂ (dashed) | pyrrolidine |
| 471 | cyclopropyl | 3-hydroxypyrrolidine |
| 472 | 1-methylcyclopropyl | 3-hydroxypyrrolidine |
| 473 | isopropyl | 3-hydroxypyrrolidine |
| 474 | cyclopentyl | 3-hydroxypyrrolidine |
| 475 | CH(CH₃)CH₂OH (wedge) | 3-hydroxypyrrolidine |
| 476 | CH(CH₃)CH₂OH (dashed) | 3-hydroxypyrrolidine |
| 477 | CH(CH₃)CH₂F (wedge) | 3-hydroxypyrrolidine |
| 478 | CH(CH₃)CH₂F (dashed) | 3-hydroxypyrrolidine |
| 479 | CH(CH₃)CHF₂ (wedge) | 3-hydroxypyrrolidine |
| 480 | CH(CH₃)CHF₂ (dashed) | 3-hydroxypyrrolidine |
| 481 | cyclopropyl | N-methylpiperazine |
| 482 | 1-methylcyclopropyl | N-methylpiperazine |
| 483 | isopropyl | N-methylpiperazine |
| 484 | cyclopentyl | N-methylpiperazine |
| 485 | CH(CH₃)CH₂OH (wedge) | N-methylpiperazine |
| 486 | CH(CH₃)CH₂OH (dashed) | N-methylpiperazine |

TABLE 5-continued

| Entry | R¹ | R² |
|---|---|---|
| 487 | CH(CH₃)CH₂F | N-methylpiperazinyl |
| 488 | CH(CH₃)CH₂F (stereo) | N-methylpiperazinyl |
| 489 | CH(CH₃)CHF₂ | N-methylpiperazinyl |
| 490 | CH(CH₃)CHF₂ (stereo) | N-methylpiperazinyl |
| 491 | cyclopropyl | 4-hydroxy-4-methylpiperidinyl |
| 492 | 1-methylcyclopropyl | 4-hydroxy-4-methylpiperidinyl |
| 493 | isopropyl | 4-hydroxy-4-methylpiperidinyl |
| 494 | cyclopentyl | 4-hydroxy-4-methylpiperidinyl |
| 495 | CH(CH₃)CH₂OH | 4-hydroxy-4-methylpiperidinyl |
| 496 | CH(CH₃)CH₂OH (stereo) | 4-hydroxy-4-methylpiperidinyl |
| 497 | CH(CH₃)CH₂F | 4-hydroxy-4-methylpiperidinyl |
| 498 | CH(CH₃)CH₂F (stereo) | 4-hydroxy-4-methylpiperidinyl |
| 499 | CH(CH₃)CHF₂ | 4-hydroxy-4-methylpiperidinyl |
| 500 | CH(CH₃)CHF₂ (stereo) | 4-hydroxy-4-methylpiperidinyl |

Representative compounds of the invention include, but are not limited to, the following compounds (Entry 501 to Entry 600 in Table 6) according to Formula (VIb), wherein R¹ and R² are delineated for each compound in Table 6, and

is as previously defined and is not further substituted.

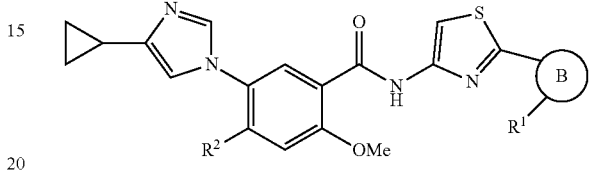

(VIb)

TABLE 6

| Entry | R¹ | R² |
|---|---|---|
| 501 | cyclopropyl | Me |
| 502 | 1-methylcyclopropyl | Me |
| 503 | isopropyl | Me |
| 504 | cyclopentyl | Me |
| 505 | CH(CH₃)CH₂OH | Me |
| 506 | CH(CH₃)CH₂OH (stereo) | Me |
| 507 | CH(CH₃)CH₂F | Me |
| 508 | CH(CH₃)CH₂F (stereo) | Me |
| 509 | CH(CH₃)CHF₂ | Me |

TABLE 6-continued

| Entry | R¹ | R² |
|---|---|---|
| 510 | CH(CHF₂)(Me), stereo | Me |
| 511 | cyclopropyl | CF₃ |
| 512 | 1-methylcyclopropyl | CF₃ |
| 513 | isopropyl | CF₃ |
| 514 | cyclopentyl | CF₃ |
| 515 | CH₂OH, CH(Me), stereo | CF₃ |
| 516 | CH₂OH, CH(Me), stereo | CF₃ |
| 517 | CH₂F, CH(Me), stereo | CF₃ |
| 518 | CH₂F, CH(Me), stereo | CF₃ |
| 519 | CH(CHF₂)(Me), stereo | CF₃ |
| 520 | CH(CHF₂)(Me), stereo | CF₃ |
| 521 | cyclopropyl | NMe₂ |
| 522 | 1-methylcyclopropyl | NMe₂ |
| 523 | isopropyl | NMe₂ |

TABLE 6-continued

| Entry | R¹ | R² |
|---|---|---|
| 524 | cyclopentyl | NMe₂ |
| 525 | CH₂OH, CH(Me), stereo | NMe₂ |
| 526 | CH₂OH, CH(Me), stereo | NMe₂ |
| 527 | CH₂F, CH(Me), stereo | NMe₂ |
| 528 | CH₂F, CH(Me), stereo | NMe₂ |
| 529 | CH(CHF₂)(Me), stereo | NMe₂ |
| 530 | CH(CHF₂)(Me), stereo | NMe₂ |
| 531 | cyclopropyl | azetidinyl |
| 532 | 1-methylcyclopropyl | azetidinyl |
| 533 | isopropyl | azetidinyl |
| 534 | cyclopentyl | azetidinyl |
| 535 | CH₂OH, CH(Me), stereo | azetidinyl |
| 536 | CH₂OH, CH(Me), stereo | azetidinyl |
| 537 | CH₂F, CH(Me), stereo | azetidinyl |

TABLE 6-continued

| Entry | R¹ | R² |
|---|---|---|
| 538 | CH₂F (S-methyl) | azetidinyl |
| 539 | CHF₂ (methyl) | azetidinyl |
| 540 | CHF₂ (S-methyl) | azetidinyl |
| 541 | cyclopropyl | piperidinyl |
| 542 | 1-methylcyclopropyl | piperidinyl |
| 543 | isopropyl | piperidinyl |
| 544 | cyclopentyl | piperidinyl |
| 545 | CH₂OH (methyl) | piperidinyl |
| 546 | CH₂OH (S-methyl) | piperidinyl |
| 547 | CH₂F (methyl) | piperidinyl |
| 548 | CH₂F (S-methyl) | piperidinyl |
| 549 | CHF₂ (methyl) | piperidinyl |
| 550 | CHF₂ (S-methyl) | piperidinyl |
| 551 | cyclopropyl | morpholinyl |
| 552 | 1-methylcyclopropyl | morpholinyl |
| 553 | isopropyl | morpholinyl |
| 554 | cyclopentyl | morpholinyl |
| 555 | CH₂OH (methyl) | morpholinyl |
| 556 | CH₂OH (S-methyl) | morpholinyl |
| 557 | CH₂F (methyl) | morpholinyl |
| 558 | CH₂F (S-methyl) | morpholinyl |
| 559 | CHF₂ (methyl) | morpholinyl |
| 560 | CHF₂ (S-methyl) | morpholinyl |
| 561 | cyclopropyl | pyrrolidinyl |
| 562 | 1-methylcyclopropyl | pyrrolidinyl |
| 563 | isopropyl | pyrrolidinyl |
| 564 | cyclopentyl | pyrrolidinyl |
| 565 | CH₂OH (methyl) | pyrrolidinyl |

TABLE 6-continued

| Entry | R¹ | R² |
|---|---|---|
| 566 | CH₂OH, CH₃ (S-config) | pyrrolidin-1-yl |
| 567 | CH₂F, CH₃ (wedge) | pyrrolidin-1-yl |
| 568 | CH₂F, CH₃ (dash) | pyrrolidin-1-yl |
| 569 | CHF₂, CH₃ (wedge) | pyrrolidin-1-yl |
| 570 | CHF₂, CH₃ (dash) | pyrrolidin-1-yl |
| 571 | cyclopropyl | 3-hydroxypyrrolidin-1-yl |
| 572 | 1-methylcyclopropyl | 3-hydroxypyrrolidin-1-yl |
| 573 | isopropyl | 3-hydroxypyrrolidin-1-yl |
| 574 | cyclopentyl | 3-hydroxypyrrolidin-1-yl |
| 575 | CH₂OH, CH₃ | 3-hydroxypyrrolidin-1-yl |
| 576 | CH₂OH, CH₃ (dash) | 3-hydroxypyrrolidin-1-yl |
| 577 | CH₂F, CH₃ (wedge) | 3-hydroxypyrrolidin-1-yl |
| 578 | CH₂F, CH₃ (dash) | 3-hydroxypyrrolidin-1-yl |
| 579 | CHF₂, CH₃ (wedge) | 3-hydroxypyrrolidin-1-yl |
| 580 | CHF₂, CH₃ (dash) | 3-hydroxypyrrolidin-1-yl |
| 581 | cyclopropyl | 4-methylpiperazin-1-yl |
| 582 | 1-methylcyclopropyl | 4-methylpiperazin-1-yl |
| 583 | isopropyl | 4-methylpiperazin-1-yl |
| 584 | cyclopentyl | 4-methylpiperazin-1-yl |
| 585 | CH₂OH, CH₃ | 4-methylpiperazin-1-yl |
| 586 | CH₂OH, CH₃ (dash) | 4-methylpiperazin-1-yl |
| 587 | CH₂F, CH₃ (wedge) | 4-methylpiperazin-1-yl |
| 588 | CH₂F, CH₃ (dash) | 4-methylpiperazin-1-yl |
| 589 | CHF₂, CH₃ (wedge) | 4-methylpiperazin-1-yl |
| 590 | CHF₂, CH₃ (dash) | 4-methylpiperazin-1-yl |
| 591 | cyclopropyl | 4-hydroxy-4-methylpiperidin-1-yl |
| 592 | 1-methylcyclopropyl | 4-hydroxy-4-methylpiperidin-1-yl |
| 593 | isopropyl | 4-hydroxy-4-methylpiperidin-1-yl |

TABLE 6-continued

| Entry | R¹ | R² |
|---|---|---|
| 594 | cyclopentyl | 4-hydroxypiperidin-1-yl |
| 595 | CH(CH₃)CH₂OH (wedge) | 4-hydroxypiperidin-1-yl |
| 596 | CH(CH₃)CH₂OH (dash) | 4-hydroxypiperidin-1-yl |
| 597 | CH(CH₃)CH₂F (wedge) | 4-hydroxypiperidin-1-yl |
| 598 | CH(CH₃)CH₂F (dash) | 4-hydroxypiperidin-1-yl |
| 599 | CH(CH₃)CHF₂ (wedge) | 4-hydroxypiperidin-1-yl |
| 600 | CH(CH₃)CHF₂ (dash) | 4-hydroxypiperidin-1-yl |

In certain embodiments, the present invention provides a method for the prevention or treatment of an ASK-1 mediated disease or condition. The method comprises administering a therapeutically effective amount of a compound of Formula (I). The present invention also provides the use of a compound of Formula (I) for the preparation of a medicament for the treatment of an ASK-1 mediated disease or condition.

In certain embodiments, the ASK-1 mediated disease or condition is an autoimmune disorder, a neurodegenerative disorder, an inflammatory disease, chronic kidney disease, renal disease, cardiovascular disease, a metabolic disease, or an acute or chronic liver disease.

In certain embodiments, the chronic liver disease is primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, or alpha 1-antitrypsin deficiency. In certain embodiments, the gastrointestinal disease is inflammatory bowel disease (IBD) (including Crohn's disease and ulcerative colitis), irritable bowel syndrome (IBS), bacterial overgrowth, malabsorption, post-radiation colitis, or microscopic colitis.

In certain embodiments, the renal disease is diabetic nephropathy, focal segmental glomerulosclerosis (FSGS), hypertensive nephrosclerosis, chronic glomerulonephritis, chronic transplant glomerulopathy, chronic interstitial nephritis, or polycystic kidney disease.

In certain embodiments, the cardiovascular disease is atherosclerosis, arteriosclerosis, reperfusion/ischemia in stroke, cardiac hypertrophy, respiratory diseases, heart attacks, myocardial ischemia.

In certain embodiments, the metabolic disease is insulin resistance, Type I and Type II diabetes, or obesity.

In certain embodiments, the chronic kidney disease is polycystic kidney disease, pyelonephritis, kidney fibrosis and glomerulonephritis.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "alkyl" as used herein, refers to saturated, straight- or branched-chain hydrocarbon radicals. "$C_1$-$C_3$ alkyl," "$C_1$-$C_6$ alkyl," "$C_1$-$C_{10}$ alkyl" "$C_2$-$C_4$ alkyl," or "$C_3$-$C_6$ alkyl," refer to alkyl groups containing from one to three, one to six, one to ten carbon atoms, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_{10}$ alkenyl," "$C_2$-$C_8$ alkenyl," "$C_2$-$C_4$ alkenyl," or "$C_3$-$C_6$ alkenyl," refer to alkenyl groups containing from two to ten, two to eight, two to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon triple bond by the removal of a single hydrogen atom. "$C_2$-$C_{10}$ alkynyl," "$C_2$-$C_8$ alkynyl," "$C_2$-$C_4$ alkynyl," or "$C_3$-$C_6$ alkynyl," refer to alkynyl groups containing from two to ten, two to eight, two to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic, iminic or oximic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo [2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic, iminic or oximic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted. The term "bicyclic aryl" or "bicyclic heteroaryl" refers to a ring system consisting of two rings wherein at least one ring is aromatic; and the two rings can be fused or covalently attached.

As used herein, the term "arylalkyl" means a functional group wherein an alkylene chain is attached to an aryl group, e.g., —CH$_2$CH$_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

The term "alkylene" as used herein, refers to a diradical of a branched or unbranched saturated hydrocarbon chain, typically having from 1 to 20 carbon atoms (e.g. 1-10 carbon atoms, or 1, 2, 3, 4, 5, or 6 carbon atoms). This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like.

The term "substituted" as used herein, refers to independent replacement of one, two, or three or more of the hydrogen atoms thereon with substituents including, but not limited to, deuterium, —F, —Cl, —Br, —I, —OH, protected hydroxy, —NO$_2$, —CN, —NH$_2$, N$_3$, protected amino, alkoxy, thioalkoxy, oxo, $C_1$-$C_6$-alkyl, $C_2$-$C_{12}$-alkenyl, $C_2$-$C_{12}$-alkynyl, -halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH— heteroaryl, —CONH-heterocycloalkyl, —OCO$_2$—$C_1$-$C_{12}$-alkyl, —OCO$_2$—$C_2$-$C_{12}$-alkenyl, —OCO$_2$—$C_2$-$C_{12}$-alkynyl, —OCO$_2$—$C_3$-$C_{12}$-cycloalkyl, —OCO$_2$-aryl, —OCO$_2$-heteroaryl, —OCO$_2$-heterocycloalkyl, —OCONH$_2$, —OCONH—$C_1$-$C_{12}$-alkyl, —OCONH—$C_2$-$C_{12}$-alkenyl, —OCONH—$C_2$-$C_{12}$-alkynyl, —OCONH—$C_3$-$C_{12}$-cycloalkyl, —OCONH-aryl, —OCONH— heteroaryl, —OCONH— heterocycloalkyl, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)-heterocycloalkyl, —NHCO$_2$—$C_1$-$C_{12}$-alkyl, —NHCO$_2$—$C_2$-$C_{12}$-alkenyl, —NHCO$_2$—$C_2$-$C_{12}$-alkynyl, —NHCO$_2$—$C_3$-$C_{12}$-cycloalkyl, —NHCO$_2$-aryl, —NHCO$_2$-heteroaryl, —NHCO$_2$-heterocycloalkyl, —NHC(O)NH$_2$, —NHC(O)NH—$C_1$-$C_{12}$-alkyl, —NHC(O)NH—$C_2$-$C_{12}$-alkenyl, —NHC(O)NH—$C_2$-$C_{12}$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH$_2$, —NHC(S)NH—$C_1$-$C_{12}$-alkyl, —NHC(S)NH—$C_2$-$C_{12}$-alkenyl, —NHC(S)NH—$C_2$-$C_{12}$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkynyl, —S(O)—$C_3$-$C_{12}$-cycloalkyl, —S(O)-aryl, —S(O)-heteroaryl, —S(O)-heterocycloalkyl-SO$_2$NH$_2$, —SO$_2$NH—$C_1$-$C_{12}$-alkyl, —SO$_2$NH—$C_2$-$C_{12}$-alkenyl, —SO$_2$NH—$C_2$-$C_{12}$-alkynyl, —SO$_2$NH—$C_3$-$C_{12}$-cycloalkyl, —SO$_2$NH-aryl, —SO$_2$NH-heteroaryl, —SO$_2$NH-heterocycloalkyl, —NHSO$_2$—$C_1$-$C_{12}$-alkyl, —NHSO$_2$—$C_2$-$C_{12}$-alkenyl, —NHSO$_2$—$C_2$-$C_{12}$-alkynyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkynyl, —S—$C_3$-$C_{12}$-cycloalkyl, —S-aryl, —S-heteroaryl, —S-heterocycloalkyl, methylthiomethyl, or -L'-R', wherein L' is $C_1$-$C_6$alkylene, $C_2$-$C_6$alkenylene or $C_2$-$C_6$alkynylene, and R' is aryl, heteroaryl, heterocyclic, $C_3$-$C_{12}$cycloalkyl or $C_3$-$C_{12}$cycloalkenyl. It is understood that the aryls, heteroaryls, alkyls, and the like can be further substituted. In some cases, each substituent in a substituted moiety is additionally optionally substituted with one or more groups, each group being independently selected from $C_1$-$C_6$-alkyl, —F, —Cl, —Br, —I, —OH, —NO$_2$, —CN, or —NH$_2$.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic" as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, and bicyclo[2.2.2]octyl. Such alicyclic groups may be further substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

The term "aryloxy" refers to the group aryl-O— wherein the aryl group is as defined above and includes optionally substituted aryl groups as also defined above. The term "arylthio" refers to the group R—S—, where R is as defined for aryl.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic, iminic or oximic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, cycloalkyl, heterocyclic and cycloalkenyl moiety described herein can also be an aliphatic group or an alicyclic group.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloaklylene, cycloalkenylene, cycloalkynylene, arylalkylene, heteroarylalkylene and heterocycloalkylene groups are to be included in the above definitions and are applicable to provide the Formulas herein with proper valency.

The terms "halo" and "halogen," as used herein, refer to an atom selected from fluorine, chlorine, bromine and iodine.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus, a carbon-carbon double bond or carbon-heteroatom double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

Berge, et al. describes pharmaceutically acceptable salts in detail in J. Pharmaceutical Sciences, 66: 1-19 (1977). The salts can be prepared in situ during the final isolation and purification of the compounds of the invention, or separately by reaction of the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, esters of $C_1$-$C_6$-alkanoic acids, such as acetate, propionate, butyrate and pivalate esters.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992) and in "Prodrugs of Alcohols and Phenols" by S. S. Dhareshwar and V. J. Stella, in *Prodrugs Challenges and Rewards Part-2,* (Biotechnology: Pharmaceutical Aspects), edited by V. J. Stella, et al, Springer and AAPSPress, 2007, pp 31-99.

The term "amino" as used herein, refers to the group —$NH_2$.

The term "substituted amino" as used herein, refers to the group —NRR where each R is independently selected from the group consisting of hydrogen, alkyl, cycloalkyl, aryl, heteroaryl and heterocycloalkyl provided that both R groups are not hydrogen, or a group —Y—Z, in which Y is optionally substituted alkylene and Z is alkenyl, cycloalkenyl, or alkynyl.

The term "amino protecting group" as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the Formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed). "Design and Application of Prodrugs, *Textbook of Drug Design and Development*, Chapter 5, 113-191 (1991); Bundgaard, et al., *Journal of Drug Deliver Reviews*, 8:1-38(1992); Bundgaard, *J. of Pharmaceutical Sciences,* 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

The term "treating", as used herein, means relieving, lessening, reducing, eliminating, modulating, or ameliorating, i.e. causing regression of the disease state or condition. Treating can also include inhibiting, i.e. arresting the development, of an existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired isoxazole products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention Formulated together with one or more pharmaceutically acceptable carriers. As used herein, the term "pharmaceutically acceptable carrier" means a non-toxic, inert solid, semi-solid or liquid filler, diluent, encapsulating material or Formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the Formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the Formulation may be adjusted with pharmaceutically acceptable acids, bases or buffers to enhance the stability of the Formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1, 3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable Formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable Formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragées, capsules, pills, and granules can be prepared with coatings and shells such as enteric coatings, release controlling coatings and other coatings well known in the pharmaceutical Formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic Formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
BOP-Cl for bis(2-oxo-3-oxazolidinyl)phosphinic chloride;
CDI for carbonyldiimidazole;
DBU for 1,8-diazabicycloundec-7-ene;
DCC for N,N-dicyclohexylcarbodiimide;
DCM for dichloromethane;
DIPEA for N,N-diisopropylethylamine;
DMAP for N,N-dimethylaminopyridine;
DME for 1,2-dimethoxyethane;
DMF for N,N-dimethyl formamide;
DMPU for 1,3-Dimethyl-3,4,5,6-tetrahydro-2(1H)-pyrimidinone;
EDC for 1-(3-diethylaminopropyl)-3-ethylcarbodiimide hydrochloride;
$Et_3N$ for triethylamine;
EtOAc for ethyl acetate;
HATU for 1-[bis(dimethylamino)methylene]-1H-1,2,3-triazolo[4,5-b]pyridinium 3-oxid hexafluorophosphate;
HCl for hydrochloric acid;
mCPBA for meta-chloroperoxybenzoic acid;
NMO for N-methylmorpholine-N-oxide;
PhMe for toluene;
PyAOP for 7-azabenzotriazol-1-yloxy)tripyrrolidino-phosphonium hexafluorophosphate;
PyBOP for benzotriazol-1-yl-oxytripyrrolidinophosphonium hexafluorophosphate;
THE for tetrahydrofuran.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

As shown in Scheme 1, the compound of Formula (I) can be prepared from coupling of the carboxylic acid compound (1) and the amine compound (2) under suitable amide coupling conditions, wherein, R, $R^2$, $R^3$, $X^1$, and

are as previously defined. For the preparation of carboxylic acid compound (1), see US2016/0244430. Thus, a mixture of carboxylic acid compound (1) and amine compound (2) in an aprotic solvent is treated with suitable coupling reagent in the presence of organic base to form amide compound of Formula (I). The suitable coupling reagent can be, such as, but not limited to, BOP-Cl, CDI, DCC, EDC, HATU, PyAOP or PyBOP and the organic base can be, such as, but not limited to, $Et_3N$, DIPEA, pyridine or N-methyl morpholine. The aprotic solvent can be, such as, but not limited to, THF, DCM and DMF. The reaction temperature is from −20° C. to 80° C.

Scheme 1

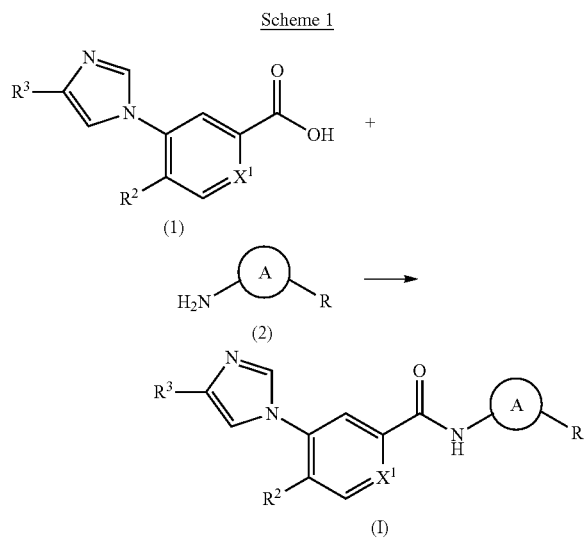

Alternatively, the compound of Formula (I) can also be prepared by first converting carboxylic acid compound (1) to an acid chloride compound (3) and then reacting acid chloride compound (3) with amine compound (2) in the presence of an organic base (as shown in scheme 2).

Scheme 2

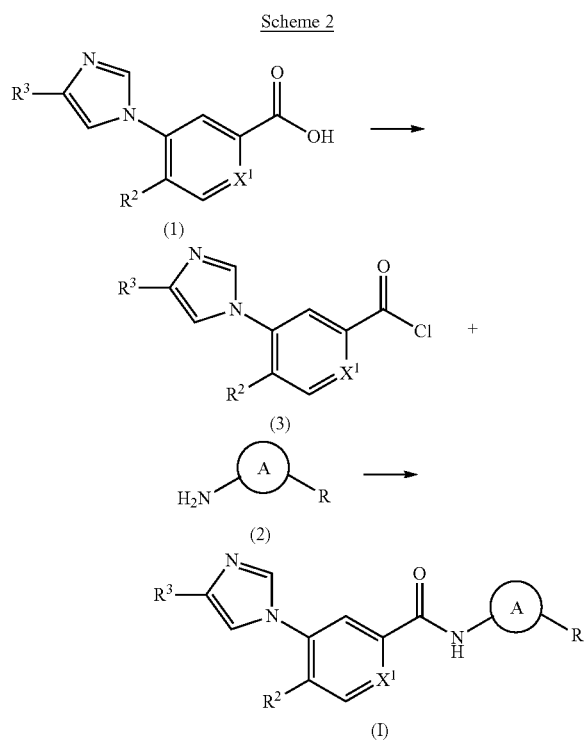

Thus, the carboxylic acid compound (1) is treated with thionyl chloride or oxalyl chloride or other acid chloride formation reagent in an aprotic solvent, such as, but not limited to DCM or DMF to afford an acid chloride compound (3). Then, the acid chloride compound (3) is reacted with the amine compound (2) in an aprotic solvent, such as, but not limited to DCM or DMF in the presence of an organic base, such as, but not limited to TEA, DIPEA. DMAP or pyridine to give the compound of Formula (I).

Another alternative way to prepare the compound of Formula (I) is by first converting carboxylic acid compound (1) to mixed anhydride compound (4) and then reacting mixed anhydride compound (4) with amine compound (2) in the presence of organic base (as shown in scheme 3).

Scheme 3

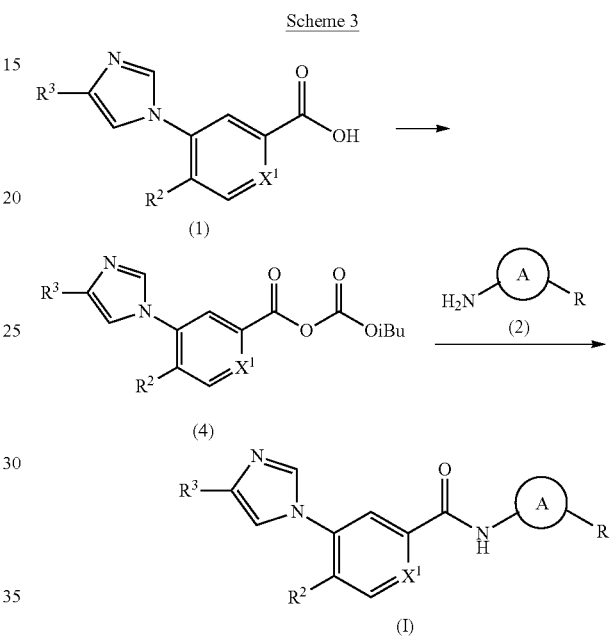

Thus, the carboxylic acid compound (1) is treated with a chloroformate reagent such as, but not limited to isobutyl-cloroformate in an aprotic solvent, such as, but not limited to DCM in the presence of a base such as, but not limited to TEA or DIPEA to afford mixed anhydride compound (4). Then, the mixed anhydride compound (4) is reacted with the amine compound (2) in an aprotic solvent, such as, but not limited to DCM or DMF in the presence of an organic base, such as, but not limited to TEA, DIPEA. DMAP to give the compound of Formula (I).

Scheme 4 to Scheme 6 illustrate the synthesis of tetrazole compound (2a). Scheme 7 illustrates the synthesis of tetrazole compound (2b). A more detailed discussion of the tetrazole synthesis is described in literature, for example, by Cheng-Xi Wei, Ming Bian and Guo-Hua Gong, *Molecules*, 2015, 20, 5528-5553.

As shown in Scheme 4, the tetrazole compound (6a) is prepared by [3+2] cycloaddition between hydrazoic acid and nitrile compound (5a). Thus, the compound (5a) is treated with $NaN_3$ or $TMSN_3$ in a solvent such as, but not limited to DMF in the presence of Lewis acid in high temperature to afford compound (6a). The said Lewis acid can be, but not limited to ammonium chloride, $Bu_3SnO$. The reaction temperature is from 50° C.~150° C. The compound (6a) is further alkylated with RX, where $R^1$ is as defined previously, preferably optionally substituted alkyl, and X is halogen, preferably chlorine or bromine or iodine, in the presence of a base to give the compound (2a).

Scheme 4

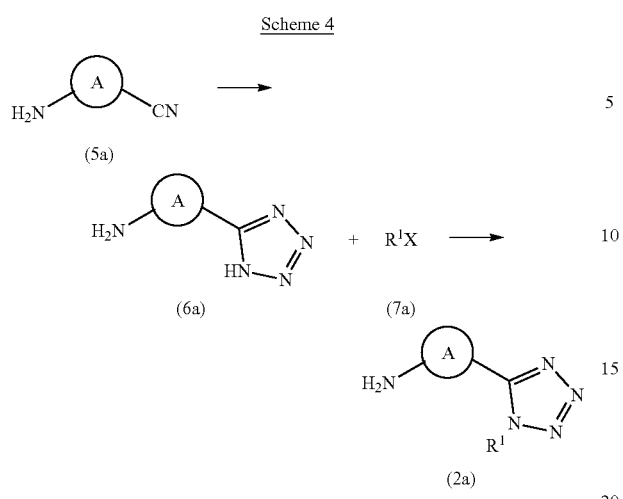

An alternative procedure to prepare the compound (2a) is shown in scheme (5). The tetrazole compound (9a) is synthesized by the reaction of amine compound (8a) with triethyl orthoformate and sodium azide in acetic acid. The compound (9a) is further coupled with compound (10a), where X is halogen, preferably chlorine or bromine or iodine, to give the compound (2a). The solvent in this coupling reaction can be, but not limited to 1, 4-dioxane. The catalyst used in this reaction can be, but not limited to bis(triphenylphosphine)palladium(II) chloride. The base used in this reaction can be, but is not limited to, cesium carbonate. The reaction temperature is from 0° C.~50° C.

Scheme 5

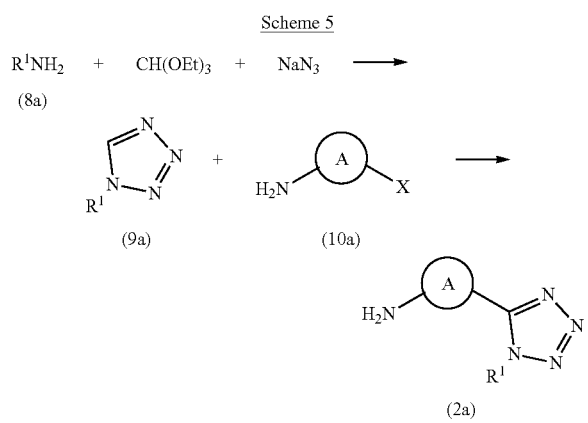

Another alternative procedure to prepare the compound (2a) is shown in scheme (6). The compound (12a) can be prepared by coupling of carboxylic acid compound (11a) with amine compound (8a). Thus, a mixture of carboxylic acid compound (11a) and amine compound (8a) in an aprotic solvent is treated with suitable coupling reagent in the presence of organic base to form amide compound (12a). The suitable coupling reagent can be, such as, but not limited to, BOP-Cl, CDI, DCC, EDC, HATU, PyAOP or PyBOP and the organic base can be, such as, but not limited to, Et$_3$N, DIPEA, pyridine or N-methyl morpholine. The aprotic solvent can be, such as, but not limited to, THF, DCM and DMF. The reaction temperature is from –20° C. to 80° C. Then the amide compound (12a) is further converted to tetrazole compound (13a) by treating with sodium azide and trifluoromethanesulfonic anhydride in an aprotic solvent. Such aprotic solvent can be, but not limited to acetonitrile. The reaction temperature is from –20° C. to 50° C.

Scheme 6

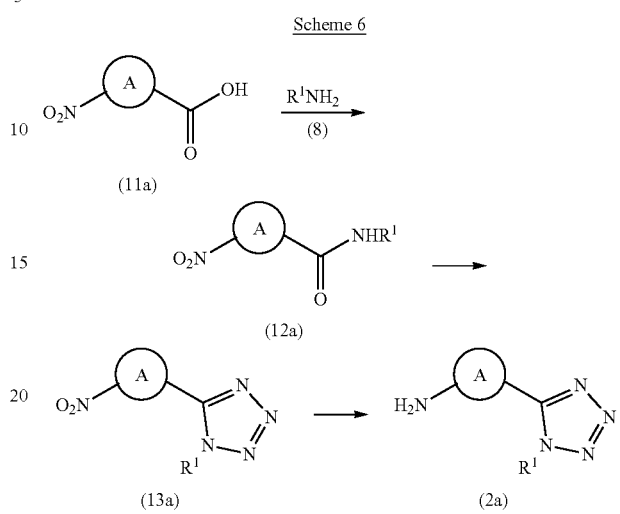

As shown in Scheme 7, the diamine compound (5a) was protected with P group to afford compound (6b). P can be any amine protecting group such as, but not limited to Cbz, Boc and PMB. A more detailed discussion of the procedures, reagents and conditions for protection of amine group is described in literature, for example, by T. W. Greene and P. G. M. Wuts in "*Protective Groups in Organic Synthesis*" 3$^{rd}$ ed., John Wiley & Son, Inc., 1999. The compound (8b) can be prepared by coupling of the resulting amine compound (6b) with carboxylic acid compound (7b). Thus, a mixture of carboxylic acid compound (7b) and amine compound (6b) in an aprotic solvent is treated with a suitable coupling reagent in the presence of organic base to form amide compound (8b). The suitable coupling reagent can be, such as, but not limited to, BOP-Cl, CDI, DCC, EDC, HATU, PyAOP or PyBOP and the organic base can be, such as, but not limited to, Et$_3$N, DIPEA, pyridine or N-methyl morpholine. The aprotic solvent can be, such as, but not limited to, THF, DCM and DMF. The reaction temperature is from –20° C. to 80° C. Then the amide compound (8b) is further converted to tetrazole compound (9b) by treating with phosphorus pentachloride and trimethylsilyl azide in an aprotic solvent. Such aprotic solvent can be, but not limited to acetonitrile and dichloroethane. The reaction temperature is from –20° C. to 60° C. Then deprotection of P group provides tetrazole compound (2b). A more detailed discussion of the procedures, reagents and conditions for deprotection of amine protecting groups is described in literature, for example, by T. W. Greene and P. G. M. Wuts in "*Protective Groups in Organic Synthesis*" 3rd ed., John Wiley & Son, Inc., 1999.

Scheme 7

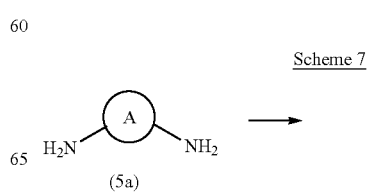

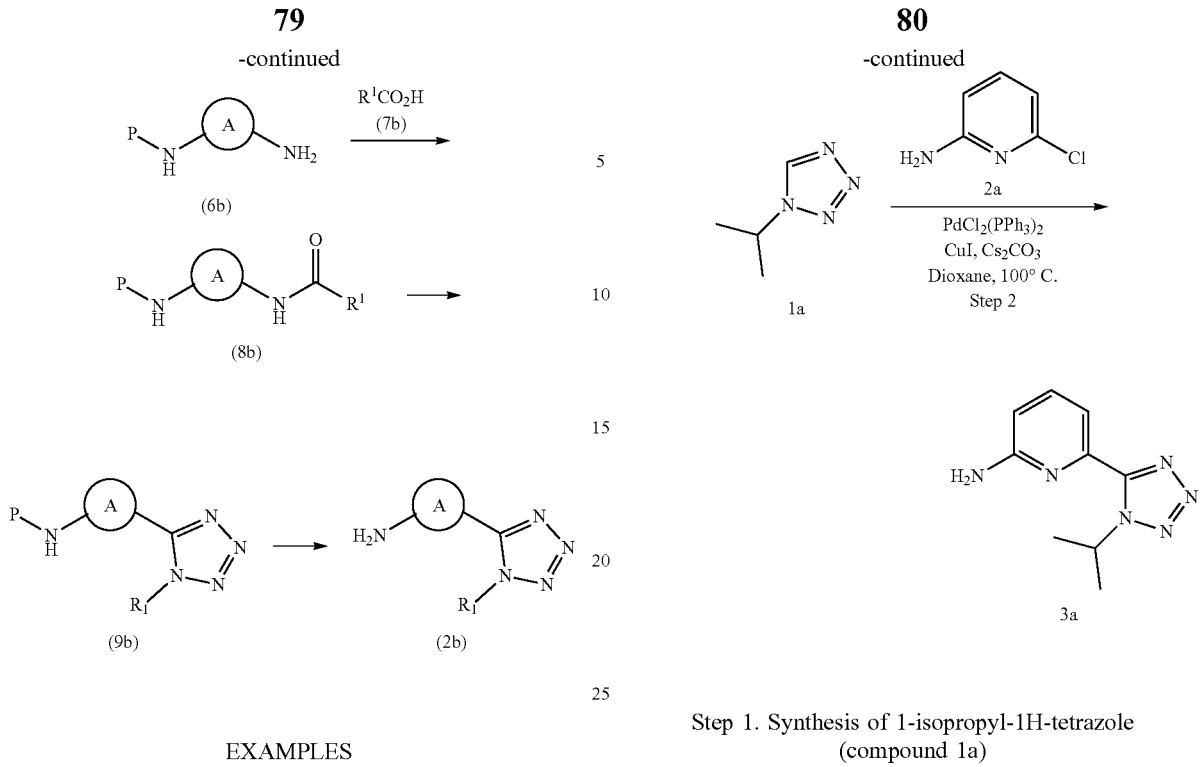

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, Formulations and/or methods of the invention may be made without departing from the spirit of the invention and the scope of the appended claims.

Synthesis of 6-(1-isopropyl-1H-tetrazol-5-yl)pyridin-2-amine (Compound 3a)

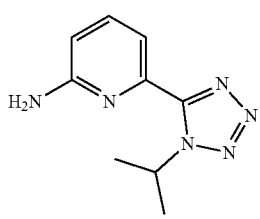

Route 1:

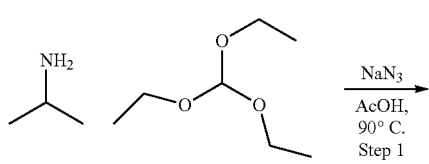

Step 1. Synthesis of 1-isopropyl-1H-tetrazole (compound 1a)

A solution of propan-2-amine (3.44 mL, 40 mmol), sodium azide (3.64 g, 56 mmol) and triethyl orthoformate (9.31 mL, 56.0 mmol) in acetic acid (20 mL) was heated to 90° C. and stirred for 1 d behind a blast shield. The reaction mixture was then cooled down to rt, diluted with EtOAc. The mixture was washed with 1N HCl, sat. $NaHCO_3$ (×3) and brine, dried over $Na_2SO_4$, filtered and concentrated under vacuum to give the desired product as a pale yellow oil (1.52 g, 34%). $^1$H NMR (400 MHz, Chloroform-d) δ 8.62 (s, 1H), 4.90 (p, J=6.7 Hz, 1H), 1.68 (d, J=6.7 Hz, 6H).

Step 2. Synthesis of 6-(1-isopropyl-1H-tetrazol-5-yl)pyridin-2-amine (compound 3a)

A mixture of 1-isopropyl-1H-tetrazole (560 mg, 4.99 mmol), 6-chloropyridin-2-amine (2a) (642 mg, 4.99 mmol), copper(I) iodide (47.6 mg, 0.250 mmol), bis(triphenylphosphine)-palladium(II) chloride (351 mg, 0.499 mmol), and cesium carbonate (3254 mg, 9.99 mmol) in 1,4-dioxane (20 mL) was degassed and heated to 100° C., and stirred for 24 h behind a blast shield. The reaction was cooled down to rt, and then diluted with EtOAc and water. The aqueous layer was extracted with EtOAc, and the combined organic layers were washed with brine, dried over $Na_2SO_4$, filtered and concentrated. The residue was purified by chromatography on silica gel using hexane/acetone (100/0 to 50/50, 15 min) to give compound 3a as a pale yellow solid (330 mg, 32%). MS (m/z): 205.10 [M+H]$^+$. $^1$H NMR (400 MHz, Chloroform-d) δ 7.75-7.60 (m, 2H), 6.66 (dd, J=7.3, 1.8 Hz, 1H), 5.87 (dq, J=13.4, 6.7 Hz, 1H), 4.62 (s, 2H), 1.68 (d, J=6.7 Hz, 6H).

Route 2:

Step 1: Synthesis of
N-isopropyl-6-nitropicolinamide (compound 5a)

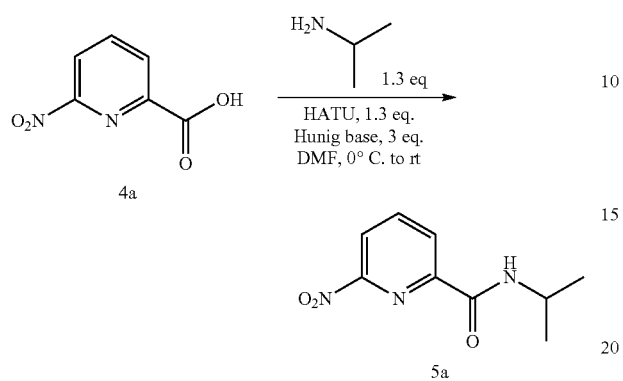

To a solution of 6-nitropicolinic acid (10 g, 59.5 mmol) and Hunig's base (31.1 mL, 178 mmol, 3 eq.) in dry DMF (200 mL) at 0° C. was added isopropylamine (6.64 mL, 77 mmol, 1.3 eq) followed by addition of HATU (29.4 g, 77 mmol, 1.3 eq.) The resulting mixture was allowed to warm to rt and stirred for several hours before it was quenched by addition of water (500 mL). The mixture was extracted with EtOAc (3×200 mL) and the combined organic layers were washed with water (2×200 mL), brine (200 mL), dried (Na$_2$SO$_4$) and concentrated. The residue was purified by SiO$_2$ column chromatography (80 g column, 100% hexanes to 40% EtOAc/Hexanes) to afford compound N-isopropyl-6-nitropicolinamide (10.81 g, 87% yield) as a light yellow solid. $^1$H NMR (400 MHz, Chloroform-d) δ 8.58 (dd, J=7.7, 1.0 Hz, 1H), 8.36 (dd, J=8.0, 1.0 Hz, 1H), 8.21 (t, J=7.8 Hz, 1H), 7.70 (s, 1H), 4.31 (hept, J=6.6 Hz, 1H), 1.32 (d, J=6.6 Hz, 6H).

Step 2: Synthesis of 2-(1-isopropyl-1H-tetrazol-5-yl)-6-nitropyridine (compound 6a)

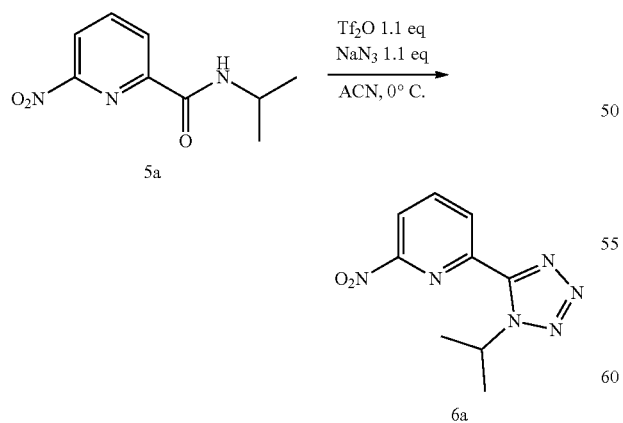

To a mixture of N-isopropyl-6-nitropicolinamide (350 mg, 1.673 mmol) and sodium azide (120 mg, 1.840 mmol) in anhydrous acetonitrile (5.58 mL) under N$_2$ at 0° C. behind a blast shield was added dropwise trifluoromethanesulfonic anhydride (1M solution in DCM, 1.84 mL, 1.840 mmol). The resulting mixture was stirred at 0° C. for 1 h and then rt for 2 hrs. The reaction was then cooled to 0° C. and quenched with sat. NaHCO$_3$ (50 mL). The mixture was extracted with EtOAc 2×. The combined organic layers were washed with sat. NaHCO$_3$ and brine, and concentrated. The residue dark red solid was purified by SiO$_2$ chromatography (12 g column, 100% hexanes to 35% EtOAc/Hexanes) to give compound 6a (170 mg, 43% yield) as a colorless solid. $^1$H NMR (400 MHz, Chloroform-d) δ 8.74 (dd, J=7.7, 0.9 Hz, 1H), 8.41 (dd, J=8.1, 0.9 Hz, 1H), 8.32 (t, J=7.9 Hz, 1H), 5.95 (hept, J=6.7 Hz, 1H), 1.72 (d, J=6.7 Hz, 6H).

Step 3: Synthesis of 6-(1-isopropyl-1H-tetrazol-5-yl)pyridin-2-amine (compound 3a)

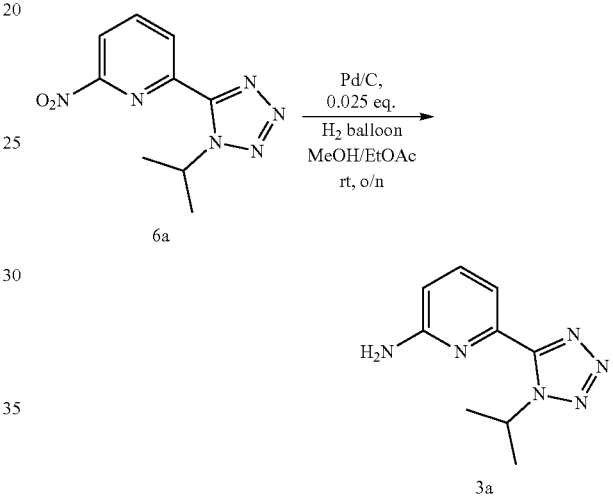

A mixture of 2-(1-isopropyl-1H-tetrazol-5-yl)-6-nitropyridine (100 mg, 0.427 mmol) and Pd/C (10% Pd on dry base, contained 50% water, 23 mg, 0.025 eq) in MeOH (1 mL)/EtOAc (1 mL) was stirred at rt under a H$_2$ balloon overnight. The catalyst was then filtered and the filtrate was concentrated to provide compound 3a (85 mg, 97% yield), which was used directly in the next step without further purification. MS (m/z): 163.05 [M+H]$^+$. $^1$H NMR (400 MHz, Chloroform-d) δ 7.72-7.54 (m, 2H), 6.63 (dd, J=7.4, 1.7 Hz, 1H), 5.85 (hept, J=6.7 Hz, 1H), 4.57 (s, 2H), 1.65 (d, J=6.7 Hz, 6H).

Route 3:

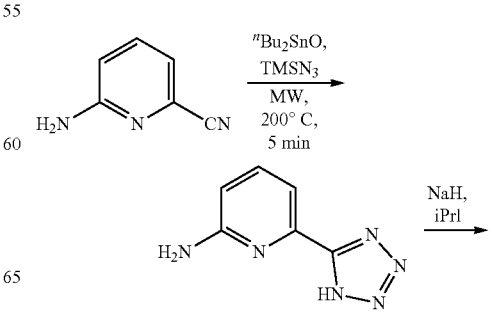

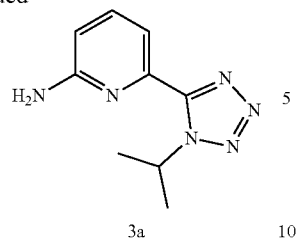

3a

A reaction mixture of 6-aminopicolinonitrile (542 mg, 4.55 mmol), dibutyltin oxide (566 mg, 2.275 mmol), Toluene (10 mL), and azidotrimethylsilane (1.812 mL, 13.65 mmol) was stirred at 200° C. under microwave irradiation for 5 min. TLC showed a complete reaction. The yellow suspension was filtered, washed with toluene, dried in vacuo to give a yellow powder 6-(1H-tetrazol-5-yl)pyridin-2-amine (1.2 g, quan. yield). $^1$H & $^{13}$C NMR showed the product containing dibutyltin oxide which will not affect next step reaction. MS (m/z): 205.10 [M+H]$^+$. $^1$H NMR (400 MHz, DMSO-d$_6$) δ 7.67 (t, J=7.9 Hz, 1H), 7.36 (d, J=7.2 Hz, 1H), 6.71 (d, J=8.4 Hz, 1H), 6.57 (s, 2H).

To a 50 mL 2-necked round-bottomed flask were added 6-(1H-tetrazol-5-yl)pyridin-2-amine (300 mg, 1.850 mmol), DMF (9.250 mL) and the solution was cooled to 0° C. followed by addition of sodium hydride (133 mg, 3.33 mmol). Bubbling was observed. After stirred at 0° C. for 20 min, 2-iodopropane (0.333 mL, 3.33 mmol) was added and the rxn was stirred at 0° C.~rt for 9 h. Cooled the reaction mixture to 0° C., quenched with water (~30 mL). Extracted with DCM (~70 mL), washed with brine. Dried, filtered, concentrated, purified by CombiFlash (24 g SiO$_2$, MeOH/DCM=0-100%) to give 6-(1-isopropyl-1H-tetrazol-5-yl)pyridin-2-amine as a white solid (24 mg, 6.35% yield). MS (m/z): 205.10 [M+H]$^+$.

Synthesis of 6-(1-cyclopropyl-1H-tetrazol-5-yl)pyridin-2-amine (compound 7a)

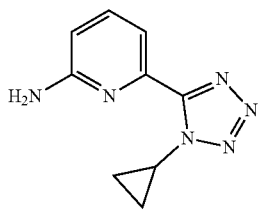

7a

Compound 7a was prepared by using similar procedure as described for compound 3a following route 2. $^1$H NMR (400 MHz, DMSO-d$_6$) δ 7.61 (dd, J=8.4, 7.3 Hz, 1H), 7.29 (dd, J=7.3, 0.8 Hz, 1H), 6.65 (dd, J=8.4, 0.9 Hz, 1H), 6.38 (s, 2H), 4.79 (m, 1H), 1.33-1.12 (m, 4H). Synthesis of 6-(1-(1-methylcyclopropyl)-1H-tetrazol-5-yl)pyridin-2-amine (compound 8a):

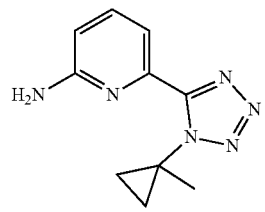

8a

Compound 8a was prepared by using similar procedure as described for compound 3a following route 2. $^1$H NMR (400 MHz, DMSO-d$_6$) δ 7.59 (dd, J=8.4, 7.3 Hz, 1H), 7.18 (dd, J=7.3, 0.8 Hz, 1H), 6.64 (dd, J=8.4, 0.9 Hz, 1H), 6.29 (s, 2H), 1.72 (s, 3H), 1.12 (m, 4H).

Example 1a: 5-(4-cyclopropyl-1H-imidazol-1-yl)-2-fluoro-N-(6-(1-isopropyl-1H-tetrazol-5-yl)pyridin-2-yl)-4-methylbenzamide

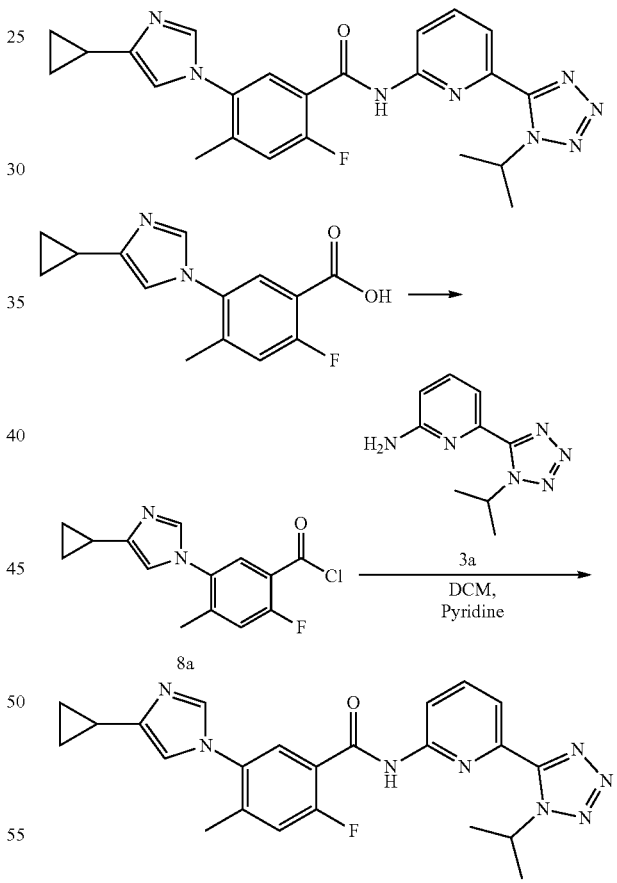

Example 1a

To a suspension of 5-(4-cyclopropyl-1H-imidazol-1-yl)-2-fluoro-4-methylbenzoic acid (382 mg, 1.469 mmol) in DCM (20 ml) was added 1-chloro-N,N,2-trimethylprop-1-en-1-amine (Ghosez's reagent, 0.324 mL, 2.448 mmol). The reaction mixture was stirred at rt for 40 min to form a clear solution and then concentrated in vacuo. The residue (compound 8a) was taken into DCM (40.0 mL) and cooled down to 0° C., and a solution of 6-(1-isopropyl-H-tetrazol-5-yl) pyridin-2-amine (3a) (250 mg, 1.224 mmol) and pyridine (0.594 ml, 7.34 mmol) in DCM (20 mL) was added. The reaction mixture was allowed to warm up to rt and stirred for 4 hrs. The mixture was concentrated, and then diluted with EtOAc and brine. The aqueous layer was extracted with EtOAc. The combined organic layers were dried over $Na_2SO_4$ and concentrated. The residue was purified by chromatography on silica gel using hexane/acetone/MeOH (100/0/0 to 50/40/10, 15 min) to give compound of example 1a as white foam (440 mg, 81%). LC-MS (m/z): M−1=445.18, calcd. 445.20; M+1=447.20, calcd. 447.20. $^1$H NMR (400 MHz, DMSO-$d_6$) δ 11.08 (s, 1H), 8.34-8.26 (m, 1H), 8.14 (t, J=8.0 Hz, 1H), 8.05-7.97 (m, 1H), 7.73-7.63 (m, 2H), 7.51 (d, J=10.7 Hz, 1H), 7.19 (d, J=1.5 Hz, 1H), 6.00 (p, J=6.7 Hz, 1H), 2.26 (s, 3H), 1.84 (m, 1H), 1.56 (d, J=6.6 Hz, 6H), 0.86-0.76 (m, 2H), 0.70-0.68 (m, 2H).

Example 2a: 5-(4-cyclopropyl-1H-imidazol-1-yl)-2-fluoro-N-(6-(1-cyclopropyl-1H-tetrazol-5-yl)pyridin-2-yl)-4-methylbenzamid

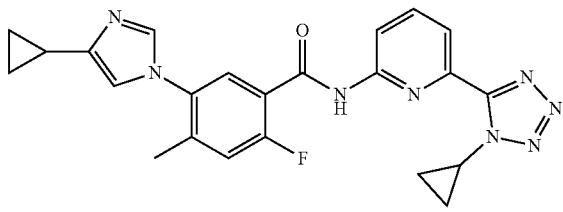 [SMILES: Cc1cc(F)c(C(=O)Nc2cccc(-c3nnnn3C3CC3)n2)cc1-n1cnc(C2CC2)c1]

Example 2a was prepared from compound 7a by using similar procedure as described for compound of Example 1a. LC-MS (m/z): M−1=443.17, calcd. 443.18. $^1$H NMR (400 MHz, DMSO-$d_6$) δ 11.09 (s, 1H), 8.35 (dd, J=8.4, 0.9 Hz, 1H), 8.15 (dd, J=8.4, 7.6 Hz, 1H), 7.98 (dd, J=7.6, 0.9 Hz, 1H), 7.72-7.62 (m, 2H), 7.50 (d, J=10.8 Hz, 1H), 7.18 (d, J=1.4 Hz, 1H), 4.86 (m, 1H), 2.25 (s, 3H), 1.85 (m, 1H), 1.32-1.12 (m, 4H), 0.85-0.74 (m, 2H), 0.74-0.66 (m, 2H).

Example 3a: 5-(4-cyclopropyl-1H-imidazol-1-yl)-2-fluoro-N-(6-(1-(1-methylcyclo-propyl)-1H-tetrazol-5-yl)pyridin-2-yl)-4-methylbenzamide

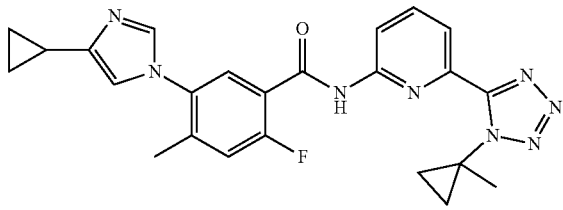 [SMILES: Cc1cc(F)c(C(=O)Nc2cccc(-c3nnnn3C3(C)CC3)n2)cc1-n1cnc(C2CC2)c1]

Example 3a was prepared from compound 8a by using similar procedure as described for compound of Example 1a. LC-MS (m/z): M−1=457.19, calcd. 457.20. H NMR (400 MHz, DMSO-$d_6$) δ 10.75 (s, 1H), 8.36 (dd, J=8.4, 0.9 Hz, 1H), 8.14 (dd, J=8.4, 7.6 Hz, 1H), 7.86 (dd, J=7.6, 0.9 Hz, 1H), 7.73-7.65 (m, 2H), 7.49 (d, J=11.1 Hz, 1H), 7.19 (d, J=1.3 Hz, 1H), 2.25 (s, 3H), 1.85 (m, 1H), 1.74 (s, 3H), 1.15 (q, J=2.6 Hz, 4H), 0.87-0.77 (m, 2H), 0.73-0.67 (m, 2H).

Example 4a: (S)-2-(5-(6-(5-(4-cyclopropyl-1H-imidazol-1-yl)-2-fluoro-4-methyl-benzamido)pyridin-2-yl)-1H-tetrazol-1-yl)propyl acetate

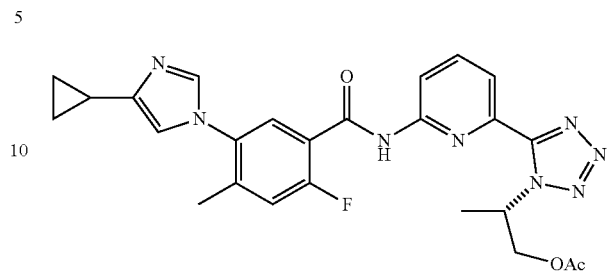

Step 1: Synthesis of (S)-2-(tert-butoxycarbonylamino) propyl acetate

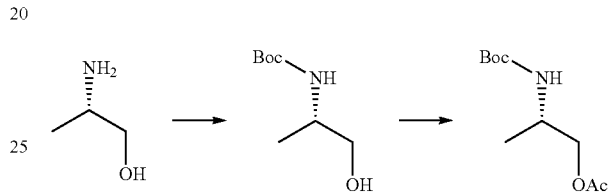

To (S)-2-aminopropan-1-ol (2.1 g, 28.0 mmol) in DCM (60 ml) was added $BOC_2O$ (9.74 ml, 41.9 mmol) at 0° C. The mixture was stirred at 0° C. for 30 min, then allowed to warm up to room temperature and stirred for 16 h. The mixture was concentrated to give tert-butyl (S)-(1-hydroxypropan-2-yl)carbamate as colorless oil. $^1$H NMR (400 MHz, Chloroform-d) δ 4.64 (s, 1H), 3.77 (s, 1H), 3.64 (dd, J=11.0, 3.8 Hz, 1H), 3.51 (dd, J=11.0, 6.2 Hz, 1H), 1.45 (s, 9H), 1.27 (s, 1H), 1.15 (d, J=6.8 Hz, 3H).

To the crude tert-butyl (S)-(1-hydroxypropan-2-yl)carbamate was added DCM (60 ml), sodium carbonate (5.93 g, 55.9 mmol) followed by acetyl chloride (3.18 ml, 44.7 mmol) and the mixture was stirred at room temperature for 4 h. The mixture was filtered through celite and the filtrate was concentrated. The residue was diluted with ethyl acetate, washed with $NaHCO_3$ solution, NaOH solution, water and brine. The organic layer was dried, filtered and concentrated to give (S)-2-((tert-butoxycarbonyl)amino) propyl acetate (5.61 g, 92%) as colorless oil. $^1$H NMR (400 MHz, Chloroform-d) δ 4.57 (s, 1H), 4.06-3.86 (m, 3H), 2.08 (s, 3H), 1.45 (s, 9H), 1.16 (d, J=6.7 Hz, 3H).

Step 2: Synthesis of (S)-2-(6-nitropicolinamido) propyl acetate

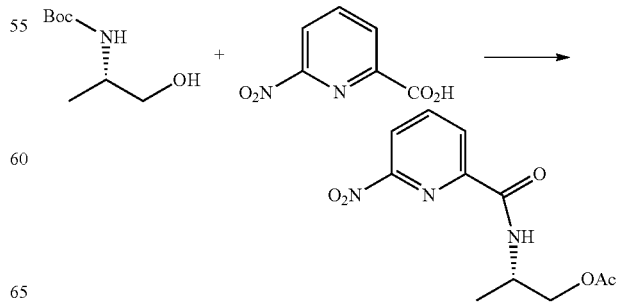

To a suspension of 6-nitropicolinic acid (200 mg, 1.190 mmol) in DCM (3 ml) and one drop of DMF was added oxalyl chloride (0.714 ml, 1.428 mmol, 2 M in DCM) dropwise. The resulting mixture was stirred at room temperature for 2 h to give a clear solution. The solution was concentrated under vacuum and chased with DCM to give 6-nitropicolinoyl chloride as yellow solid. To a separate flask charged with (S)-2-((tert-butoxycarbonyl)amino)propyl acetate (388 mg, 1.785 mmol) in DCM (2 ml) was added TFA (2 ml) and the mixture was stirred at room temperature for 2 h. The mixture was concentrated and chased with DCM to give the TFA salt of (S)-2-aminopropan-1-ol.

To the freshly prepared 6-nitropicolinoyl chloride was added DCM (0.5 ml) followed by the TFA salt (S)-2-aminopropan-1-ol in DCM (2 ml) and triethylamine (0.497 ml, 3.57 mmol) dropwise at 0° C. The mixture was warmed up to room temperature and for 16 h. The mixture was concentrated and the residue was purified by CombiFlash eluting with hexane to 70% ethyl acetate in hexane to give (S)-2-(6-nitropicolinamido)propyl acetate (175 mg, 55%). $^1$H NMR (400 MHz, Chloroform-d) δ 8.58 (dd, J=7.6, 1.0 Hz, 1H), 8.39 (dd, J=8.1, 1.0 Hz, 1H), 8.23 (dd, J=8.8, 6.9 Hz, 1H), 7.93 (d, J=8.8 Hz, 1H), 4.59-4.39 (m, 1H), 4.21 (qd, J=11.3, 5.0 Hz, 2H), 2.11 (d, J=3.4 Hz, 3H), 1.36 (d, J=6.9 Hz, 3H).

Step 3: Synthesis of (S)-2-(5-(6-nitropyridin-2-yl)-1H-tetrazol-1-yl) propyl acetate

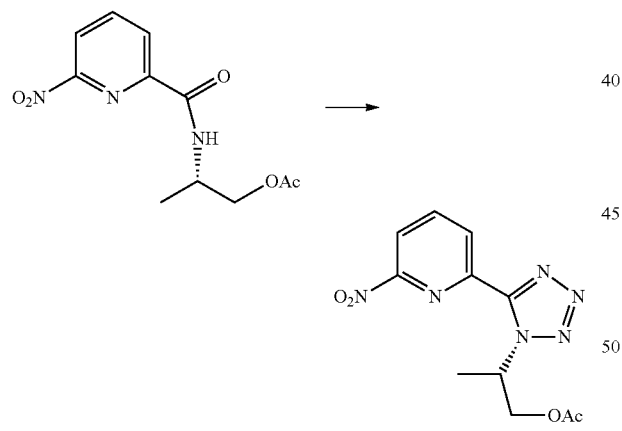

To (S)-2-(6-nitropicolinamido)propyl acetate (175 mg, 0.655 mmol) and sodium azide (68.1 mg, 1.048 mmol) in acetonitrile (3 ml) at 0° C. was added triflic anhydride (0.982 ml, 0.982 mmol, 1M in DCM) dropwise. The resulting mixture was stirred for 30 min then warmed up to room temperature and stirred for 1 h. The mixture was diluted with ethyl acetate, quenched with NaHCO$_3$ solution. The organic layer was separated, washed with brine, dried, filtered and concentrated. The residue was purified by CombiFlash eluting with hexane to 60% ethyl acetate in hexane to afford (S)-2-(5-(6-nitropyridin-2-yl)-1H-tetrazol-1-yl)propyl acetate (148 mg, 0.506 mmol, 77% yield) as yellow oil. $^1$H NMR (400 MHz, Chloroform-d) δ 8.79 (dd, J=7.7, 0.9 Hz, 1H), 8.43 (dd, J=8.1, 1.0 Hz, 1H), 8.33 (t, J=7.9 Hz, 1H), 6.17 (td, J=7.1, 4.6 Hz, 1H), 4.62 (qd, J=11.8, 6.1 Hz, 2H), 1.89 (s, 3H), 1.82 (d, J=6.9 Hz, 3H).

Step 4: Synthesis of (S)-2-(5-(6-aminopyridin-2-yl)-1H-tetrazol-1-yl)propyl acetate

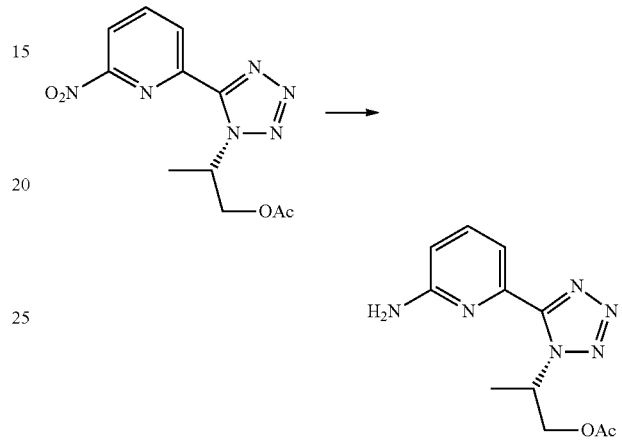

To (S)-2-(5-(6-nitropyridin-2-yl)-1H-tetrazol-1-yl)propyl acetate (40 mg, 0.137 mmol) in ethanol (0.8 ml) and acetic acid (0.8 ml) was added iron (76 mg, 1.369 mmol) and the resulting mixture was stirred at 90° C. for 2 h. The mixture was filtered through celite and the filtrate was concentrated, chased with DCM. The residue was purified by CombiFlash eluting with hexane to 70% ethyl acetate in Hexane to give (S)-2-(5-(6-aminopyridin-2-yl)-1H-tetrazol-1-yl)propyl acetate (28 mg, 0.107 mmol, 78% yield). $^1$H NMR (400 MHz, Chloroform-d) δ 7.85-7.48 (m, 2H), 6.62 (dd, J=8.0, 1.1 Hz, 1H), 6.30 (m, 1H), 4.96-4.58 (m, 3H), 4.32 (dd, J=11.4, 9.5 Hz, 1H), 1.85 (s, 3H), 1.68 (d, J=7.0 Hz, 3H).

Step 5: Synthesis of (S)-2-(5-(6-(5-(4-cyclopropyl-1H-imidazol-1-yl)-2-fluoro-4-methyl-benzamido)pyridin-2-yl)-1H-tetrazol-1-yl)propyl acetate (Example 4a)

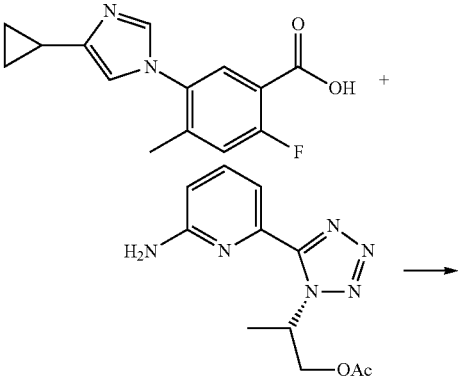

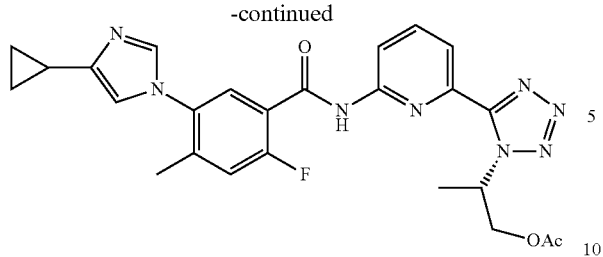

Example 4a

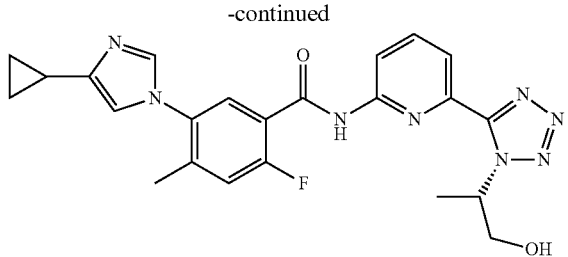

Example 5a

To 5-(4-cyclopropyl-1H-imidazol-1-yl)-2-fluoro-4-methylbenzoic acid (33.3 mg, 0.128 mmol) in DCM (1.5 ml) was added one drop of DMF and oxalyl chloride (0.080 ml, 0.160 mmol, 2 M in DCM). The suspension was stirred at room temperature for 45 min and turned into a clear solution. The mixture was concentrated and chased with DCM. To this residue was added (S)-2-(5-(6-aminopyridin-2-yl)-1H-tetrazol-1-yl)propyl acetate (28 mg, 0.107 mmol) in DCM (1.5 ml) and pyridine (0.043 ml, 0.534 mmol). The mixture was stirred at RT for 16 h and concentrated. The residue was diluted with ethyl acetate, washed with water, brine, dried, filtered and concentrated. The residue was purified by CombiFlash eluting with hexane to 10% MeOH in ethyl acetate to afford (S)-2-(5-(6-(5-(4-cyclopropyl-1H-imidazol-1-yl)-2-fluoro-4-methylbenzamido)pyridin-2-yl)-1H-tetrazol-1-yl)propyl acetate (36 mg, 0.071 mmol, 66.8% yield). LC/MS observed [M+H], 505.20; $^1$H NMR (400 MHz, Chloroform-d) δ 9.18 (d, J=9.9 Hz, 1H), 8.41 (dd, J=8.4, 0.9 Hz, 1H), 8.02 (dd, J=7.6, 0.9 Hz, 1H), 7.95-7.73 (m, 2H), 7.36 (d, J=1.4 Hz, 1H), 7.11 (d, J=11.6 Hz, 1H), 6.69 (d, J=1.4 Hz, 1H), 6.07 (dqd, J=9.2, 6.9, 4.7 Hz, 1H), 4.55 (dd, J=11.4, 4.8 Hz, 1H), 4.29 (dd, J=11.4, 9.2 Hz, 1H), 2.18 (s, 3H), 1.80 (tt, J=8.3, 5.1 Hz, 1H), 1.69 (s, 3H), 1.61 (d, J=6.9 Hz, 3H), 0.83-0.69 (m, 4H).

Example 5a: (S)-5-(4-cyclopropyl-1H-imidazol-1-yl)-2-fluoro-N-(6-(1-(1-hydroxypropan-2-yl)-1H-tetrazol-5-yl)pyridin-2-yl)-4-methylbenzamide

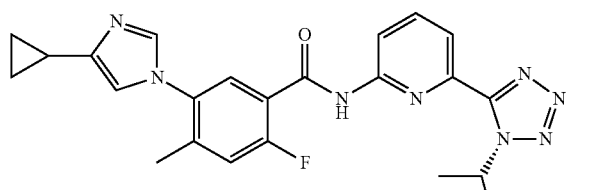

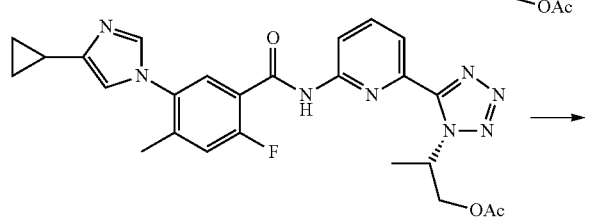

To (S)-2-(5-(6-(5-(4-cyclopropyl-1H-imidazol-1-yl)-2-fluoro-4-methylbenzamido)pyridin-2-yl)-1H-tetrazol-1-yl)propyl acetate (26 mg, 0.052 mmol) in MeOH (1 ml) was added LiOH (0.077 ml, 0.077 mmol, 1 N in water) and the resulting mixture was stirred at room temperature for 30 min. The mixture was concentrated and the residue was purified by CombiFlash eluting with hexane to 10% MeOH in ethyl acetate to give (S)-5-(4-cyclopropyl-1H-imidazol-1-yl)-2-fluoro-N-(6-(1-(1-hydroxypropan-2-yl)-1H-tetrazol-5-yl)pyridin-2-yl)-4-methylbenzamide (19.5 mg, 0.042 mmol, 82% yield). LC/MS observed [M+H], 463.19; $^1$H NMR (400 MHz, Chloroform-d) δ 9.14 (d, J=15.7 Hz, 1H), 8.45 (dd, J=8.3, 0.9 Hz, 1H), 8.18-7.91 (m, 3H), 7.45 (d, J=1.5 Hz, 1H), 7.25-7.16 (m, 1H), 6.80 (d, J=1.5 Hz, 1H), 5.71 (dddd, J=11.0, 7.8, 6.9, 4.1 Hz, 1H), 4.14-4.06 (m, 2H), 2.30 (s, 3H), 1.91 (tt, J=8.3, 5.1 Hz, 1H), 1.70 (d, J=6.8 Hz, 3H), 1.00-0.73 (m, 4H).

Example 6a: (R)-2-(5-(6-(5-(4-cyclopropyl-1H-imidazol-1-yl)-2-fluoro-4-methyl-benzamido)pyridin-2-yl)-1H-tetrazol-1-yl)propyl acetate

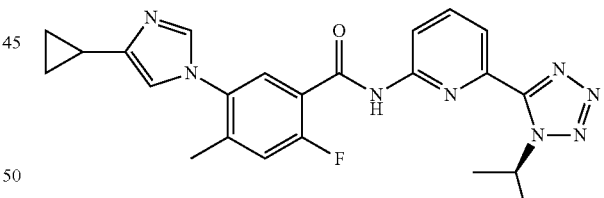

Example 6a was prepared by using similar procedure as described for compound of Example 4a. LC/MS observed [M+H], 505.20; $^1$H NMR (500 MHz, Chloroform-d) δ 9.62-9.38 (m, 2H), 8.38 (d, J=8.3 Hz, 1H), 8.07 (d, J=7.5 Hz, 1H), 8.02-7.98 (m, 1H), 7.92 (t, J=8.0 Hz, 1H), 7.21 (d, J=10.0 Hz, 1H), 6.85 (s, 1H), 6.21 (d, J=10.3 Hz, 1H), 4.57 (dd, J=11.6, 4.2 Hz, 1H), 4.33 (dd, J=11.4, 8.8 Hz, 1H), 2.30 (s, 3H), 1.97 (s, 1H), 1.73 (s, 3H), 1.65 (d, J=6.7 Hz, 3H), 1.10-0.87 (m, 4H).

Example 7a: (R)-5-(4-cyclopropyl-1H-imidazol-1-yl)-2-fluoro-N-(6-(1-(1-hydroxypropan-2-yl)-1H-tetrazol-5-yl)pyridin-2-yl)-4-methylbenzamide

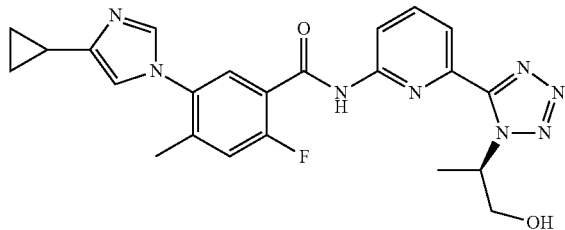 [SMILES: Cc1cc(F)c(C(=O)Nc2cccc(-c3nnnn3[C@H](C)CO)n2)cc1-n1cnc(C2CC2)c1]

Example 7a was prepared by using similar procedure as described for compound of Example 5a. LC/MS observed [M+H], 463.19; H NMR (400 MHz, Chloroform-d) δ 9.13 (d, J=14.8 Hz, 1H), 8.34 (dd, J=8.4, 0.9 Hz, 1H), 8.08-7.95 (m, 2H), 7.90 (t, J=8.0 Hz, 1H), 7.46 (d, J=1.4 Hz, 1H), 7.12 (d, J=12.2 Hz, 1H), 6.71 (d, J=1.4 Hz, 1H), 5.82-5.52 (m, 1H), 4.15-3.88 (m, 2H), 2.21 (s, 3H), 1.82 (tt, J=8.3, 5.1 Hz, 1H), 1.59 (d, J=6.8 Hz, 3H), 0.87-0.69 (m, 4H).

Example 19a

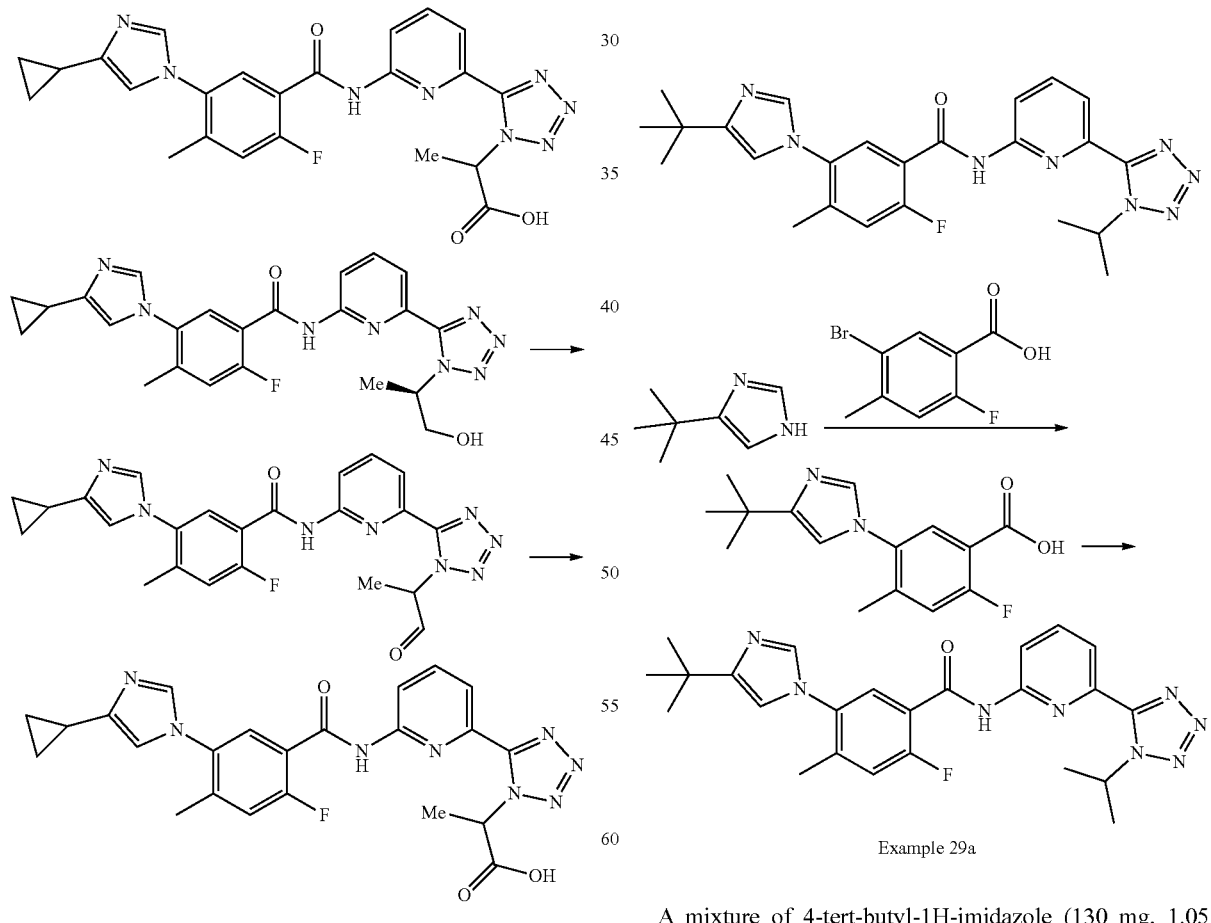

To a solution of (R)-5-(4-cyclopropyl-1H-imidazol-1-yl)-2-fluoro-N-(6-(1-(1-hydroxypropan-2-yl)-1H-tetrazol-5-yl) pyridin-2-yl)-4-methylbenzamide (681 mg, 1.47 mmol) in DCM (7.3 mL) at 0° C. was added Dess-Martin periodinane (750 mg, 1.77 mmol). The reaction was allowed to stir at 0° C. for 1 hour, quenched with saturated aq. $Na_2S_2O_3$ solution and extracted with DCM (×3). The combined DCM layers were washed by brine, dried over $Na_2SO_4$, filtered and concentrated. The resulting white solid was directly used in the following transformation without any purification.

To a suspension of previous crude (36 mg, 0.075 mmol)), 2-methylbute-2-ene (2.0 M in THF, 0.19 mL) and $NaH_2PO_4$ (13.5 mg, 0.113 mmol) in tBuOH/$H_2O$ (0.8 mL, 4/1) was added $NaClO_2$ (34 mg, 0.3 mmol). The reaction was allowed to stir at rt for 3 hours, quenched with 20% Citric acid aq. solution and extracted with EtOAc (×3). The combined EtOAc layers were washed by brine, dried over $Na_2SO_4$, filtered and concentrated. The residue was purified by chromatography on silica gel (0→10% MeOH in DCM) to provide Example 19a as white solid (12.8 mg, 36% yield). LC/MS observed [M+1]: 477.17. $^1$H NMR (400 MHz, DMSO-$d_6$) δ 11.08 (s, 1H), 8.26 (d, J=8.3 Hz, 1H), 8.08 (t, J=8.0 Hz, 1H), 7.92 (d, J=7.6 Hz, 1H), 7.72 (d, J=1.4 Hz, 1H), 7.67 (d, J=6.4 Hz, 1H), 7.48 (d, J=10.7 Hz, 1H), 7.21 (s, 1H), 6.02 (s, br, 1H), 2.26 (s, 3H), 1.89-1.83 (m, 1H), 1.78 (d, J=7.2 Hz, 3H), 0.80 (dt, J=8.4, 3.1 Hz, 2H), 0.73-0.68 (m, 2H).

Example 29a

Example 29a

A mixture of 4-tert-butyl-1H-imidazole (130 mg, 1.05 mmol), 5-bromo-2-fluoro-4-methylbenzoic acid (200 mg, 0.86 mmol), $Cu_2O$ (7 mg, 0.04 mmol), 8-hydroxyquinoline (25 mg, 0.17 mmol), and $K_3PO_4$ (912 mg, 4.3 mmol) in DMSO (10 mL) was stirred at 100° C. for 16 h. The reaction was cooled to rt, quenched with 60 mL of water, adjusted to pH 5 by 8M HCl, and extracted with EtOAc (50 mL×2). The organic layer was dried over saturated $Na_2SO_4$ and evaporated. Purification of the residue by Prep-HPLC with 0-100% $MeCN/H_2O$ provided 100 mg (42.2%) of 5-(4-tert-butyl-1H-imidazol-1-yl)-2-fluoro-4-methylbenzoic acid as white solid. A mixture of 5-(4-tert-butyl-1H-imidazol-1-yl)-2-fluoro-4-methylbenzoic acid (60 mg, 0.22 mmol) and (1-chloro-2-methylprop-1-en-1-yl)dimethylamine (36 mg, 0.27 mmol) in DCM (2 mL) was stirred for 1 h at room temperature. To the above mixture was added pyridine (52 mg, 0.66 mmol), and 6-(1-isopropyl-1H-tetrazol-5-yl)pyridin-2-amine (68 mg, 0.33 mmol). The resulting mixture was stirred for additional 1 h at room temperature. Solvent was removed under vacuum and the residue was purified by reverse phase chromatography with 0-60% $MeCN/H_2O$ to give Example 29a (8.4 mg) as a white solid.

Example 30a

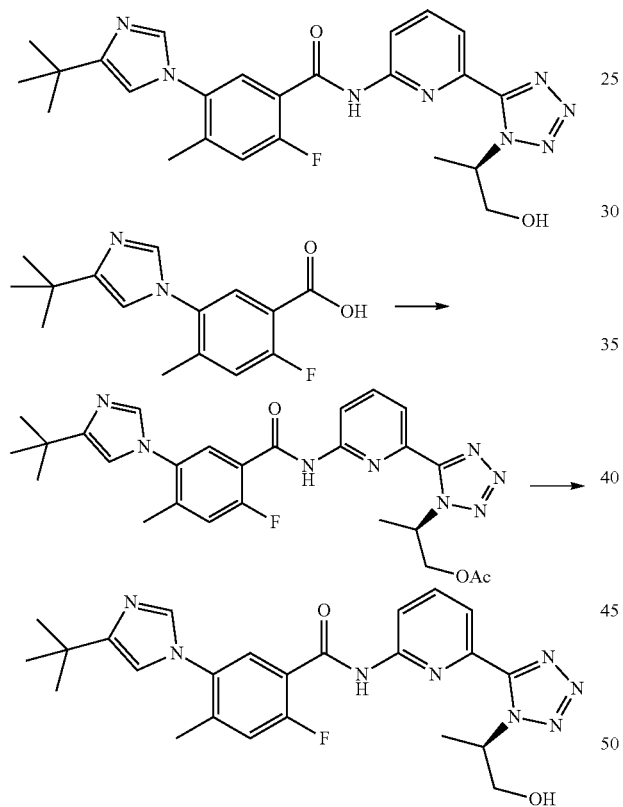

Example 30a

A mixture of 5-(4-tert-butyl-1H-imidazol-1-yl)-2-fluoro-4-methylbenzoic acid (60 mg, 0.22 mmol) and (1-chloro-2-methylprop-1-en-1-yl)dimethylamine (36 mg, 0.27 mmol) in DCM (2 mL) was stirred for 1 h at room temperature. To the above mixture was added pyridine (52 mg, 0.66 mmol), and (R)-2-(5-(6-aminopyridin-2-yl)-1H-tetrazol-1-yl)propylacetate (87 mg, 0.33 mmol). The resulting mixture was stirred for additional 1 h at room temperature. Solvent was removed under vacuum and the residue was purified by reverse phase chromatography with 0-60% $MeCN/H_2O$ to provide (R)-2-(5-(6-(5-(4-tert-butyl-1H-imidazol-1-yl)-2-fluoro-4-methylbenzamido)pyridin-2-yl)-1H-tetrazol-1-yl)

propyl acetate (50 mg, 44%) as a white solid. $K_2CO_3$ (73 mg, 0.53 mmol) was added to a solution of (R)-2-(5-(6-(5-(4-tert-butyl-1H-imidazol-1-yl)-2-fluoro-4-methylbenzamido)pyridin-2-yl)-1H-tetrazol-1-yl)propyl acetate (50 mg, 0.096 mmol) in MeOH (5 mL). The resulting mixture was stirred for 2 hours at room temperature. The reaction was concentrated and the crude product was purified by Prep-HPLC with 0-100% $MeCN/H_2O$ to provide 16.3 mg of Example 30 as a white solid.

Example 27a was prepared following a similar protocol as Example 29a.

Example 28a was prepared following a similar protocol as Example 30a.

Example 31a

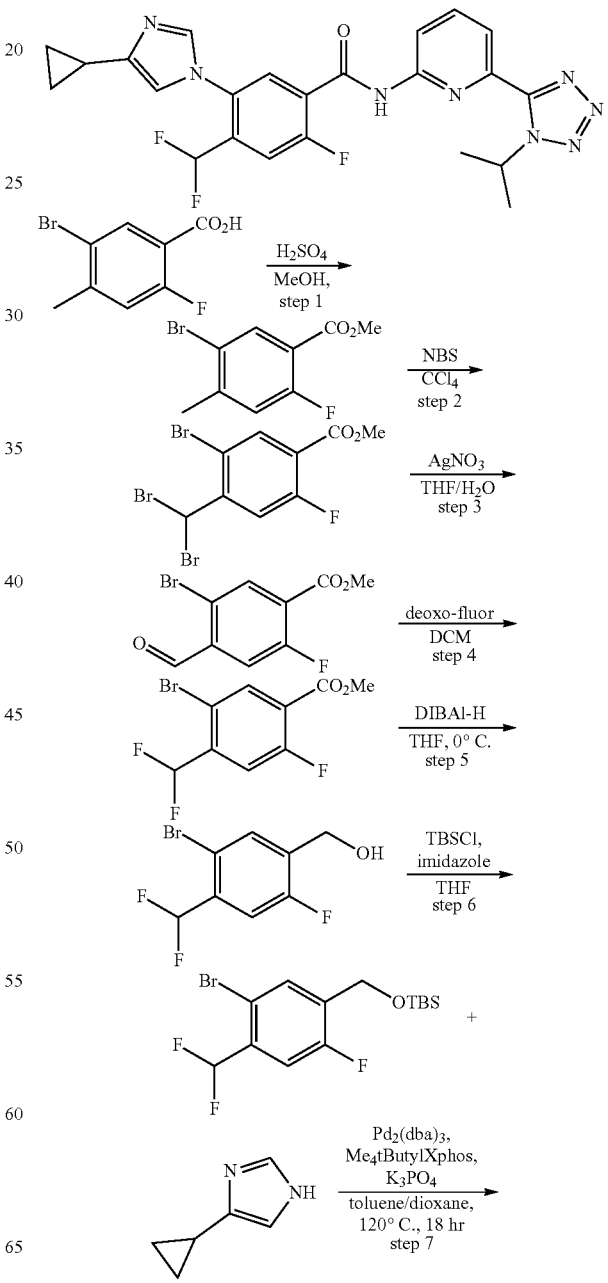

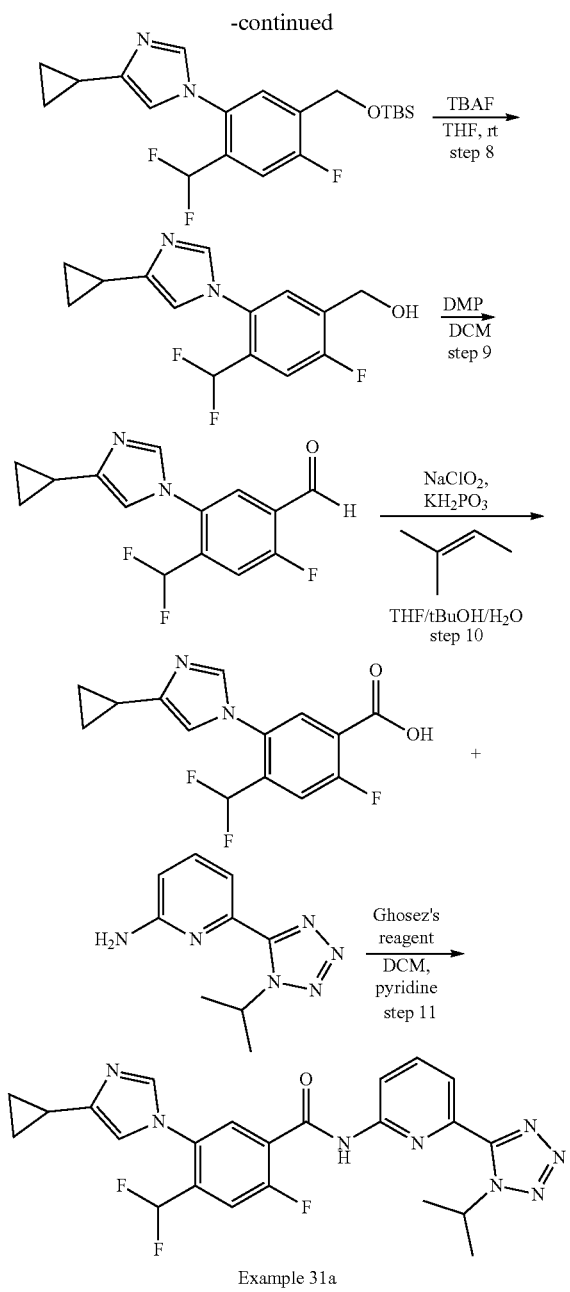

Example 31a

Step 1: synthesis of methyl 5-bromo-2-fluoro-4-methylbenzoate

To a suspension of 5-bromo-2-fluoro-4-methylbenzoic acid (5 g, 21.46 mmol) in MeOH (7 mL) was dropwise added conc. sulfuric acid (0.114 mL, 2.15 mmol). The resulting solution was allowed to stir at reflux until completion. The reaction was then cooled to rt and concentrated. The crude was dissolved in EtOAc and basified by aq. NaHCO$_3$. The aqueous layer was extracted with EtOAc (×3). The combined EtOAc layers were washed by brine and dried over Na$_2$SO$_4$. Filtration and concentration afforded methyl 5-bromo-2-fluoro-4-methylbenzoate as white solid (4.06 g, 77% yield). $^1$H NMR (400 MHz, Chloroform-d) δ 8.09 (d, J=6.9 Hz, 1H), 7.04 (d, J=11.0 Hz, 1H), 3.92 (s, 3H), 2.43 (s, 3H).

Step 2: synthesis methyl 5-bromo-4-(dibromomethyl)-2-fluorobenzoate

To a solution of methyl 5-bromo-2-fluoro-4-methylbenzoate (3.13 g, 12.67 mmol) in CCl$_4$ (40 mL) was added NBS (6.76 g, 38 mmol) and benzoyl peroxide (0.307 g, 1.27 mmol). The reaction was allowed to stir at 90° C. for overnight. The crude was cooled to rt and filtered through a short Celite plug and washed with TBME twice. The filtrate was then concentrated and purified by chromatography on silica gel (0→10% EtOAc in hexanes) to afford methyl 5-bromo-4-(dibromomethyl)-2-fluorobenzoate as colorless oil (4.86 g, 95% yield). $^1$H NMR (400 MHz, Chloroform-d) δ 8.10 (d, J=6.6 Hz, 1H), 7.82 (d, J=10.9 Hz, 1H), 6.94 (d, J=1.2 Hz, 1H), 3.95 (s, 3H).

Step 3: synthesis of methyl 5-bromo-2-fluoro-4-formylbenzoate

To a suspension of methyl 5-bromo-4-(dibromomethyl)-2-fluorobenzoate (4.86 g, 12.0 mmol) in THF/water (3/1, 60 mL) was added AgNO$_3$ (6.12 g, 36 mmol). The reaction was allowed to stir at 80° C. for 2 hours. The crude reaction was quenched with water and was extracted with EtOAc (×3). The combined EtOAc layers were washed by brine, dried over Na$_2$SO$_4$, filtered and concentrated. The residue was purified by chromatography on silica gel (0→20% EtOAc in hexanes) to provide methyl 5-bromo-2-fluoro-4-formylbenzoate as white solid (2.76 g, 88% yield). $^1$H NMR (400 MHz, Chloroform-d) δ 10.32 (d, J=2.7 Hz, 1H), 8.23 (d, J=6.1 Hz, 1H), 7.68 (d, J=10.0 Hz, 1H), 3.98 (s, 3H).

Step 4: synthesis of methyl 5-bromo-4-(difluoromethyl)-2-fluorobenzoate

To a solution of methyl 5-bromo-2-fluoro-4-formylbenzoate (2.03 g, 7.79 mmol) in DCM (20 mL) at 0° C. was added deoxo-fluor (9.23 mL, 24.9 mmol). The reaction was then allowed to stir at rt for overnight. The reaction was quenched with aq. NaHCO$_3$ at 0° C. and extracted with DCM (×3). The combined DCM layers were washed by brine, dried over Na$_2$SO$_4$, filtered and concentrated. The residue was purified by chromatography on silica gel (0→10% MTBE in hexanes) to afford methyl 5-bromo-4-(difluoromethyl)-2-fluorobenzoate as pale yellow oil (1.55 g, 70% yield). $^1$H NMR (400 MHz, Chloroform-d) δ 8.18 (d, J=6.4 Hz, 1H), 7.46 (d, J=10.3 Hz, 1H), 6.85 (td, J=54.3, 0.9 Hz, 1H), 3.96 (s, 3H).

Step 5: synthesis of (5-bromo-4-(difluoromethyl)-2-fluorophenyl)methanol

To a solution of methyl 5-bromo-4-(difluoromethyl)-2-fluorobenzoate (310 mg, 1.1 mmol) in THF (5.5 mL) was added DIBAL-H (1.0 M solution in toluene, 3.3 mL, 3.3 mmol) at 0° C. The reaction was allowed to stir at the same temperature for 3 hours before carefully quenched with 10% Rochelle salt aq. solution. The crude was allowed to stir at rt for 1 hour and extracted with EtOAc (×3). The combined EtOAc layers were washed by brine, dried over Na$_2$SO$_4$, filtered and concentrated. The residue was purified by chromatography on silica gel (0→30% EtOAc in hexanes) to provide (5-bromo-4-(difluoromethyl)-2-fluorophenyl) methanol as colorless oil (252.3 mg, 90% yield). $^1$H NMR (400 MHz, Chloroform-d) δ 7.75 (d, J=6.5, 1H), 7.35 (d, J=9.8 Hz, 1H), 6.85 (td, J=54.7, 1.2 Hz, 1H), 4.80 (s, 2H).

Step 6: synthesis of ((5-bromo-4-(difluoromethyl)-2-fluorobenzyl)oxy)(tert-butyl)dimethylsilane To a solution of (5-bromo-4-(difluoromethyl)-2-fluorophenyl)methanol (252.3 mg, 0.99 mmol) in THF (5 mL) was added TBSCl (164 mg, 1.09 mmol) and imidazole (168 mg, 2.47 mmol). The suspension was allowed to stir at rt for 3 days. The reaction was filtered and concentrated. The residue was purified by chromatography on silica gel (0→20% MTBE in hexanes) to afford ((5-bromo-4-(difluoromethyl)-2-fluorobenzyl)oxy)(tert-butyl)dimethylsilane as colorless oil (327 mg, 90% yield). $^1$H NMR (400 MHz, Chloroform-d) δ 7.73 (dt, J=6.5, 1.2 Hz, 1H), 7.31 (d, J=9.9 Hz, 1H), 6.85 (td, J=54.8, 1.2 Hz, 1H), 4.79 (s, 2H), 0.96 (s, 9H), 0.13 (s, 6H).

Step 7: synthesis of 1-(5-(((tert-butyldimethylsilyl)oxy)methyl)-2-(difluoromethyl)-4-fluorophenyl)-4-cyclopropyl-1H-imidazole To a reaction vial was charged with tris(dibenzylideneacetone)dipalladium(0) (32.4 mg, 0.035 mmol) and Me$_4$tButylXphos (42.6 mg, 0.089 mmol) in toluene/1,4-dioxane (1.0 mL, 4/1) and heated at 120° C. for 3 min for pre-complexation. The resulting dark solution was cooled to rt and transferred to a separate vial charged with ((5-bromo-4-(difluoromethyl)-2-fluorobenzyl)oxy)(tert-butyl)dimethylsilane (327 mg, 0.885 mmol), 4-cyclopropyl-1H-imidazole (192 mg, 1.771 mmol) and K$_3$PO$_4$ (376 mg, 1.771 mmol) in toluene/1,4-dioxane (3.4 mL, 4/1). The reaction mixture was degassed vigorously under N$_2$ and allowed to stir at 120° C. for overnight. The reaction was cooled to rt, filtered and concentrated. The residue was purified by chromatography on silica gel (0→30% EtOAc in hexanes) to afford 1-(5-(((tert-butyldimethylsilyl)oxy)methyl)-2-(difluoromethyl)-4-fluorophenyl)-4-cyclopropyl-1H-imidazole as pale brown oil (130 mg, 37% yield).

Step 8: synthesis of (5-(4-cyclopropyl-1H-imidazol-1-yl)-4-(difluoromethyl)-2-fluorophenyl)methanol To a solution of 1-(5-(((tert-butyldimethylsilyl)oxy)methyl)-2-(difluoromethyl)-4-fluorophenyl)-4-cyclopropyl-1H-imidazole (130 mg, 0.328 mmol) in THF (1.6 mL) was added TBAF (1.0 M in THF, 0.66 mL, 0.66 mmol). The reaction was allowed to stir at rt for 1 hour, quenched by water, and extracted with EtOAc (×3). The combined EtOAc layers were washed by brine, dried over Na$_2$SO$_4$, filtered and concentrated. The residue was purified by chromatography on silica gel (0→100% EtOAc in hexanes) to provide (5-(4-cyclopropyl-1H-imidazol-1-yl)-4-(difluoromethyl)-2-fluorophenyl)methanol as white solid (58 mg, 63% yield). $^1$H NMR (400 MHz, Chloroform-d) δ 7.60 (s, 1H), 7.55 (d, J=6.3 Hz, 1H), 7.45 (d, J=9.5 Hz, 1H), 6.86 (s, 1H), 6.39 (t, J=54.2 Hz, 1H), 4.87 (s, 2H), 1.97-1.79 (m, 1H), 0.98-0.90 (m, 2H), 0.86-0.76 (m, 2H).

Step 9: synthesis of 5-(4-cyclopropyl-1H-imidazol-1-yl)-4-(difluoromethyl)-2-fluorobenzaldehyde To a solution of (5-(4-cyclopropyl-1H-imidazol-1-yl)-4-(difluoromethyl)-2-fluorophenyl)methanol (52 mg, 0.184 mmol) in DCM (0.92 mL) at 0° C. was added dess-martinperiodinane (156 mg, 0.368 mmol). The reaction was allowed to stir at 0° C. for 1 hour, quenched with saturated aq. Na$_2$S$_2$O$_3$ solution and extracted with DCM (×3). The combined DCM layers were washed by brine, dried over Na$_2$SO$_4$, filtered and concentrated. The residue was purified by chromatography on silica gel (0→50% acetone in hexanes) to provide 5-(4-cyclopropyl-1H-imidazol-1-yl)-4-(difluoromethyl)-2-fluorobenzaldehyde as colorless oil (50 mg, 97% yield). $^1$H NMR (400 MHz, Chloroform-d) δ 10.40 (s, 1H), 7.98 (s, 1H), 7.88 (d, J=5.8 Hz, 1H), 7.67 (d, J=9.6 Hz, 1H), 6.88 (s, 1H), 6.53 (t, J=54.0 Hz, 1H), 2.00-1.93 (m, 1H), 1.04-0.96 (m, 2H), 0.94-0.85 (m, 2H).

Step 10: synthesis of 5-(4-cyclopropyl-1H-imidazol-1-yl)-4-(difluoromethyl)-2-fluorobenzoic acid To suspension of 5-(4-cyclopropyl-1H-imidazol-1-yl)-2-fluoro-4-methylbenzaldehyde (50 mg, 0.178 mmol), 2-methylbute-2-ene (2.0 M in THF, 2.2 mL) and KH$_2$PO$_4$ (170 mg, 1.25 mmol) in tBuOH/H$_2$O (0.9 mL, 4/1) was added NaClO$_2$ (182 mg, 1.61 mmol). The reaction was allowed to stir at rt for overnight, quenched with saturated NH$_4$Cl aq. solution and extracted with EtOAc (×3). The combined EtOAc layers were washed by brine, dried over Na$_2$SO$_4$, filtered and concentrated. The residue was purified by chromatography on silica gel (0→100% MeOH in DCM) to provide 5-(4-cyclopropyl-1H-imidazol-1-yl)-4-(difluoromethyl)-2-fluorobenzoic acid as white solid (25 mg, 47% yield). $^1$H NMR (500 MHz, DMSO-d$_6$) δ 7.65 (s, 1H), 7.58 (s, br, 2H), 7.16 (s, 1H), 6.84 (t, J=54.0 Hz, 1H), 1.89-1.82 (m, 1H), 0.85-0.74 (m, 2H), 0.74-0.58 (m, 2H).

Step 11: synthesis of 5-(4-cyclopropyl-1H-imidazol-1-yl)-4-(difluoromethyl)-2-fluoro-N-(6-(1-isopropyl-1H-tetrazol-5-yl)pyridin-2-yl)benzamide 5-(4-cyclopropyl-1H-imidazol-1-yl)-4-(difluoromethyl)-2-fluoro-N-(6-(1-isopropyl-1H-tetrazol-5-yl)pyridin-2-yl)benzamide was prepared by using similar procedure as described for compound of Example 31a. LC/MS observed [M+1]: 483.18. $^1$H NMR (500 MHz, DMSO-d$_6$) δ 11.30 (s, 1H), 8.31 (d, J=8.3 Hz, 1H), 8.20-8.12 (m, 1H), 8.05-7.99 (m, 1H), 7.88 (dd, J=17.9, 7.8 Hz, 2H), 7.72 (d, J=1.4 Hz, 1H), 7.23 (d, J=1.4 Hz, 1H), 6.99 (t, J=53.8 Hz, 1H), 5.98 (p, J=6.6 Hz, 1H), 1.87 (ddd, J=13.3, 8.4, 5.0 Hz, 1H), 1.55 (d, J=6.6 Hz, 6H), 0.84-0.78 (m, 2H), 0.72 (dt, J=5.1, 2.9 Hz, 2H).

Example 32a was prepared following a similar protocol as Example 31a.

Example 33a

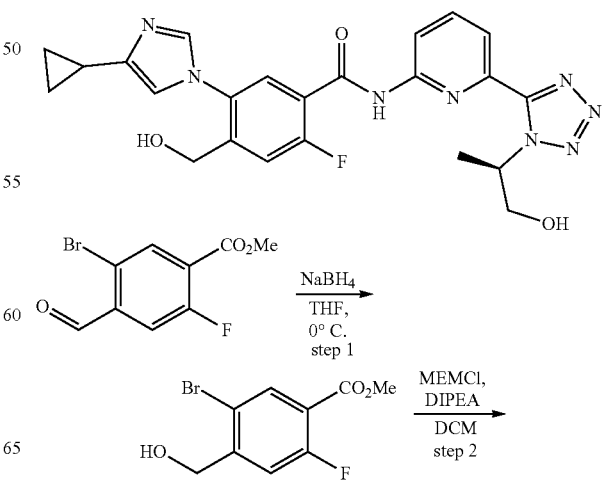

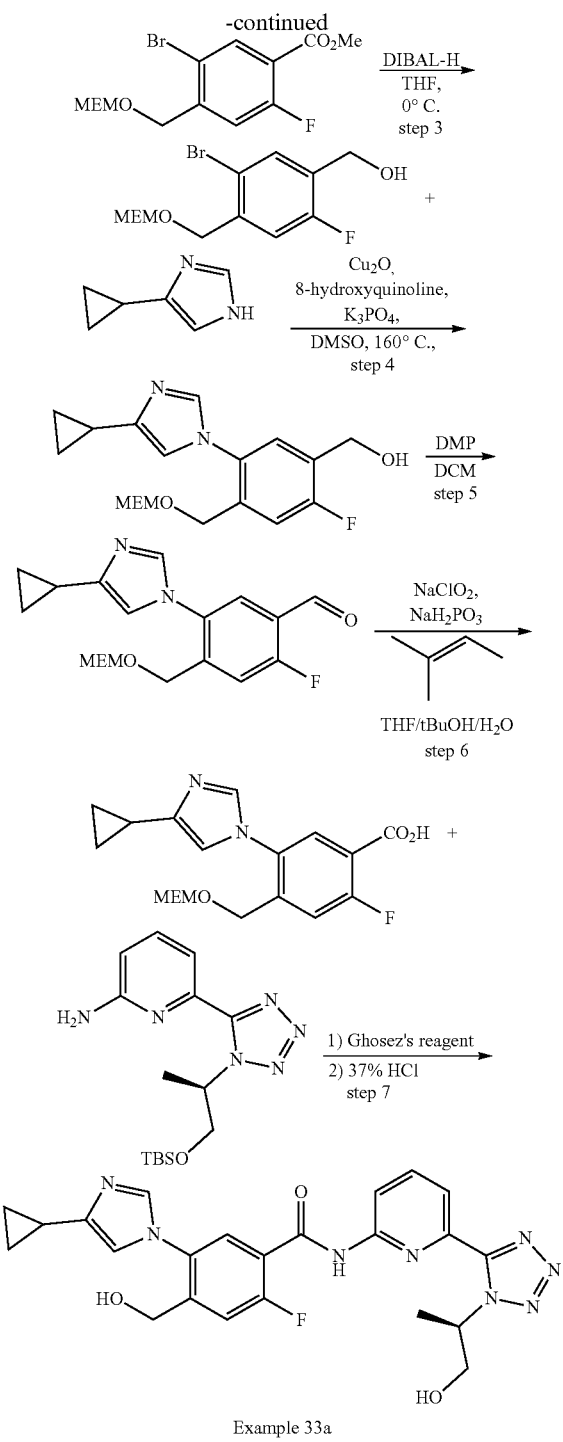

Example 33a

Step 1: synthesis of methyl
5-bromo-2-fluoro-4-(hydroxymethyl)benzoate

To a solution of methyl 5-bromo-2-fluoro-4-formylbenzoate (3.5 g, 13.4 mmol) in THF (27 mL) was added NaBH$_4$ (0.534 g, 14.1 mmol) at rt. The resulting suspension was allowed to cool to 0° C. and then MeOH (0.57 mL, 1.41 mmol) was then added. The reaction was allowed to stir at rt for overnight before carefully quenched with water at 0° C. The crude was extracted with EtOAc (×3). The combined EtOAc layers were washed by brine, dried over Na$_2$SO$_4$, filtered and concentrated to afford white solid. The resulting crude material was directly used in the following transformation without any purification.

Step 2: synthesis of methyl 5-bromo-2-fluoro-4-(((2-methoxyethoxy)methoxy)methyl)benzoate To a solution of methyl 5-bromo-2-fluoro-4-(hydroxymethyl)benzoate (0.891 g, 3.39 mmol) and DIPEA (1.18 mL, 6.77 mmol) in DCM (11 mL) at 0° C. was added MEMCl (0.65 mL, 5.42 mmol). The resulting solution was allowed to stir at 0° C. for 1 hour and then warm to rt for overnight. The reaction was quenched with saturated aq. NaHCO$_3$ solution and extracted with DCM (×3). The combined DCM layers were washed by brine, dried over Na$_2$SO$_4$, filtered and concentrated. The residue was purified by chromatography on silica gel (0→30% EtOAc in hexanes) to provide methyl 5-bromo-2-fluoro-4-(((2-methoxyethoxy)methoxy)methyl)benzoate as colorless oil (923.8 mg, 78% yield). $^1$H NMR (400 MHz, Chloroform-d) δ 8.10 (d, J=6.6 Hz, 1H), 7.35 (d, J=11.4 Hz, 1H), 4.89 (s, 2H), 4.66 (s, 2H), 3.93 (s, 3H), 3.79-3.74 (m, 2H), 3.60-3.53 (m, 2H), 3.40 (s, 3H).

Step 3: synthesis of (5-bromo-2-fluoro-4-(((2-methoxyethoxy)methoxy)methyl)phenyl)methanol To a solution of methyl 5-bromo-2-fluoro-4-(((2-methoxyethoxy)methoxy)methyl)benzoate (3.03 g, 8.63 mmol) in THF (28.8 mL) was added DIBAL-H (1.0 M solution in toluene, 25.9 mL, 25.9 mmol) at 0° C. The reaction was allowed to stir at the same temperature for 3 hours before carefully quenched with 10% Rochelle salt aq. solution. The crude was allowed to stir at rt for 1 hour and extracted with EtOAc (×3). The combined EtOAc layers were washed by brine, dried over Na$_2$SO$_4$, filtered and concentrated. The residue was purified by chromatography on silica gel (0→70% EtOAc in hexanes) to provide (5-bromo-2-fluoro-4-(((2-methoxyethoxy)methoxy)methyl)phenyl)methanol as colorless oil (2.14 g, 77% yield). $^1$H NMR (400 MHz, Chloroform-d) δ 7.62 (d, J=6.8 Hz, 1H), 7.23 (d, J=10.6 Hz, 1H), 4.87 (s, 2H), 4.74 (s, 2H), 4.64 (s, 2H), 3.79-3.75 (m, 2H), 3.62-3.55 (m, 2H), 3.40 (s, 3H).

Step 4: Synthesis of (5-(4-cyclopropyl-1H-imidazol-1-yl)-2-fluoro-4-(((2-methoxyethoxy)methoxy)methyl)phenyl)methanol To a microwave reaction vessel was charged with (5-bromo-2-fluoro-4-(((2-methoxyethoxy)methoxy)methyl)phenyl)methanol (640 mg, 1.98 mmol), 4-cyclopropyl-1H-imidazole (428 mg, 3.96 mmol), Cu$_2$O (28.3 mg, 0.198 mmol), 8-hydroxyquinoline (57.5 mg, 0.396 mmol) and K$_3$PO$_4$ (841 mg, 3.96 mmol) in DMSO (6.6 mL). The reaction was purged with N$_2$ (×3) and irradiated at 160° C. for 1 hour. The reaction was quenched with water and extracted with DCM (×3). The combined DCM layers were washed by brine, dried over Na$_2$SO$_4$, filtered and concentrated. The residue was purified by chromatography on silica gel (0→10% MeOH in DCM) to provide (5-(4-cyclopropyl-1H-imidazol-1-yl)-2-fluoro-4-(((2-methoxyethoxy)methoxy)methyl)phenyl)methanol as dark oil (534.3 mg, 77% yield). $^1$H NMR (400 MHz, DMSO-d$_6$) δ 7.61 (d, J=1.4 Hz, 1H), 7.38 (d, J=6.8 Hz, 1H), 7.35 (d, J=10.5 Hz, 1H), 7.11 (d, J=1.4 Hz, 1H), 5.40 (t, J=5.7 Hz, 1H), 4.66 (s, 2H), 4.58 (d, J=5.7 Hz, 2H), 4.37 (s, 2H), 3.57-3.52 (m, 2H), 3.44-3.39 (m, 2H), 3.22 (s, 3H), 1.89-1.77 (m, 1H), 0.82-0.77 (m, 2H), 0.71-0.66 (m, 2H).

Step 5: Synthesis of 5-(4-cyclopropyl-1H-imidazol-1-yl)-2-fluoro-4-(((2-methoxyethoxy)methoxy)methyl)benzaldehyde To a solution of (5-(4-cyclopropyl-1H-imidazol-1-yl)-2-fluoro-4-(((2-methoxyethoxy)methoxy)methyl)phenyl)methanol (534 mg, 1.52 mmol) in DCM (7.6 mL) at 0° C. was added dess-martinperiodinane (776 mg, 1.83 mmol). The reaction was allowed to stir at 0° C. for 1 hour, quenched with saturated aq. Na$_2$S$_2$O$_3$ solution and extracted with DCM (×3). The combined DCM layers were washed by brine, dried over Na$_2$SO$_4$, filtered and concentrated. The residue was purified by chromatography on silica gel (0→5% MeOH in DCM) to provide 5-(4-cyclopropyl-1H-imidazol-1-yl)-2-fluoro-4-(((2-methoxyethoxy)methoxy)methyl)benzaldehyde as pale yellow solid (171 mg, 32% yield). $^1$H NMR (400 MHz, DMSO-d$_6$) δ 10.20 (s, 1H), 7.77 (d, J=6.3 Hz, 1H), 7.70 (d, J=1.4 Hz, 1H), 7.61 (d, J=11.1 Hz, 1H), 7.20 (d, J=1.4 Hz, 1H), 4.71 (s, 2H), 4.49 (s, 2H), 3.61-3.55 (m, 2H), 3.47-3.39 (m, 2H), 3.21 (s, 3H), 1.90-1.79 (m, 1H), 0.86-0.80 (m, 2H), 0.73-0.64 (m, 2H).

Step 6: Synthesis of 5-(4-cyclopropyl-1H-imidazol-1-yl)-2-fluoro-4-(((2-methoxyethoxy)methoxy)methyl)benzoic acid To suspension of 5-(4-cyclopropyl-1H-imidazol-1-yl)-2-fluoro-4-(((2-methoxyethoxy)methoxy)methyl)benzaldehyde (170 mg, 0.488 mmol), 2-methylbute-2-ene (2.0 M in THF, 1.13 mL) and NaH$_2$PO$_4$ (82 mg, 0.683 mmol) in tBuOH/H$_2$O (4.9 mL, 4/1) was added NaClO$_2$ (123 mg, 0.98 mmol). The reaction was allowed to stir at rt for overnight, quenched with saturated Na$_2$SO$_3$ aq. solution and extracted with DCM (×3). The combined DCM layers were washed by brine, dried over Na$_2$SO$_4$, filtered and concentrated to afford 80 mg crude material as pale yellow solid, which was directly used in the following transformation without any purification.

Step 7: synthesis of (R)-5-(4-cyclopropyl-1H-imidazol-1-yl)-2-fluoro-4-(hydroxymethyl)-N-(6-(1-(1-hydroxypropan-2-yl)-1H-tetrazol-5-yl)pyridin-2-yl)benzamide (R)-5-(4-cyclopropyl-1H-imidazol-1-yl)-2-fluoro-4-(hydroxymethyl)-N-(6-(1-(1-hydroxypropan-2-yl)-1H-tetrazol-5-yl)pyridin-2-yl)benzamide was prepared by using similar procedure as described for compound of Example 33a. LC/MS observed [M+1]: 479.20. $^1$H NMR (400 MHz, DMSO-d$_6$) δ 11.13 (s, 1H), 8.31 (d, J=8.3 Hz, 1H), 8.14 (t, J=8.0 Hz, 1H), 7.97 (d, J=7.7 Hz, 1H), 7.72 (s, 1H), 7.70 (d, J=6.3 Hz, 1H), 7.55 (d, J=10.7 Hz, 1H), 7.22 (s, 1H), 5.92-5.82 (m, 1H), 5.62 (t, J=5.4 Hz, 1H), 4.91 (t, J=5.6 Hz, 1H), 4.42 (d, J=5.5 Hz, 2H), 3.79-3.68 (m, 2H), 1.85 (td, J=8.4, 4.2 Hz, 1H), 1.55 (d, J=6.8 Hz, 3H), 0.81 (dt, J=8.5, 3.0 Hz, 2H), 0.73-0.67 (m, 2H).

Example 37a

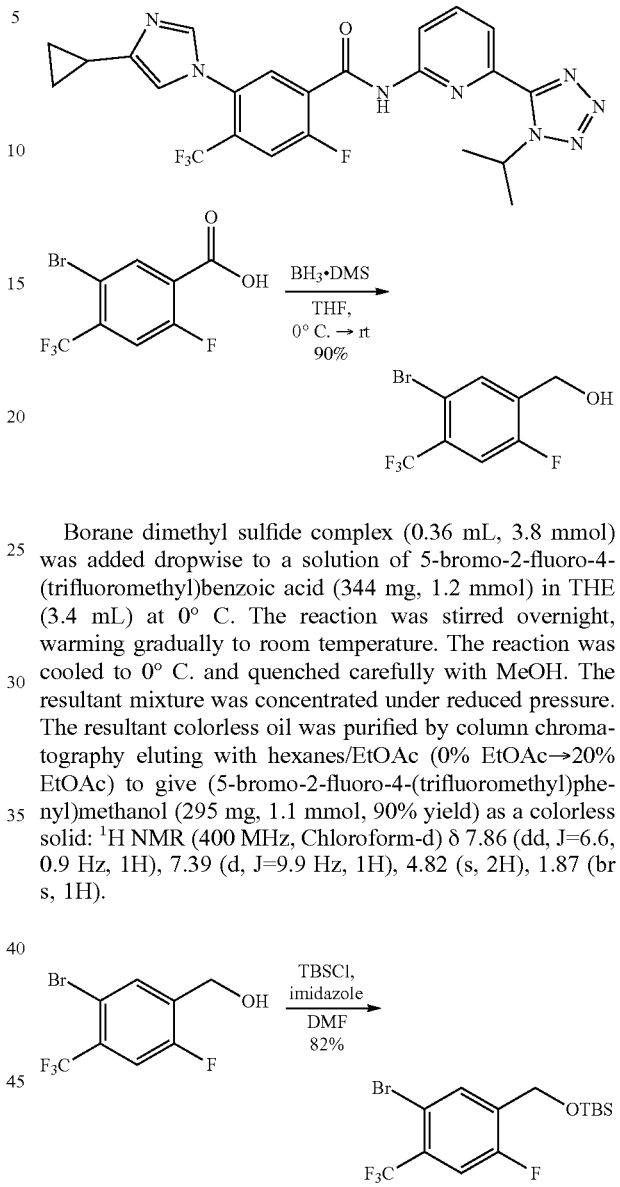

Borane dimethyl sulfide complex (0.36 mL, 3.8 mmol) was added dropwise to a solution of 5-bromo-2-fluoro-4-(trifluoromethyl)benzoic acid (344 mg, 1.2 mmol) in THF (3.4 mL) at 0° C. The reaction was stirred overnight, warming gradually to room temperature. The reaction was cooled to 0° C. and quenched carefully with MeOH. The resultant mixture was concentrated under reduced pressure. The resultant colorless oil was purified by column chromatography eluting with hexanes/EtOAc (0% EtOAc→20% EtOAc) to give (5-bromo-2-fluoro-4-(trifluoromethyl)phenyl)methanol (295 mg, 1.1 mmol, 90% yield) as a colorless solid: $^1$H NMR (400 MHz, Chloroform-d) δ 7.86 (dd, J=6.6, 0.9 Hz, 1H), 7.39 (d, J=9.9 Hz, 1H), 4.82 (s, 2H), 1.87 (br s, 1H).

TBS-Cl (280 mg, 1.86 mmol) was added to a solution of (5-bromo-2-fluoro-4-(trifluoromethyl)phenyl)methanol (362 mg, 1.33 mmol) and imidazole (253 mg, 3.71 mmol) in DMF (2.7 mL) and the reaction stirred for 6 hrs at ambient temperature. The reaction was quenched with H$_2$O and diluted with MTBE. The layers were separated, and the aqueous layer was extracted with MTBE (1×10 mL). The combined organic layers were washed with 10% citric acid, water, sat. NaHCO$_3$, and brine. The organic layer was dried (MgSO$_4$), filtered, and concentrated under reduced pressure. The resultant colorless oil was purified by column chromatography eluting with hexanes/EtOAc (0% EtOAc→4% EtOAc) to give ((5-bromo-2-fluoro-4-(trifluoromethyl)benzyl)oxy)(tert-butyl)dimethylsilane (423 mg, 1.09 mmol, 82% yield) as a colorless oil: $^1$H NMR (500 MHz, Chloroform-d) δ 7.84 (d, J=6.7 Hz, 1H), 7.34 (d, J=9.9 Hz, 1H), 4.80 (s, 2H), 0.96 (s, 9H), 0.14 (s, 6H).

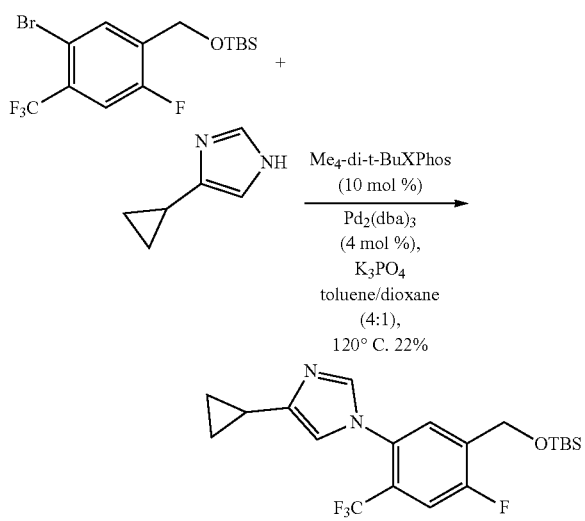

A mixture of Pd₂(dba)₃ (9.5 mg, 10.3 µmol) and Me₄t-ButylXphos (12.4 mg, 0.03 mmol) in 0.5 mL of 4:1 PhMe:1,4-dioxane was sparged with N₂ for 5 minutes. The reaction was heated at 120° C. for 5 minutes to pre-form the active Pd species. The reaction was cooled to rt. In a separate vial, a mixture of ((5-bromo-2-fluoro-4-(trifluoromethyl)benzyl)oxy)(tert-butyl)dimethylsilane (100 mg, 0.26 mmol), 4-cyclopropyl-1H-imidazole (55.8 mg, 0.52 mmol), and K₃PO₄ (110 mg, 0.52 mmol) in 0.7 mL of 4:1 PhMe:1,4-dioxane was sparged with N₂ for 5 minutes. The catalyst solution was added to the remaining reaction mixture and the reaction was heated at 120° C. overnight. The reaction was filtered through celite, rinsed with DCM, and concentrated under reduced pressure. The resultant brown oil was purified by column chromatography eluting with hexanes/EtOAc (0% EtOAc→20% EtOAc) to give 1-(5-(((tert-butyldimethylsilyl)oxy)methyl)-4-fluoro-2-(trifluoromethyl)phenyl)-4-cyclopropyl-1H-imidazole (23.3 mg, 0.06 mmol, 22% yield) as a pale yellow oil: LCMS (m/z) 415.17 [M+1]; ¹H NMR (400 MHz, Chloroform-d) δ 7.70 (s, 1H), 7.55 (d, J=6.2 Hz, 1H), 7.47 (d, J=9.4 Hz, 1H), 6.84 (s, 1H), 4.85 (s, 2H), 1.98 (ddd, J=13.3, 8.4, 5.1 Hz, 1H), 0.98 (dt, J=8.0, 2.7 Hz, 2H), 0.94-0.91 (comp, 11H), 0.14 (s, 6H).

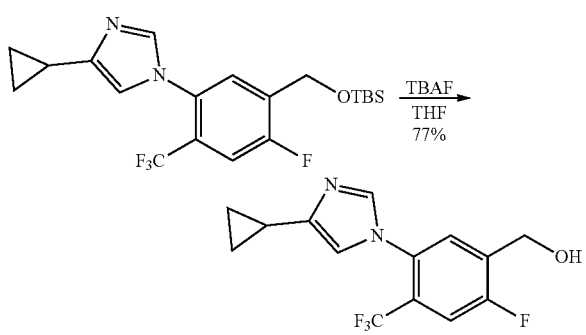

TBAF (0.11 mL of a 1.0 M solution in THF, 0.11 mmol) was added dropwise to a solution of 1-(5-(((tert-butyldimethylsilyl)oxy)methyl)-4-fluoro-2-(trifluoromethyl)phenyl)-4-cyclopropyl-1H-imidazole (23 mg, 0.06 mmol) in THF (0.79 mL) and the reaction stirred for 1 hr. The reaction was purified by column chromatography eluting with hexanes/EtOAc (0% EtOAc→80% EtOAc) to give (5-(4-cyclopropyl-1H-imidazol-1-yl)-2-fluoro-4-(trifluoromethyl)phenyl)methanol (12.8 mg, 0.04 mmol, 77% yield) as a yellow solid: LCMS (m/z) 301.07 [M+1]; ¹H NMR (400 MHz, Chloroform-d) δ 8.02 (s, 1H), 7.69 (d, J=6.2 Hz, 1H), 7.40 (d, J=9.3 Hz, 1H), 6.81 (s, 1H), 4.82 (s, 2H), 1.90 (tt, J=8.3, 5.1 Hz, 1H), 0.98-0.89 (m, 2H), 0.89-0.79 (m, 2H).

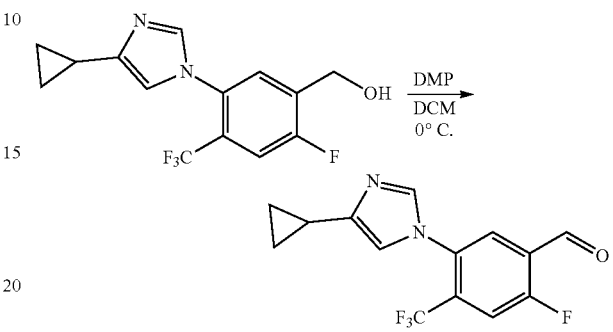

Dess-Martin periodinane (62.7 mg, 0.15 mmol) was added to a solution of (5-(4-cyclopropyl-1H-imidazol-1-yl)-2-fluoro-4-(trifluoromethyl)phenyl)methanol (22.2 mg, 0.07 mmol) in DCM (0.37 mL) at 0° C. and the reaction stirred at 0° C. for 1.5 hrs. The reaction was quenched with sat. Na₂S₂O₃ and extracted with DCM (3×2 mL). The combined organic layers were dried (MgSO₄), filtered, and concentrated under reduced pressure. The resultant pale yellow residue was purified by column chromatography eluting with hexanes/EtOAc (0% EtOAc→55% EtOAc) to give 5-(4-cyclopropyl-1H-imidazol-1-yl)-2-fluoro-4-(trifluoromethyl)benzaldehyde (21 mg, 0.07 mmol, 95% yield) as a colorless gum: LCMS (m/z) 299.06 [M+1]; ¹H NMR (400 MHz, Chloroform-d) δ 10.40 (s, 1H), 7.87 (d, J=6.0 Hz, 1H), 7.67 (d, J=9.6 Hz, 1H), 7.49 (s, 1H), 6.81 (s, 1H), 1.89 (tt, J=8.3, 5.1 Hz, 1H), 0.93-0.85 (m, 2H), 0.85-0.78 (m, 2H).

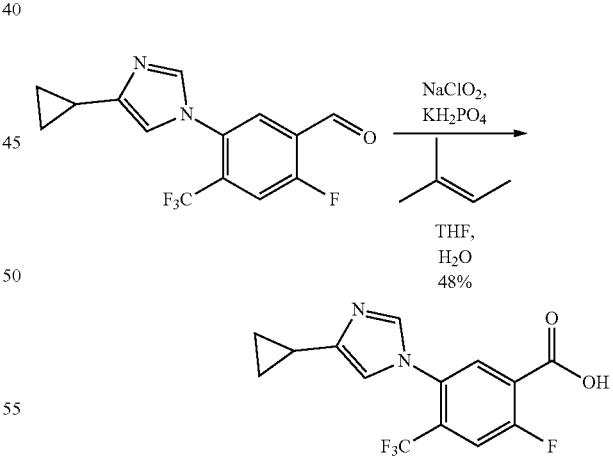

Sodium chlorite (71.6 mg, 0.63 mmol) was added to a solution of 5-(4-cyclopropyl-H-imidazol-1-yl)-2-fluoro-4-(trifluoromethyl)benzaldehyde (21 mg, 0.07 mmol), 2-methylbut-2-ene (0.88 mL of a 2.0 M solution in THF, 1.76 mmol), and potassium dihydrogen phosphate (67.1 mg, 0.49 mmol) in THF (0.75 mL)/H₂O (0.25 mL) and the reaction was stirred for 1 hr. The reaction was quenched with sat. NH₄Cl (5 mL) and diluted with EtOAc (5 mL). The layers were separated and the aqueous layer extracted with EtOAc (2×5 mL). The combined organic layers were dried (MgSO₄), filtered, and concentrated under reduced pressure. The resultant white solid purified by column chromatography eluting with CH₂Cl₂/MeOH (0% MeOH→25% MeOH) to give 5-(4-cyclopropyl-1H-imidazol-1-yl)-2-fluoro-4-(trifluoromethyl)benzoic acid (10.7 mg, 0.03 mmol, 48% yield) as a white solid: LCMS (m/z) 315.05 [M+1]; ¹H NMR (400 MHz, Methanol-d₄) δ 8.19 (s, 1H), 7.97 (d, J=6.1 Hz, 1H), 7.80 (d, J=9.8 Hz, 1H), 7.23 (s, 1H), 1.94 (ddd, J=8.5, 5.1, 3.4 Hz, 1H), 1.01-0.93 (m, 2H), 0.82-0.75 (m, 2H).

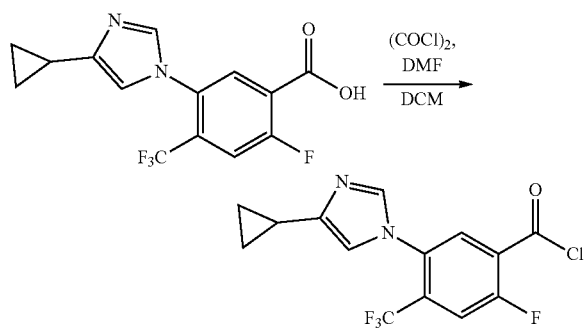

Oxalyl chloride (7 μl, 0.08 mmol) was added to a mixture of 5-(4-cyclopropyl-1H-imidazol-1-yl)-2-fluoro-4-(trifluoromethyl)benzoic acid (6 mg, 0.02 mmol) and DMF (1 drop) in DCM (55 μl) and the reaction stirred for 30 minutes. The reaction was concentrated under reduced pressure and dried under vacuum. The resultant yellow residue was taken on directly to the next step without purification.

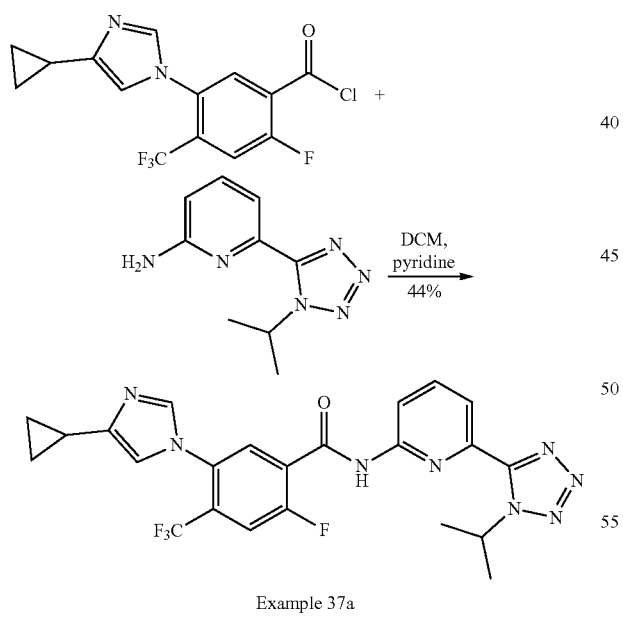

Example 37a 6-(1-Isopropyl-1H-tetrazol-5-yl)pyridin-2-amine (5.9 mg, 0.03 mmol) was added to a solution of 5-(4-cyclopropyl-1H-imidazol-1-yl)-2-fluoro-4-(trifluoromethyl)benzoyl chloride (6.4 mg, 0.02 mmol) in DCM (27 μl)/Pyridine (27 μl) and the reaction was stirred for a hr. The reaction was concentrated under reduced pressure. The resultant orange residue was purified by column chromatography eluting with CH₂Cl₂/MeOH (0% MeOH→5% MeOH) to give Example 37a (4.2 mg, 8.4 μmol, 44% yield) as a clear gum.

Example 40a

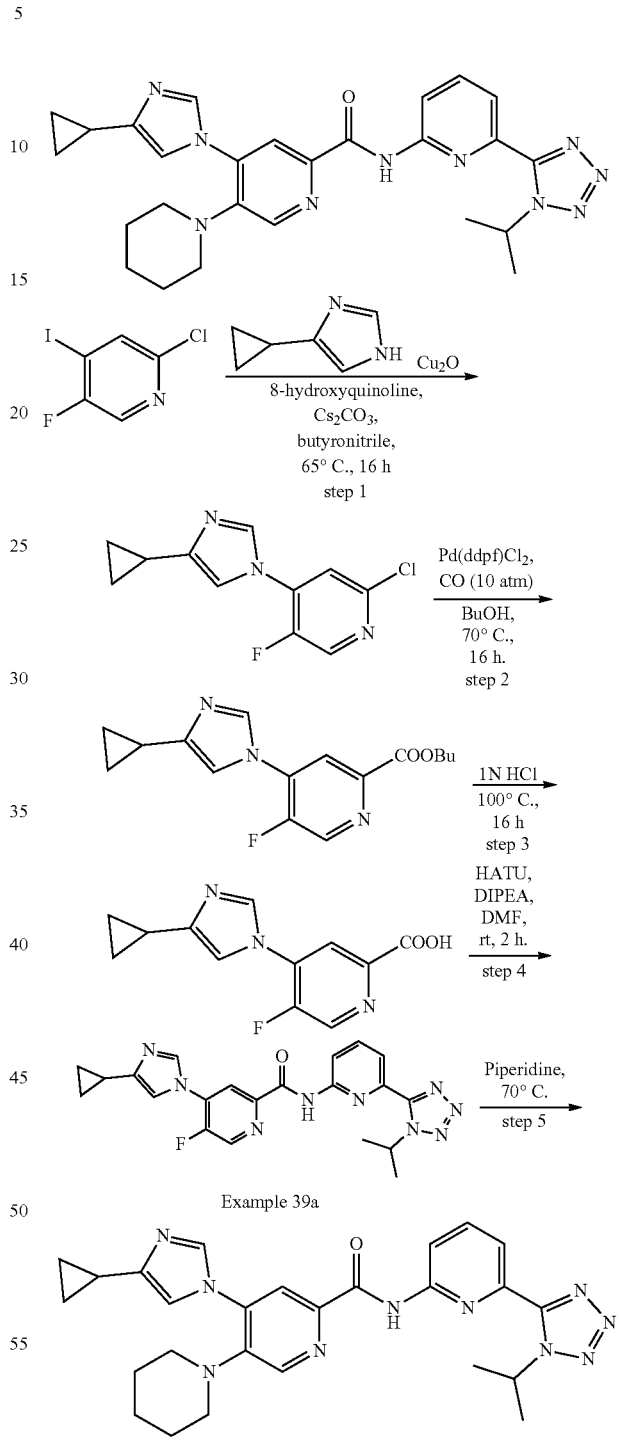

Example 40a

Step 1: A mixture of 4-cyclopropyl-1H-imidazole (1.95 g, 18.1 mmol), 2-chloro-5-fluoro-4-iodopyridine (3.1 g, 12.0 mmol), Cu₂O (105 mg, 0.6 mmol), 8-hydroxyquinoline (353 mg, 2.4 mmol), and Cs₂CO₃ (11.7 g, 36 mmol) in butyronitrile (100 mL) was stirred at 65° C. for 16 h. After cooling down to room temperature, 100 mL of water was added and the resulting mixture was extracted with EtOAc (100 mL×2). The organic layer was dried over Na₂SO₄, filtered, and evaporated. The residue was purified by silica gel column chromatography with PE/EtOAc (3:1) to afford 1.7 g (57%) of 2-chloro-4-(4-cyclopropyl-1H-imidazol-1-yl)-5-fluoropyridine as white solid.

Step 2: In a 50 mL autoclave a mixture of 2-chloro-4-(4-cyclopropyl-H-imidazol-1-yl)-5-fluoropyridine (1.7 g, 7.1 mmol), Pd(dppf)Cl₂ (539 mg, 0.7 mmol), and Et₃N (2.13 g, 21 mmol) in BuOH (30 mL) was stirred under 10 atm of CO at 70° C. for 16 hours. The resulting mixture was concentrated under reduced pressure. The residue was purified by silica gel column chromatography with PE/EtOAc (3:1) to afford butyl 4-(4-cyclopropyl-1H-imidazol-1-yl)-5-fluoropicolinate (1.6 g, 73.7%) as a yellow oil.

Step 3: To a solution of butyl 4-(4-cyclopropyl-H-imidazol-1-yl)-5-fluoropicolinate (800 mg, 2.64 mmol) in acetonitrile (5 mL) was added 1M HCl (5 mL). The resulting mixture was stirred at 100° C. under nitrogen atmosphere overnight. Solvent was removed under reduced pressure. The residue was purified by reverse phase chromatography with 0-30% MeCN/water to afford 4-(4-cyclopropyl-1H-imidazol-1-yl)-5-fluoropyridine-2-carboxylic acid (320 mg, 49.0%) as a white solid.

Step 4: A mixture of 4-(4-cyclopropyl-1H-imidazol-1-yl)-5-fluoropyridine-2-carboxylic acid (300 mg, 1.21 mmol), 6-[1-(propan-2-yl)-1H-1,2,3,4-tetrazol-5-yl]pyridin-2-amine (371.7 mg, 1.82 mmol), HATU (922.8 mg, 2.43 mmol) and NMM (368.2 mg, 3.64 mmol) in DMF (5 mL) was stirred at room temperature overnight. Solvent was removed under vacuum. The crude product was purified by reverse phase chromatography with 0-60% CH₃CN/H₂O to afford Example 39a (100 mg, 19.01%) as a white solid.

Step 5: Example 39a (20 mg, 50 mmol) was dissolved in piperidine (1 mL) and stirred at 70° C. for 1 h. The resulting mixture was concentrated under vacuum. The crude product was purified by reverse phase chromatography with 0-75% CH₃CN/H₂O to afford Example 40a (7 mg, 30.4%) as a light brown solid.

Example 41a

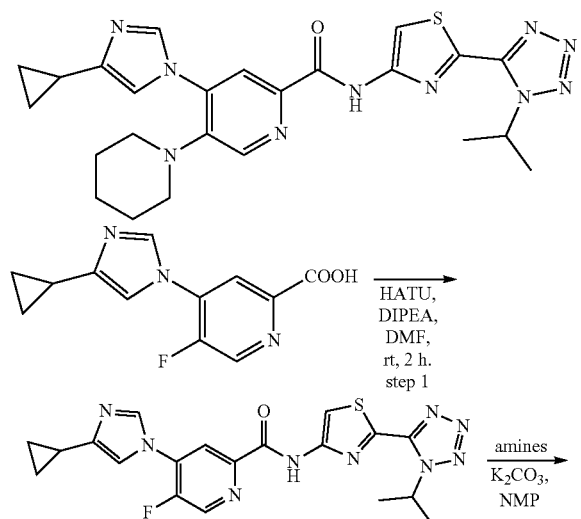

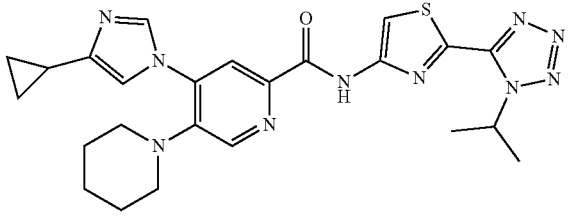

Example 41a

Step 1: A mixture of 4-(4-cyclopropyl-1H-imidazol-1-yl)-5-fluoropyridine-2-carboxylic acid (200 mg, 0.8 mmol), 2-(1-isopropyl-1H-tetrazol-5-yl)thiazol-4-amine (245.3 mg, 1.2 mmol), HATU (615.2 mg, 1.6 mmol) and NMM (254.4 mg, 2.4 mmol) in DMF (5 mL) was stirred at room temperature overnight. The resulting mixture was concentrated under vacuum. The crude product was purified by reverse phase chromatography with 0-60% CH₃CN/H₂O to afford Example 38a (160 mg, 45.5%) as a white solid.

Step 2: A solution of Example 38 (30 mg, 0.068 mmol) in piperidine (1 mL) was stirred at 70° C. for 1 h. The reaction mixture was concentrated under vacuum. The crude product was purified by reverse phase chromatography with 0-75% CH₃CN/H₂O to afford Example 41 (12 mg, 34.8%) as a light brown solid.

Examples 42a, 44a, and 45a were prepared following a similar protocol as Example 41a.

Examples 43a, 46a, and 47a were prepared following a similar protocol as Example 40a.

Example 52a

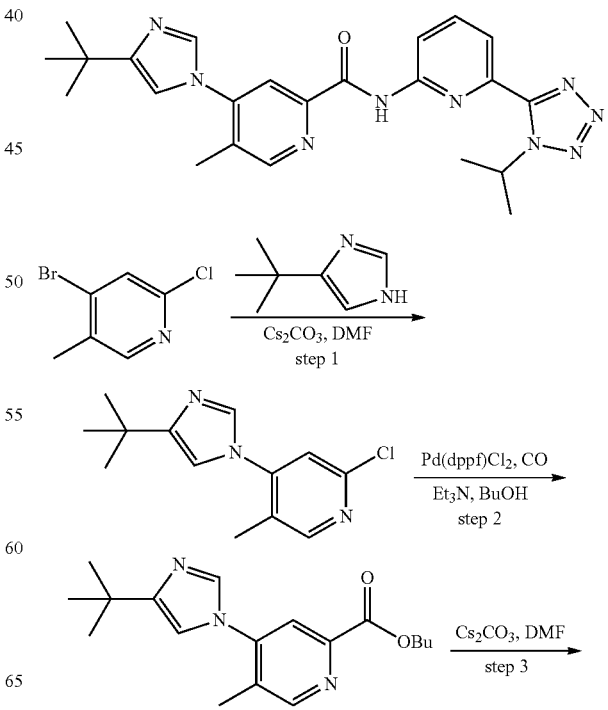

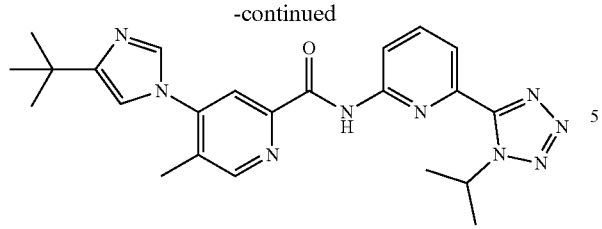

Example 52a

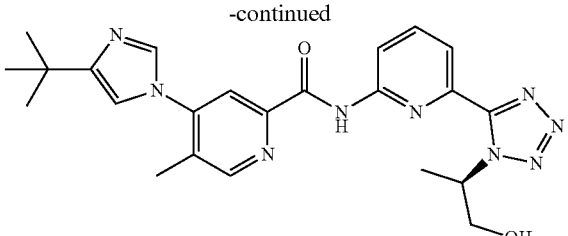

Example 53a

Step 1: 4-Bromo-2-chloro-5-methylpyridine (600 mg, 2.9 mmol) was added to a mixture of 4-(tert-butyl)-1H-imidazole (431 mg, 3.48 mmol) and $Cs_2CO_3$ (2.83 g, 8.7 mmol) in DMF (2 mL). The resulting solution was stirred at 100° C. overnight. The mixture was cooled to rt, diluted with EtOAc (100 mL), and washed with water (30 mL×2) and brine (30 mL). The organic layer was dried over $Na_2SO_4$, filtered, and concentrated in vacuo. Purification of the residue on a silica gel column with 30% EtOAc/PE provided 400 mg (55%) of 4-(4-(tert-butyl)-1H-imidazol-1-yl)-2-chloro-5-methyl pyridine as a light yellow solid.

Step 2: In a 50 mL autoclave a mixture of 2-chloro-5-methyl-4-(4-(trifluoromethyl)-1H-imidazol-1-yl)pyridine (400 mg, 1.6 mmol), Pd(dppf)$Cl_2$ (195 mg, 0.24 mmol), and $Et_3N$ (485 mg, 4.8 mmol) in BuOH (20 mL) was stirred under 10 atm of CO at 70° C. for 16 hours. The reaction mixture was concentrated under reduced pressure. The residue was purified by silica gel column chromatography with PE/EtOAc (3:1) to afford butyl 4-(4-(tert-butyl)-1H-imidazol-1-yl)-5-methylpicolinate (380 mg, 75%) as a white solid.

Step 3: Butyl 4-(4-(tert-butyl)-1H-imidazol-1-yl)-5-methylpicolinate (50 mg, 0.15 mmol) was added to a mixture of 6-[1-(propan-2-yl)-1H-1,2,3,4-tetrazol-5-yl]pyridin-2-amine (43 mg, 0.18 mmol) and $Cs_2CO_3$ (146 mg, 0.45 mmol) in DMF (2 mL). The resulting mixture was stirred at 100° C. for 2 h, cooled down to room temperature, and filtered. The filtrate was purified by Flash-Prep-HPLC with 0-100% MeCN/$H_2O$ to afford 12.4 mg of Example 52 as a white solid.

Examples 48a and 50a were prepared following a similar protocol as Example 52a.

Example 53a

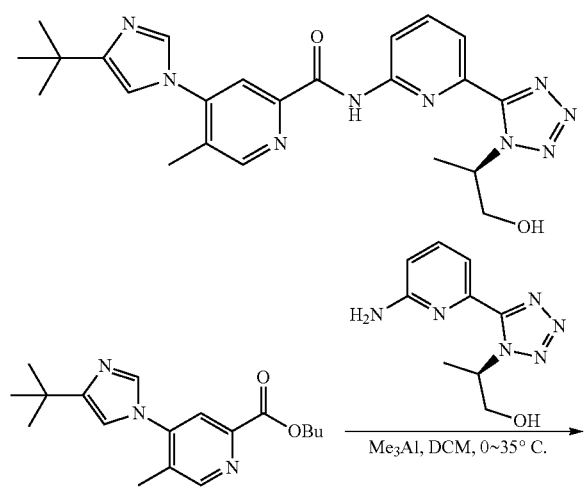

$Me_3Al$ (1 ml, 2 M in toluene) was added to a solution of (R)-2-(5-(6-aminopyridin-2-yl)-1H-tetrazol-1-yl)propan-1-ol (43 mg, 0.18 mmol) in DCM at 0° C., and the resulting mixture was stirred at this temperature for 1 hour. A solution of butyl 4-(4-(tert-butyl)-1H-imidazol-1-yl)-5-methylpicolinate (50 mg, 0.15 mmol) in DCM (2 mL) was added. The resulting solution was stirred at 35° C. overnight. The reaction was quenched with Rochelle salt and extracted with EtOAc. The organic layer was dried over anhydrous $Na_2SO_4$, filtered, and concentrated in vacuo. The crude product was purified by Flash-Prep-HPLC with 0-100% MeCN/$H_2O$ to afford 9.4 mg of Example 53a as a white solid.

Examples 49a and 51a were prepared following a similar protocol as Example 53a.

Example 55a

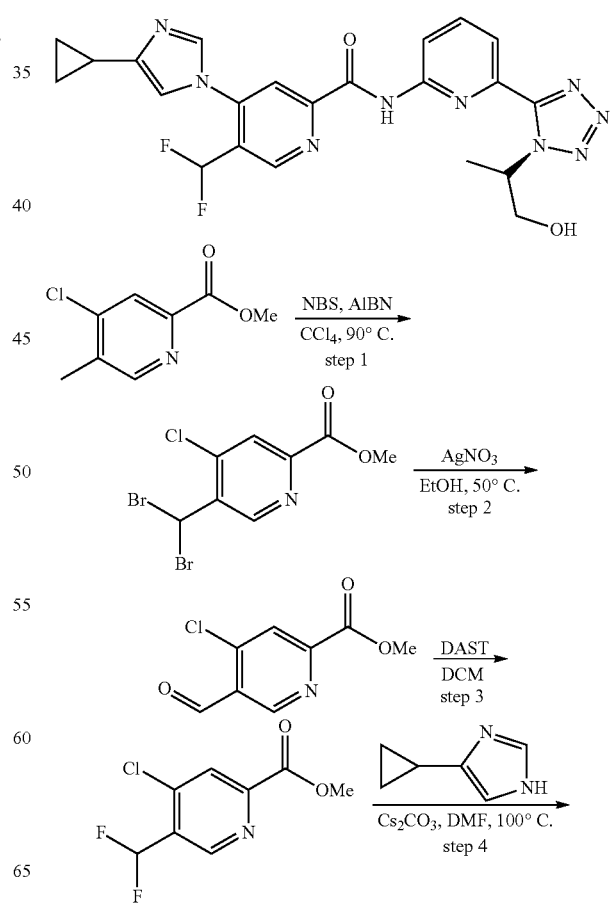

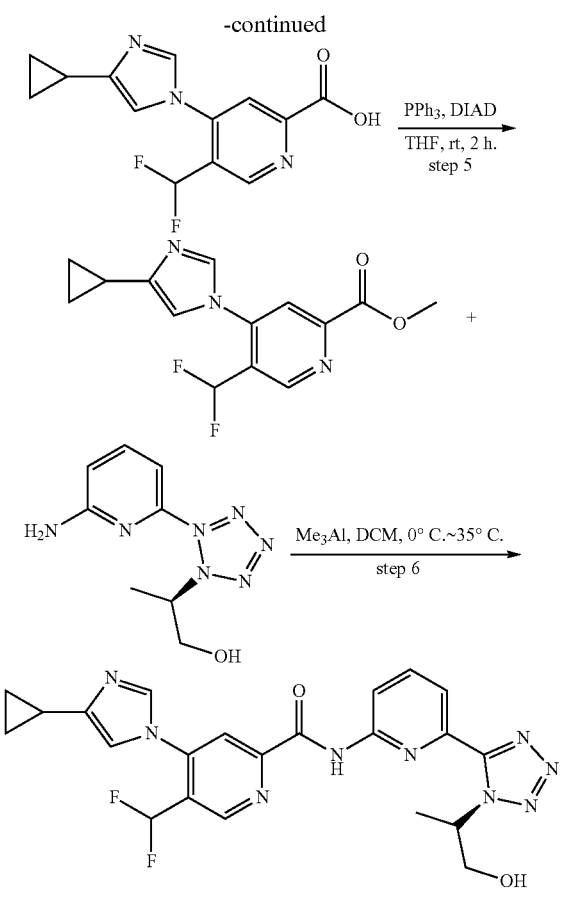

Example 55a

Step 1: Into a sealed tube were added methyl 4-chloro-5-methylpyridine-2-carboxylate (3 g, 16.16 mmol), NBS (14.4 g, 80.81 mmol), AIBN (1.3 g, 8.08 mmol) and CCl$_4$ (60 mL). The resulting mixture was stirred at 90° C. under nitrogen atmosphere overnight. The reaction mixture was cooled to rt, diluted with DCM, and washed with H$_2$O and brine. The organic layer was dried over anhydrous Na$_2$SO$_4$, filtered, and concentrated under reduced pressure. The residue was purified by silica gel column chromatography with EA in PE (010%) to afford methyl 4-chloro-5-(dibromomethyl)pyridine-2-carboxylate (4.4 g, 79.3%) as a grey solid.

Step 2: A mixture of methyl 4-chloro-5-(dibromomethyl)pyridine-2-carboxylate (4.4 g, 12.81 mmol) and AgNO$_3$ (6.5 g, 38.44 mmol) in EtOH (90 mL) and H$_2$O (9 mL) was stirred at 50° C. overnight. The reaction mixture was filtered through diatomite and the filtrate was concentrated under reduced pressure. Purification of the residue by silica gel column chromatography with EtOAc in PE (0-50%) afforded methyl 4-chloro-5-formylpyridine-2-carboxylate (1.4 g, 54.7%) as a yellow solid.

Step 3: A mixture of methyl 4-chloro-5-formylpyridine-2-carboxylate (1.4 g, 7.01 mmol) and DAST (2.8 g, 17.54 mmol) in DCM (15 mL) was stirred at room temperature for 2 h. The resulting mixture was concentrated under vacuum and the residue was purified by silica gel column chromatography with EtOAc in PE (0-10%) to afford methyl 4-chloro-5-(difluoromethyl)pyridine-2-carboxylate (0.9 g, 57.9%) as a yellow solid.

Step 4: A mixture of methyl 4-chloro-5-(difluoromethyl)pyridine-2-carboxylate (700 mg, 3.16 mmol), 4-cyclopropyl-1H-imidazole (409.9 mg, 3.79 mmol) and Cs$_2$CO$_3$ (2058.5 mg, 6.32 mmol) in DMF (10 mL) was stirred at 100° C. for 2 h. The mixture was cooled down to room temperature and acidified to pH 3-4 with HCl (aq). Solvent was removed under vacuum and the crude product was purified by revere phase chromatography with 0-20% MeCN/H$_2$O to afford 4-(4-cyclopropyl-1H-imidazol-1-yl)-5-(difluoromethyl)pyridine-2-carboxylic acid (550 mg, 62.4%) as a yellow solid.

Step 5: A mixture of 4-(4-cyclopropyl-1H-imidazol-1-yl)-5-(difluoromethyl)pyridine-2-carboxylic acid (100 mg, 0.36 mmol), MeOH (22.9 mg, 0.72 mmol), PPh$_3$ (187.8 mg, 0.72 mmol), and DIAD (144.8 mg, 0.72 mmol) in THF (2 mL) was stirred at room temperature under nitrogen atmosphere for 2 h. Solvent was removed under vacuum and the residue was purified by reverse phase chromatography with 20-30% CH$_3$CN/water to afford methyl 4-(4-cyclopropyl-1H-imidazol-1-yl)-5-(difluoromethyl)pyridine-2-carboxylate (80 mg, 76.2%) as colorless oil.

Step 6: To a stirred solution of (2R)-2-[5-(6-aminopyridin-2-yl)-1H-1,2,3,4-tetrazol-1-yl]propan-1-ol (180.2 mg, 0.82 mmol) in DCM (10 mL) at 0° C. was added a 2 M solution of Me$_3$Al (2 mL, 4.1 mmol) in toluene dropwise under nitrogen. The mixture was stirred at 0° C. for 1 h and methyl 4-(4-cyclopropyl-1H-imidazol-1-yl)-5-(difluoromethyl)pyridine-2-carboxylate (240 mg, 0.818 mmol) was added. The resulting mixture was stirred at 35° C. for additional 1 h. The reaction was quenched with Rochelle's salt and extracted with DCM. The organic layer was dried over anhydrous Na$_2$SO$_4$ and concentrated under reduced pressure. Purification of the residue by reverse phase chromatography with 0-35% MeCN/H$_2$O afforded Example 55a (115.1 mg, 29.21%) as a white solid.

Examples 54a and 56a were prepared following a similar protocol as Example 55a.

Example 57a

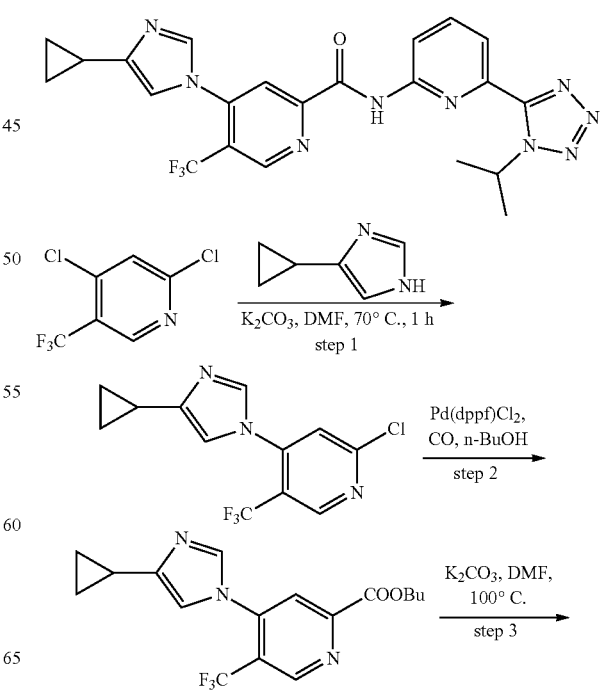

-continued

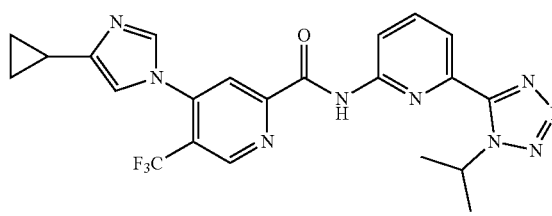

Example 57a

Step 1: Into a 50-mL round-bottom flask purged with nitrogen, was placed a solution of 2,4-dichloro-5-(trifluoromethyl)pyridine (800 mg, 3.7 mmol) in DMF (2 mL), 4-cyclopropyl-1H-imidazole (482 mg, 4.4 mmol) and $K_2CO_3$ (1.53 g, 11.1 mmol). The resulting mixture was stirred at 70° C. overnight. Solvent was removed in vacuo. Purification of the crude product on a silica gel column with 30% EtOAc/PE afforded 360 mg (38%) of 2-chloro-4-(4-cyclopropyl-1H-imidazol-1-yl)-5-(trifluoromethyl)pyridine as a yellow solid.

Step 2: In a 50 mL autoclave a mixture of 2-chloro-4-(4-cyclopropyl-H-imidazol-1-yl)-5-(trifluoromethyl)pyridine (360 mg, 1.25 mmol), Pd(dppf)Cl$_2$ (152 mg, 0.187 mmol), and Et$_3$N (387 mg, 3.75 mmol) in BuOH (20 mL) was stirred under 10 atm of CO at 70° C. for 16 hours. The resulting mixture was concentrated under reduced pressure. The residue was purified by silica gel column chromatography with PE/EtOAc (3:1) to afford butyl 4-(4-cyclopropyl-1H-imidazol-1-yl)-5-(trifluoromethyl)picolinate (270 mg, 61%) as a yellow oil.

Step 3: Butyl-4-(4-cyclopropyl-1H-imidazol-1-yl)-5-(trifluoromethyl)picolinate (60 mg, 0.17 mmol) was added into a mixture of 6-[1-(propan-2-yl)-1H-1,2,3,4-tetrazol-5-yl]pyridin-2-amine (49 mg, 0.2 mmol) and $K_2CO_3$ (70 mg, 0.5 mmol) in dichloromethane (2 mL). The resulting mixture was stirred at 100° C. for 2 h. Solvent was removed in vacuo and the crude product was purified by Flash-Prep-HPLC with 0-100% MeCN/H$_2$O to afford 25.3 mg (31%) of Example 57a as a white solid.

Example 58a

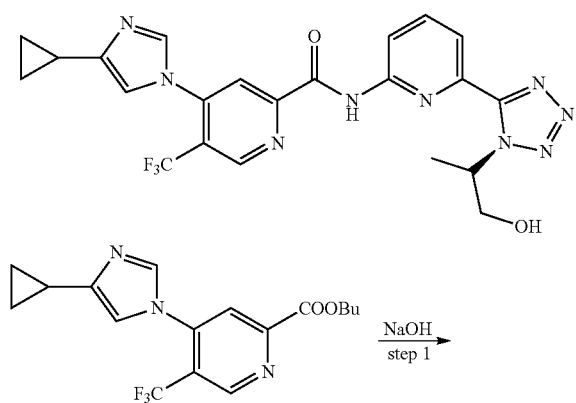

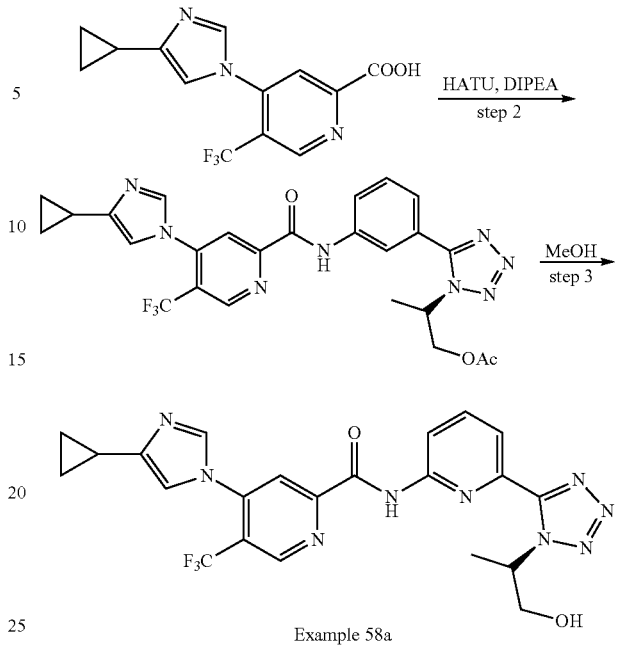

Example 58a

Step 1: A mixture of butyl 4-(4-cyclopropyl-1H-imidazol-1-yl)-5-(trifluoromethyl)picolinate (50 mg, 0.14 mmol) and NaOH (56 mg, 1.4 mmol) in MeOH (6 mL) and H$_2$O (2 mL) was stirred at room temperature for 2 h. Solvent was removed in vacuo and the crude product was purified by Flash-Prep-HPLC with 0-100% MeCN/H$_2$O to afford 25 mg (59%) of 4-(4-cyclopropyl-1H-imidazol-1-yl)-5-(trifluoromethyl)picolinic acid as a white solid.

Step 2: A mixture of 4-(4-cyclopropyl-1H-imidazol-1-yl)-5-(trifluoromethyl)picolinic acid (25 mg, 0.08 mmol), (R)-2-(5-(6-aminopyridin-2-yl)-1H-tetrazol-1-yl)propyl acetate (27 mg, 0.1 mmol), HATU (61 mg, 0.16 mmol) and DIEA (31 mg, 0.24 mmol) in dichloromethane (2 mL) was stirred at room temperature for 2 h. Solvent was removed in vacuo and the crude product was purified by Flash-Prep-HPLC with 0-100% MeCN/H$_2$O to afford 20 mg (44%) of (R)-2-(5-(6-(4-(4-cyclopropyl-1H-imidazol-1-yl)-5-(trifluoromethyl)picolinamido)pyridin-2-yl)-1H-tetrazol-1-yl)propyl acetate as white solid.

Step 3: $K_2CO_3$ (15 mg, 0.11 mmol) was added to a solution of (R)-2-(5-(6-(4-(4-Cyclopropyl-1H-imidazol-1-yl)-5-(trifluoromethyl)picolinamido)pyridin-2-yl)-1H-tetrazol-1-yl)propyl acetate (20 mg, 0.037 mmol) in MeOH (5 mL). The resulting mixture was stirred at room temperature for 2 h. Solvent was removed in vacuo and the crude product was purified by Flash-Prep-HPLC with 0-100% MeCN/H$_2$O to afford 9.7 mg (51%) of Example 58 as white solid.

Example 59a was prepared following a similar protocol as Example 57a.

Examples 8a-18a, 20a-26a, 34a-36a, 60a and 61a were prepared following the similar methods as Example 1a.

| Example | Structure | LC-MS [M + H]+ unless otherwise noted | H-NMR |
|---|---|---|---|
| 8a | 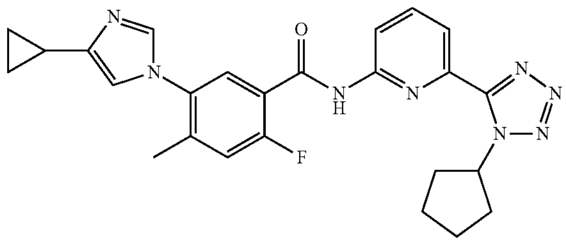 [SMILES: Cc1cc(F)c(C(=O)Nc2cccc(-c3nnnn3C3CCCC3)n2)cc1-n1cnc(C2CC2)c1] | [M − H] 471 | ¹H NMR (400 MHz, DMSO-d₆) δ 11.04 (s, 1H), 8.29 (dd, J = 8.4, 0.9 Hz, 1H), 8.14 (t, J = 8.0 Hz, 1H), 7.99 (dd, J = 7.7, 0.9 Hz, 1H), 7.75-7.59 (m, 2H), 7.51 (d, J = 10.8 Hz, 1H), 7.19 (d, J = 1.4 Hz, 1H), 6.17-5.91 (m, 1H), 2.30-2.20 (m, 3H), 2.08-1.95 (m, 2H), 1.94-1.82 (m, 3H), 1.78-1.67 (m, 2H), 0.83-0.78 (m, 2H), 0.73-0.67 (m, 2H). |
| 9a | 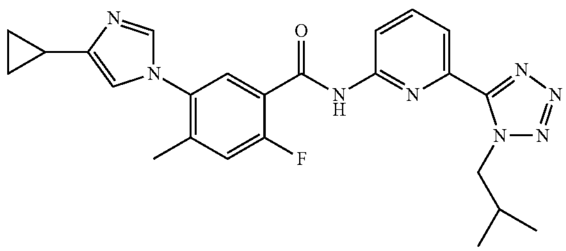 [SMILES: Cc1cc(F)c(C(=O)Nc2cccc(-c3nnnn3CC(C)C)n2)cc1-n1cnc(C2CC2)c1] | [M − H] 459 | ¹H NMR (400 MHz, DMSO-d₆) δ 11.05 (s, 1H), 8.27 (dd, J = 8.3, 1.0 Hz, 1H), 8.14 (t, J = 8.0 Hz, 1H), 8.02 (dd, J = 7.6, 1.0 Hz, 1H), 7.73-7.63 (m, 2H), 7.51 (d, J = 10.9 Hz, 1H), 7.19 (d, J = 1.4 Hz, 1H), 4.93 (d, J = 7.1 Hz, 2H), 2.69 (s, 1H), 2.26 (s, 3H), 2.18-2.05 (m, 1H), 1.88-1.82 (m, 1H), 0.85 (d, J = 7.5 Hz, 6H), 0.83-0.79 (m, 2H), 0.72-0.68 (m, 2H). |
| 10a | 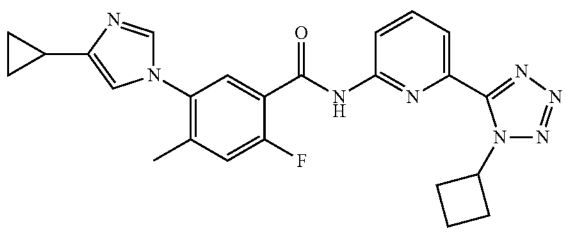 [SMILES: Cc1cc(F)c(C(=O)Nc2cccc(-c3nnnn3C3CCC3)n2)cc1-n1cnc(C2CC2)c1] | [M − H] 457 | ¹H NMR (400 MHz, DMSO-d₆) δ 11.06 (s, 1H), 8.33-8.24 (m, 1H), 8.13 (dd, J = 9.0, 7.0 Hz, 1H), 7.97 (dd, J = 7.6, 0.9 Hz, 1H), 7.75-7.63 (m, 2H), 7.52 (d, J = 10.9 Hz, 1H), 7.20 (d, J = 1.5 Hz, 1H), 6.02 (p, J = 8.3 Hz, 1H), 2.70-2.54 (m, 4H), 1.98-1.77 (m, 3H), 0.83-0.77 (m, 2H), 0.73-0.69 (m, 2H). |
| 11a | 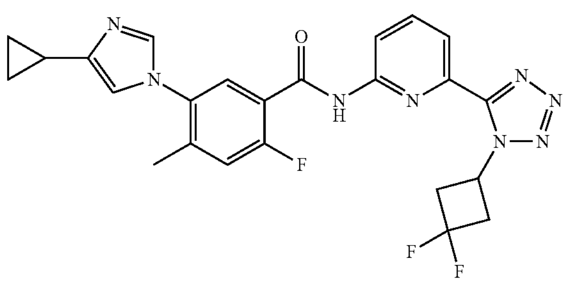 [SMILES: Cc1cc(F)c(C(=O)Nc2cccc(-c3nnnn3C3CC(F)(F)C3)n2)cc1-n1cnc(C2CC2)c1] | [M − H] 493 | ¹H NMR (400 MHz, DMSO-d₆) δ 11.07 (s, 1H), 8.31 (dd, J = 8.3, 1.0 Hz, 1H), 8.15 (dd, J = 8.4, 7.6 Hz, 1H), 8.04 (dd, J = 7.6, 0.9 Hz, 1H), 7.74-7.64 (m, 2H), 7.53 (d, J = 10.8 Hz, 1H), 7.19 (d, J = 1.4 Hz, 1H), 5.99 (br. s, 1H), 3.50-3.25 (m, 4H), 2.26 (s, 3H), 1.85 (tt, J = 8.3, 5.0 Hz, 1H), 0.86-0.75 (m, 2H), 0.79-0.66 (m, 2H). |
| 12a | 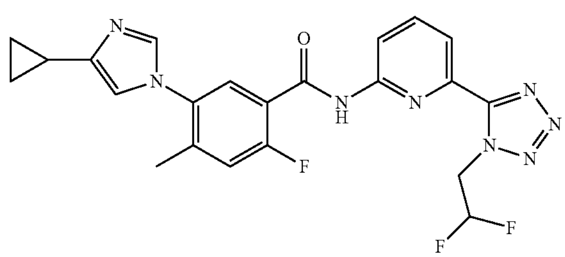 [SMILES: Cc1cc(F)c(C(=O)Nc2cccc(-c3nnnn3CC(F)F)n2)cc1-n1cnc(C2CC2)c1] | [M − H] 467 | ¹H NMR (400 MHz, DMSO-d₆) δ 11.18 (s, 1H), 8.28 (dd, J = 8.4, 1.0 Hz, 1H), 8.15 (dd, J = 8.4, 7.6 Hz, 1H), 8.06 (dd, J = 7.6, 1.0 Hz, 1H), 7.73-7.63 (m, 2H), 7.52 (d, J = 10.8 Hz, 1H), 7.19 (d, J = 1.4 Hz, 1H), 6.57 (tt, J = 70.0, 3.4 Hz, 1H), 5.70 (td, J = 15.1, 3.4 Hz, 2H), 2.26 (s, 3H), 1.89-1.82 (m, 1H), 0.86-0.73 (m, 2H), 0.78-0.66 (m, 2H). |
| 13a | 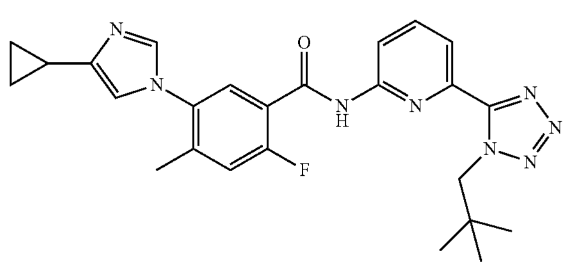 [SMILES: Cc1cc(F)c(C(=O)Nc2cccc(-c3nnnn3CC(C)(C)C)n2)cc1-n1cnc(C2CC2)c1] | [M − H] 473 | ¹H NMR (500 MHz, DMSO-d₆) δ 11.16 (s, 1H), 8.26 (dd, J = 8.4, 0.9 Hz, 1H), 8.13 (dd, J = 8.5, 7.5 Hz, 1H), 8.00 (dd, J = 7.6, 0.9 Hz, 1H), 7.71 (d, J = 1.4 Hz, 1H), 7.65 (d, J = 6.5 Hz, 1H), 7.50 (d, J = 10.8 Hz, 1H), 7.19 (d, J = 1.4 Hz, 1H), 5.04 (s, 2H), 2.26 (s, 3H), 1.85 (tt, J = 8.4, 5.0 Hz, 1H), 0.85-0.77 (m, 11H), 0.76-0.67 (m, 2H). |

-continued

| Example | Structure | LC-MS [M + H]+ unless otherwise noted | H-NMR |
|---|---|---|---|
| 14a | 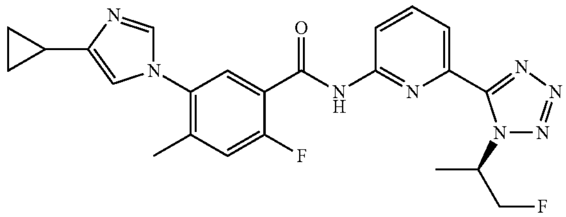 [SMILES: Cc1cc(F)c(C(=O)Nc2cccc(-c3nnnn3[C@H](C)CF)n2)cc1-n1cnc(C2CC2)c1] | 465 | ¹H NMR (400 MHz, Chloroform-d) δ 9.06 (d, J = 15.7 Hz, 1H), 8.45 (dd, J = 8.4, 0.9 Hz, 1H), 8.06 (dd, J = 7.6, 0.9 Hz, 1H), 8.02 (d, J = 7.3 Hz, 1H), 7.94 (t, J = 8.0 Hz, 1H), 7.23-7.12 (m, 1H), 6.03-5.90 (m, 1H), 4.90 (ddd, J = 46.8, 9.6, 7.6 Hz, 1H), 4.69 (ddd, J = 45.9, 9.5, 5.1 Hz, 1H), 2.23 (s, 3H), 1.69 (d, J = 7.0, 3H), 1.75-1.55 (m, 1H), 1.01-0.65 (m, 4H). |
| 15a | 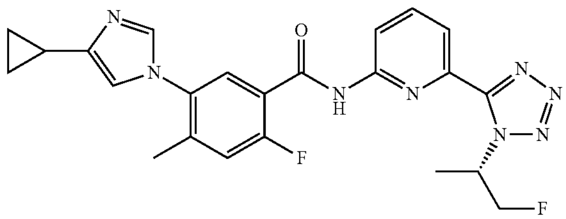 [SMILES: Cc1cc(F)c(C(=O)Nc2cccc(-c3nnnn3[C@@H](C)CF)n2)cc1-n1cnc(C2CC2)c1] | 465 | ¹H NMR (400 MHz, Chloroform-d) δ 9.06 (d, J = 15.7 Hz, 1H), 8.45 (dd, J = 8.4, 0.9 Hz, 1H), 8.06 (dd, J = 7.6, 0.9 Hz, 1H), 8.02 (d, J = 7.3 Hz, 1H), 7.94 (t, J = 8.0 Hz, 1H), 7.23-7.12 (m, 1H), 6.03-5.90 (m, 1H), 4.90 (ddd, J = 46.8, 9.6, 7.6 Hz, 1H), 4.69 (ddd, J = 45.9, 9.5, 5.1 Hz, 1H), 2.23 (s, 3H), 1.69 (d, J = 7.0, 3H), 1.75-1.55 (m, 1H), 1.01-0.65 (m, 4H). |
| 16a | 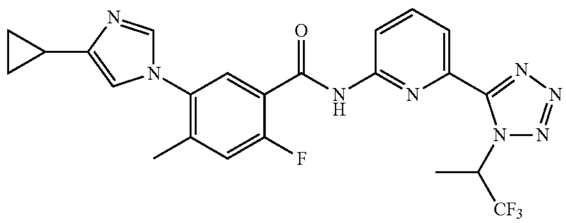 [SMILES: Cc1cc(F)c(C(=O)Nc2cccc(-c3nnnn3C(C)C(F)(F)F)n2)cc1-n1cnc(C2CC2)c1] | 501 | ¹H NMR (400 MHz, Chloroform-d) δ 9.05 (d, J = 16.3 Hz, 1H), 8.46 (d, J = 8.4 Hz, 1H), 8.13 (dd, J = 7.7, 1.0 Hz, 1H), 8.02 (d, J = 7.3 Hz, 1H), 8.00-7.92 (m, 1H), 7.44 (s, 1H), 6.74 (s, 1H), 6.61 (hept, J = 7.0 Hz, 1H), 2.24 (s, 3H), 1.95 (d, J = 7.1 Hz, 3H), 0.92-0.69 (m, 6H). |
| 17a | 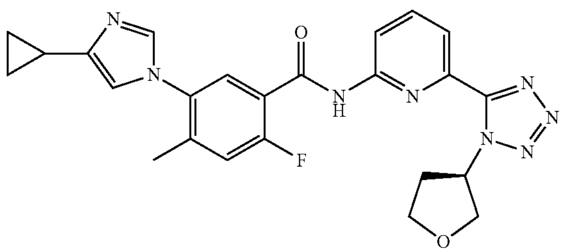 [SMILES: Cc1cc(F)c(C(=O)Nc2cccc(-c3nnnn3[C@@H]3CCOC3)n2)cc1-n1cnc(C2CC2)c1] | 475 | ¹H NMR (400 MHz, Chloroform-d) δ 9.12 (d, J = 16.1 Hz, 1H), 8.53 (s, 1H), 8.15 (d, J = 7.5 Hz, 1H), 8.08 (d, J = 7.5 Hz, 1H), 8.01 (dd, J = 8.0, 8.0 Hz, 1H), 7.45 (d, J = 1.5 Hz, 1H), 7.22 (d, J = 12.5 Hz, 1H), 6.80 (d, J = 1.5 Hz, 1H), 6.08-6.02 (m, 1H), 4.43-4.28 (m, 2H), 4.25-4.08 (m, 2H), 2.82-2.74 (m, 1H), 2.62-2.52 (m, 1H), 2.31 (s, 3H), 1.95-1.88 (m, 1H), 0.93-0.87 (m, 2H), 0.86-0.82 (m, 2H). |
| 18a | 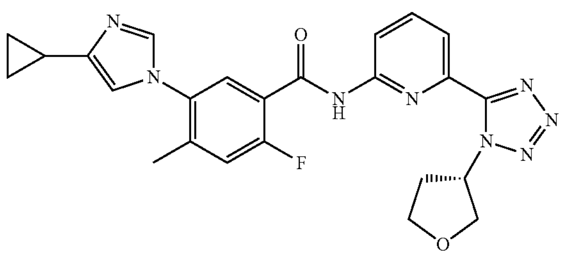 [SMILES: Cc1cc(F)c(C(=O)Nc2cccc(-c3nnnn3[C@H]3CCOC3)n2)cc1-n1cnc(C2CC2)c1] | 475 | ¹H NMR (400 MHz, Chloroform-d) δ 9.15 (d, J = 16.0 Hz, 1H), 8.54 (dd, J = 8.4, 0.9 Hz, 1H), 8.17 (dd, J = 7.6, 0.9 Hz, 1H), 8.11 (d, J = 7.3 Hz, 1H), 8.04 (dd, J = 8.0, 8.0 Hz, 1H), 7.53 (d, J = 1.4 Hz, 1H), 7.25 (d, J = 12.5 Hz, 1H), 6.83 (d, J = 1.4 Hz, 1H), 6.10-6.05 (m, 1H), 4.4-4.34 (m, 2H), 4.23-4.15 (m, 2H), 2.83-2.76 (m, 1H), 2.64-2.54 (m, 1H), 2.33 (s, 3H), 1.98-1.91 (m, 1H), 0.99-0.90 (m, 2H), 0.90-0.80 (m, 2H). |
| 20a | 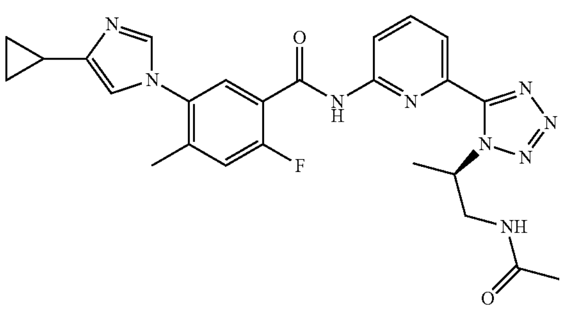 [SMILES: CC(=O)NC[C@@H](C)n1nnnc1-c1cccc(NC(=O)c2cc(-n3cnc(C4CC4)c3)c(C)cc2F)n1] | 504 | ¹H NMR (400 MHz, Chloroform-d) δ 10.05 (d, J = 4.6 Hz, 1H), 8.51 (d, J = 7.9 Hz, 1H), 8.05-7.78 (m, 3H), 7.50 (s, 1H), 7.21 (d, J = 10.9 Hz, 1H), 6.90-6.75 (m, 2H), 6.34-6.10 (m, 1H), 3.93 (ddd, J = 14.0, 6.5, 4.5 Hz, 1H), 3.64 (ddd, J = 14.0, 9.8, 5.8 Hz, 1H), 2.29 (s, 3H), 1.98-1.85 (m, 1H), 1.81 (s, 3H), 1.62 (d, J = 6.9 Hz, 3H), 0.92-0.87 (m, 2H), 0.85-0.74 (m, 2H). |

| Example | Structure | LC-MS [M + H]+ unless otherwise noted | H-NMR |
|---|---|---|---|
| 21a | 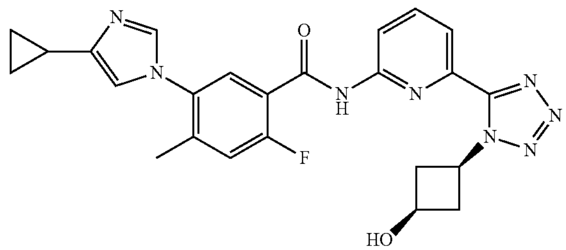 [SMILES: Cc1cc(F)c(C(=O)Nc2cccc(-c3nnnn3[C@H]3C[C@@H](O)C3)n2)cc1-n1cnc(C2CC2)c1] | 475 | ¹H NMR (400 MHz, Chloroform-d) δ 9.21 (d, J = 15.5 Hz, 1H), 8.51 (d, J = 8.4 Hz, 1H), 8.10-8.06 (m, 2H), 7.99 (dd, J = 8.0, 8.0 Hz, 1H), 7.46 (d, J = 1.4 Hz, 1H), 7.23 (d, J = 12.5 Hz, 1H), 6.80 (d, J = 1.4 Hz, 1H), 5.44-5.35 (m, 1H), 4.37-4.32 (m, 1H), 3.23-3.05 (m, 2H), 3.00-2.81 (m, 2H), 2.31 (s, 3H), 1.96-1.88 (m, 1H), 0.94-0.88 (m, 2H), 0.88-0.79 (m, 2H). |
| 22a | 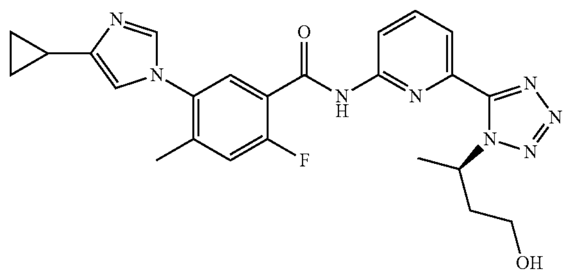 [SMILES: Cc1cc(F)c(C(=O)Nc2cccc(-c3nnnn3[C@H](C)CCO)n2)cc1-n1cnc(C2CC2)c1] | 477 | ¹H NMR (400 MHz, Chloroform-d) δ 9.50 (d, J = 11.8 Hz, 1H), 8.52 (dd, J = 8.0, 1.1 Hz, 1H), 8.07-7.90 (m, 3H), 7.43 (d, J = 1.4 Hz, 1H), 7.18 (d, J = 11.7 Hz, 1H), 6.79 (d, J = 1.3 Hz, 1H), 5.97-5.79 (m, 1H), 3.77 (ddd, J = 11.5, 5.8, 4.3 Hz, 1H), 3.53 (ddd, J = 11.7, 8.5, 3.6 Hz, 1H), 2.48 (dddd, J = 14.4, 9.1, 5.8, 3.6 Hz, 1H), 2.27 (s, 3H), 2.23-2.09 (m, 1H), 1.88 (tt, J = 8.4, 5.0 Hz, 1H), 1.69 (d, J = 6.8 Hz, 3H), 0.95-0.83 (m, 2H), 0.84-0.74 (m, 2H). |
| 23a | 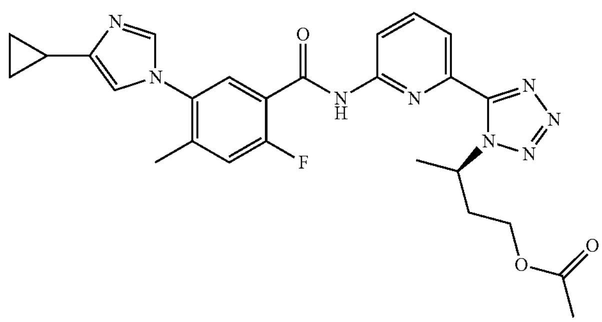 [SMILES: CC(=O)OCC[C@@H](C)n1nnnc1-c1cccc(NC(=O)c2cc(-n3cnc(C4CC4)c3)c(C)cc2F)n1] | 519 | ¹H NMR (400 MHz, Chloroform-d) δ 9.24 (d, J = 13.7 Hz, 1H), 8.53 (d, J = 8.1 Hz, 1H), 8.12-8.03 (m, 2H), 8.03 (t, J = 7.9 Hz, 1H), 7.79 (s, 1H), 7.26 (d, J = 12.1 Hz, 1H), 6.85 (s, 1H), 5.84-5.75 (m, 1H), 4.24-4.18 (m, 1H), 4.08-4.02 (m, 1H), 2.69-2.60 (m, 1H), 2.36-2.27 (m, 1H), 2.33 (s, 3H), 2.03-1.96 (m, 1H), 1.82 (s, 3H), 1.75 (d, J = 6.7 Hz, 3H), 1.02-0.96 (m, 2H), 0.94-0.96 (m, 2H). |
| 24a | 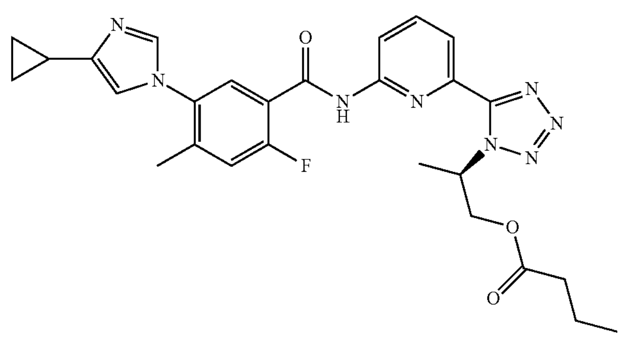 [SMILES: CCCC(=O)OC[C@@H](C)n1nnnc1-c1cccc(NC(=O)c2cc(-n3cnc(C4CC4)c3)c(C)cc2F)n1] | 533 | ¹H NMR (400 MHz, Chloroform-d) δ 9.33 (d, J = 10.4 Hz, 1H), 8.53 (dd, J = 8.3, 0.9 Hz, 1H), 8.14 (dd, J = 7.7, 0.9 Hz, 1H), 8.05-7.93 (m, 2H), 7.49 (d, J = 1.4 Hz, 1H), 7.23 (d, J = 11.6 Hz, 1H), 6.82 (d, J = 1.4 Hz, 1H), 6.23-6.14 (m, 1H), 4.62 (dd, J = 11.3, 5.1 Hz, 1H), 4.50 (dd, J = 11.3, 8.9 Hz, 1H), 2.31 (s, 3H), 2.08-1.99 (m, 2H), 1.95-1.88 (m, 1H), 1.74 (d, J = 6.9 Hz, 3H), 1.38 (tq, J = 14.8, 7.4, 7.0 Hz, 2H), 0.95-0.89 (m, 2H), 0.87-0.83 (m, 2H), 0.76 (t, J = 7.4 Hz, 3H). |
| 25a | 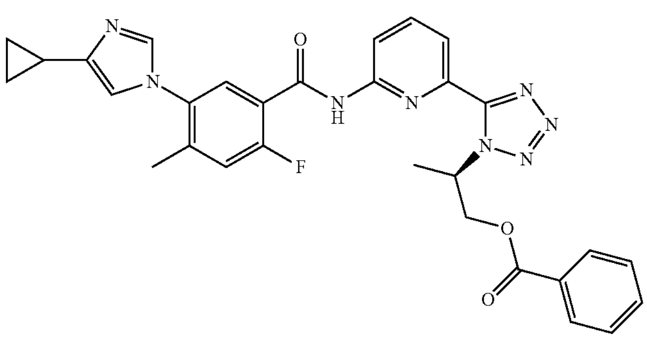 [SMILES: Cc1cc(F)c(C(=O)Nc2cccc(-c3nnnn3[C@H](C)COC(=O)c3ccccc3)n2)cc1-n1cnc(C2CC2)c1] | 567 | ¹H NMR (400 MHz, Chloroform-d) δ 9.30 (d, J = 10.4 Hz, 1H), 8.29 (dd, J = 8.4, 0.9 Hz, 1H), 8.08 (dd, J = 7.7, 0.9 Hz, 1H), 8.02 (d, J = 6.9 Hz, 1H), 7.87-7.79 (m, 1H), 7.75 (s, 1H), 7.66-7.55 (m, 2H), 7.53-7.42 (m, 1H), 7.32-7.21 (m, 3H), 6.86 (d, J = 1.5 Hz, 1H), 6.48-6.31 (m, 1H), 4.91 (dd, J = 11.3, 4.9 Hz, 1H), 4.64 (dd, J = 11.3, 8.9 Hz, 1H), 2.35 (s, 3H), 2.04-1.96 (m, 1H), 1.88 (d, J = 6.9 Hz, 3H), 1.05-0.96 (m, 2H), 0.96-0.89 (m, 2H). |

-continued

| Example | Structure | LC-MS [M + H]+ unless otherwise noted | H-NMR |
|---|---|---|---|
| 26a | 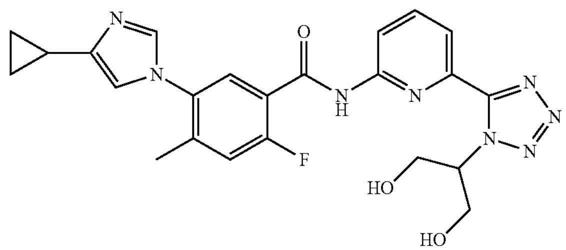 [SMILES: Cc1cc(F)c(C(=O)Nc2cccc(-c3nnnn3C(CO)CO)n2)cc1-n1cnc(C2CC2)c1] | 479 | ¹H NMR (400 MHz, Chloroform-d) δ 9.40 (d, J = 12.6 Hz, 1H), 8.37 (d, J = 8.1 Hz, 1H), 8.08 (d, J = 7.6 Hz, 1H), 8.05-7.92 (m, 2H), 7.57 (d, J = 1.4 Hz, 1H), 7.18 (d, J = 11.8 Hz, 1H), 6.80 (d, J = 1.4 Hz, 1H), 5.81-5.75 (m, 1H), 4.23 (d, J = 5.6 Hz, 4H), 2.28 (s, 3H), 1.94-1.86 (m, 1H), 0.93-0.89 (m, 2H), 0.82-0.78 (m, 2H). |
| 27a | 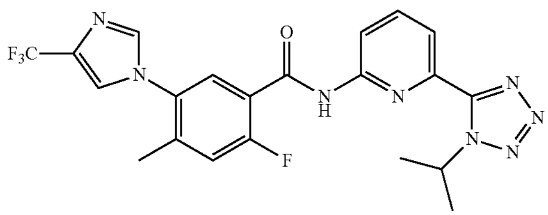 [SMILES: Cc1cc(F)c(C(=O)Nc2cccc(-c3nnnn3C(C)C)n2)cc1-n1cnc(C(F)(F)F)c1] | 475 | ¹H NMR (400 MHz, Chloroform-d) δ 9.14 (d, J = 15.8 Hz, 1H), 8.53 (d, J = 8.3 Hz, 1H), 8.19-8.13 (m, 2H), 8.03 (t, J = 7.8 Hz, 1H), 7.69 (s, 1H), 7.45 (s, 1H), 7.33 (s, 1H), 5.73 (m, 1H), 2.34 (s, 3H), 1.75 (d, J = 6.7 Hz, 6H). |
| 28a | 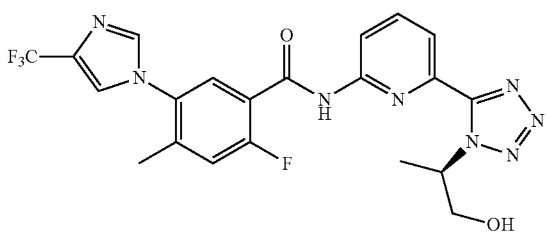 [SMILES: Cc1cc(F)c(C(=O)Nc2cccc(-c3nnnn3[C@H](C)CO)n2)cc1-n1cnc(C(F)(F)F)c1] | 491 | ¹H NMR (400 MHz, Chloroform-d) δ 9.15 (d, J = 15.6 Hz, 1H), 8.47 (d, J = 8.3 Hz, 1H), 8.17-8.14 (m, 2H), 8.04 (t, J = 8.0 Hz, 1H), 7.69 (s, 1H), 7.45 (s, 1H), 7.31 (d, J = 12.2 Hz, 1H), 5.72 (m, 1H), 4.24-4.13 (m, 1H), 2.90 (s, 1H), 2.33 (s, 3H), 1.72 (d, 6.8 Hz, 3H). |
| 32a | 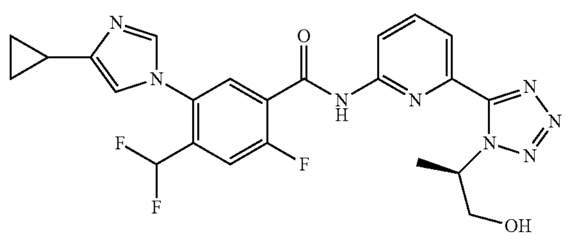 [SMILES: C[C@H](CO)n1nnnc1-c1cccc(NC(=O)c2cc(-n3cnc(C4CC4)c3)c(C(F)F)cc2F)n1] | 499 | ¹H NMR (400 MHz, DMSO-d₆) δ 11.31 (s, 1H), 8.31 (d, J = 8.5 Hz, 1H), 8.15 (t, J = 8.0 Hz, 1H), 7.99 (d, J = 7.6 Hz, 1H), 7.87 (m, 2H), 7.72 (s, 1H), 7.23 (s, 1H), 6.99 (t, J = 53.9 Hz, 1H), 4.92 (s, 2H), 1.54 (d, J = 6.8 Hz, 3H), 0.97-0.78 (m, 2H), 0.72 (dd, J = 5.0, 2.3 Hz, 2H). |
| 34a | 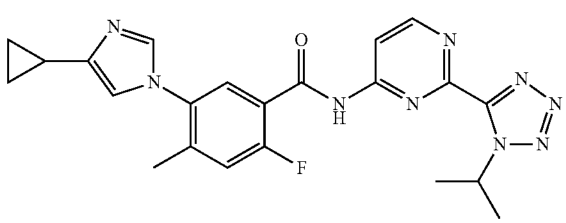 [SMILES: Cc1cc(F)c(C(=O)Nc2ccnc(-c3nnnn3C(C)C)n2)cc1-n1cnc(C2CC2)c1] | 448 | ¹H NMR (400 MHz, Methanol-d₄) δ 8.82 (d, J = 5.8 Hz, 1H), 8.32 (d, J = 5.8 Hz, 1H), 7.68-7.57 (m, 2H), 7.27 (dd, J = 11.0, 0.8 Hz, 1H), 6.95 (d, J = 1.4 Hz, 1H), 5.92-5.74 (m, 1H), 1.85-1.76 (m, 1H), 1.55 (d, J = 14.2 Hz, 6H), 0.84-0.70 (m, 2H), 0.71-0.60 (m, 2H). |
| 35a | 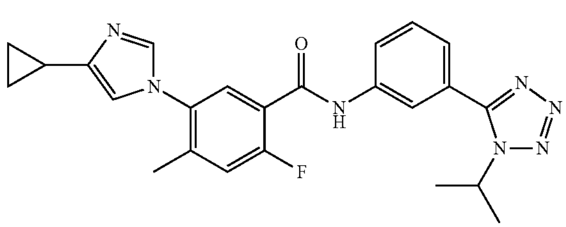 [SMILES: Cc1cc(F)c(C(=O)Nc2cccc(-c3nnnn3C(C)C)c2)cc1-n1cnc(C2CC2)c1] | 446 | ¹H NMR (400 MHz, Chloroform-d) δ 8.73 (d, J = 15.0 Hz, 1H), 8.15 (t, J = 1.9 Hz, 1H), 8.01 (s, 1H), 7.77 (ddd, J = 8.2, 2.2, 1.1 Hz, 1H), 7.58 (t, J = 7.9 Hz, 1H), 7.46 (dd, J = 8.5, 1.4 Hz, 2H), 7.21 (d, J = 12 Hz, 1H), 6.79 (d, J = 1.3 Hz, 1H), 4.93-4.85 (m, 1H), 2.28 (s, 3H), 1.95-1.86 (m, 1H), 1.68 (d, J = 6.1 Hz, 6H), 0.96-0.77 (m, 4H). |

-continued

| Example | Structure | LC-MS [M + H]+ unless otherwise noted | H-NMR |
|---|---|---|---|
| 36a | 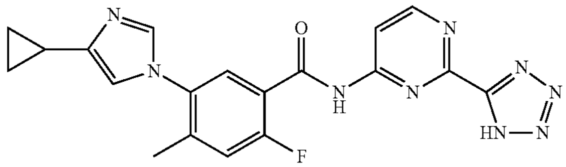 [SMILES: Cc1cc(F)c(C(=O)Nc2ccnc(-c3nnn[nH]3)n2)cc1-n1cnc(C2CC2)c1] | 406 | ¹H NMR (400 MHz, Methanol-d₄) δ 8.80 (s, 1H), 8.24 (d, J = 5.4 Hz, 1H), 7.78-7.71 (m, 2H), 7.37 (d, J = 10.9 Hz, 1H), 7.07 (d, J = 1.4 Hz, 1H), 2.28 (s, 3H), 1.94-1.86 (m, 1H), 0.94-0.82 (m, 2H), 0.79-0.71 (m, 2H). |
| 37a | 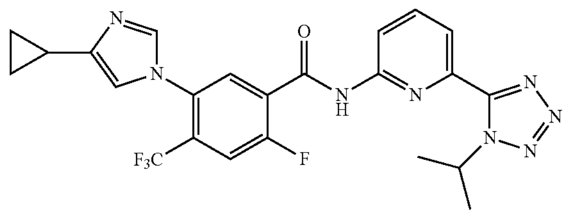 [SMILES: CC(C)n1nnnc1-c1cccc(NC(=O)c2cc(-n3cnc(C4CC4)c3)c(C(F)(F)F)cc2F)n1] | 501 | ¹H NMR (400 MHz, Chloroform-d) δ 9.27 (d, J = 12.4 Hz, 1H), 8.47 (dd, J = 8.4, 0.9 Hz, 1H), 8.25 (d, J = 6.7 Hz, 1H), 8.13 (dd, J = 7.7, 0.9 Hz, 1H), 8.02 (d, J = 16.0 Hz, 0H), 7.88 (s, 1H), 7.72 (d, J = 11.0 Hz, 1H), 6.88 (s, 1H), 5.74 (hept, J = 6.5 Hz, 1H), 1.92 (tt, J = 8.5, 5.1 Hz, 1H), 1.70 (d, J = 6.7 Hz, 6H), 0.98-0.90 (m, 2H), 0.90-0.82 (m, 2H) |
| 38a | 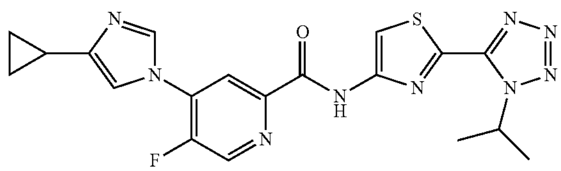 [SMILES: CC(C)n1nnnc1-c1nc(NC(=O)c2cc(-n3cnc(C4CC4)c3)c(F)cn2)cs1] | 440 | ¹H NMR (400 MHz, DMSO-d₆) δ 11.49 (s, 1H), 8.97 (s, 1H), 8.47 (d, J = 6.3 Hz, 1H), 8.28 (s, 1H), 8.22 (s, 1H), 7.71 (s, 1H), 5.95 (m, 1H), 1.91 (m, 1H), 1.63 (d, J = 6.6 Hz, 6H), 0.85 (q, J = 6.9, 3.6 Hz, 2H), 0.76 (q, J = 6.9, 3.6 Hz, 2H). |
| 39a | 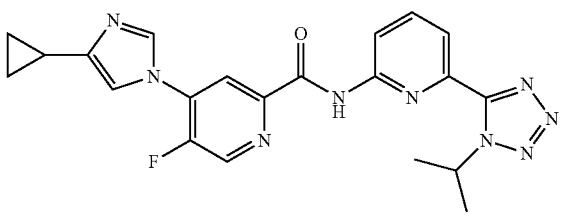 [SMILES: CC(C)n1nnnc1-c1cccc(NC(=O)c2cc(-n3cnc(C4CC4)c3)c(F)cn2)n1] | 434 | ¹H NMR (400 MHz, Chloroform-d) δ 10.31 (s, 1H), 8.71 (d, J = 2.9 Hz, 1H), 8.58 (dd, J = 8.3, 1.0 Hz, 1H), 8.42 (d, J = 6.4 Hz, 1H), 8.13 (dd, J = 7.6, 1.0 Hz, 1H), 8.07-8.02 (m, 2H), 5.84 (m, 1H), 1.98 (m, 1H), 1.76 (d, J = 6.7 Hz, 6H), 0.96 (m, 2H), 0.91 (m, 2H). |
| 40a | 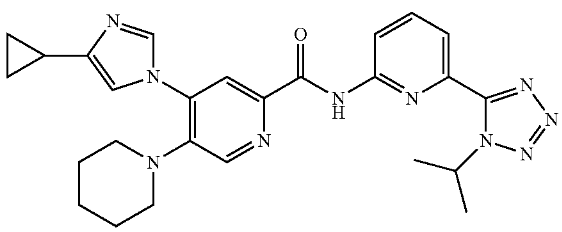 [SMILES: CC(C)n1nnnc1-c1cccc(NC(=O)c2cc(-n3cnc(C4CC4)c3)c(N3CCCCC3)cn2)n1] | 499 | ¹H NMR (400 MHz, Chloroform-d) δ 10.35 (s, 1H), 8.58 (d, J = 8.3 Hz, 1H), 8.43 (s, 1H), 8.10-8.07 (m, 3H), 8.00 (t, J = 8.0 Hz, 1H), 7.20 (s, 1H), 5.84 (m, 1H), 2.93 (t, J = 5.2 Hz, 4H), 1.98 (m, 1H), 1.75 (d, J = 6.6 Hz, 6H), 1.70 (m, 4H), 1.65 (m, 2H), 0.95 (m, 2H), 0.85 (m, 2H). |
| 41a | 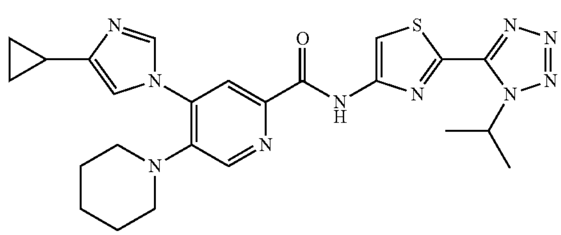 | 505 | ¹H NMR (400 MHz, Chloroform-d) δ 10.53 (s, 1H), 8.41 (s, 1H), 8.15 (s, 1H), 8.11-8.03 (m, 2H), 7.19 (s, 1H), 5.87 m, 1H), 2.92 (t, J = 5.2 Hz, 4H), 2.00 (m, 1H), 1.74 (d, J = 6.7 Hz, 6H), 1.69-1.57 (m, 6H), 0.90 (q, J = 6.8, 4.0 Hz, 2H), 0.81 (q, J = 6.8, 4.0 Hz, 2H). |
| 42a | 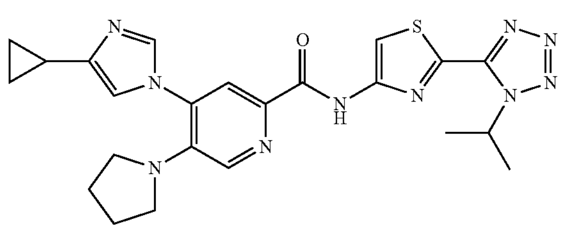 [SMILES: CC(C)n1nnnc1-c1nc(NC(=O)c2cc(-n3cnc(C4CC4)c3)c(N3CCCC3)cn2)cs1] | 491 | ¹H NMR (400 MHz, Chloroform-d) δ 10.43 (s, 1H), 8.25 (s, 1H), 8.12 (s, 1H), 8.00 (s, 1H), 7.68 (s, 1H), 6.93 (s, 1H), 5.88 (m, 1H), 3.16 (d, J = 6.0 Hz, 4H), 1.95-1.91 (m, 5H), 1.74 (d, J = 6.7 Hz, 6H), 0.97 (q, J = 7.8, 3.5 Hz, 2H), 0.88 (q, J = 7.8, 3.5 Hz, 2H). |

-continued

| Example | Structure | LC-MS [M + H]+ unless otherwise noted | H-NMR |
|---|---|---|---|
| 43a | 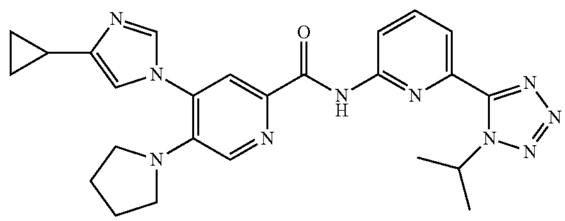 [SMILES: CC(C)n1nnnc1-c1cccc(NC(=O)c2cc(-n3cnc(C4CC4)c3)c(N3CCCC3)cn2)n1] | 485 | ¹H NMR (400 MHz, Chloroform-d) δ 10.25 (s, 1H), 8.58 (d, J = 8.3 Hz, 1H), 8.24 (s, 1H), 8.06 (d, J = 7.5 Hz, 1H), 8.01-7.96 (m, 2H), 7.57 (s, 1H), 6.91 (s, 1H), 5.86 (m, 1H), 3.6 (t, J = 6.4 Hz, 4H), 1.94 (t, J = 6.4 Hz, 4H), 1.90 (m, 1H), 1.75 (d, J = 6.7 Hz, 6H), 0.93 (m, 2H), 0.88 (m, 2H). |
| 44a | 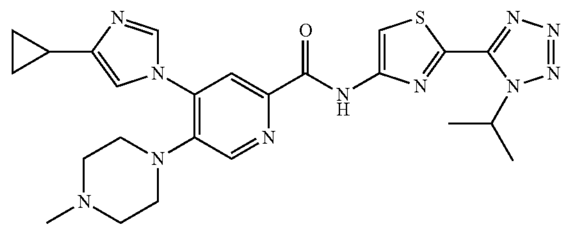 [SMILES: CC(C)n1nnnc1-c1nc(NC(=O)c2cc(-n3cnc(C4CC4)c3)c(N3CCN(C)CC3)cn2)cs1] | 520 | ¹H NMR (400 MHz, Chloroform-d) δ 10.54 (s, 1H), 8.44 (s, 1H), 8.15 (s, 1H), 8.11 (s, 1H), 8.06 (s, 1H), 7.16 (s, 1H), 5.87 (m, 1H), 3.02 (s, 4H), 2.61 (s, 4H), 2.41 (s, 3H), 1.96 (m, 1H), 1.74 (d, J = 6.7 Hz, 6H), 0.96 (q, J = 8.1, 3.0 Hz, 2H), 0.81 (q, J = 8.1, 3.0 Hz, 2H). |
| 45a | 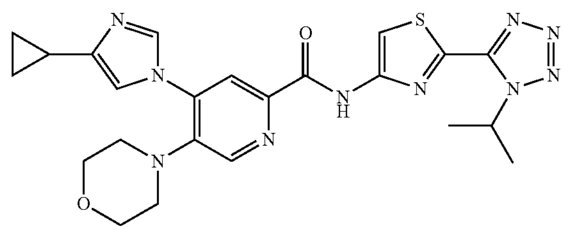 [SMILES: CC(C)n1nnnc1-c1nc(NC(=O)c2cc(-n3cnc(C4CC4)c3)c(N3CCOCC3)cn2)cs1] | 507 | ¹H NMR (400 MHz, Chloroform-d) δ 10.53 (s, 1H), 8.44 (s, 1H), 8.15 (s, 1H), 8.13 (s, 1H), 8.09 (s, 1H), 7.20 (s, 1H), 5.86 (m, 1H), 3.82 (t, J = 4.5 Hz, 4H), 2.95 (t, J = 4.5 Hz, 4H), 1.97 (m, 1H), 1.74 (d, J = 6.7 Hz, 6H), m 1.00 (q, J = 6.8, 4.2 Hz, 2H), 0.87 (q, J = 6.8, 4.2 Hz, 2H). |
| 46a | 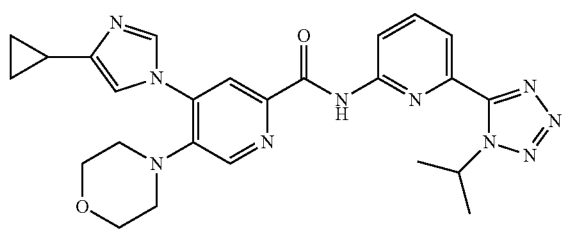 | 501 | ¹H NMR (400 MHz, Chloroform-d) δ 10.33 (s, 1H), 8.58 (dd, J = 8.3, 1.0 Hz, 1H), 8.44 (s, 1H), 8.14 (s, 1H), 8.10 (dd, J = 8.3, 1.0 Hz, 2H), 8.04-8.00 (m, 2H), 7.20 (d, J = 1.4 Hz, 1H), 5.84 (m, 1H), 3.82 (t, J = 4.4 Hz, 4H), 2.95 (t, J = 4.4 Hz, 4H), 1.96 (m, 1H), 1.75 (d, J = 6.7 Hz, 6H), 0.95 (m, 2H), 0.86 (m, 2H). |
| 47a | 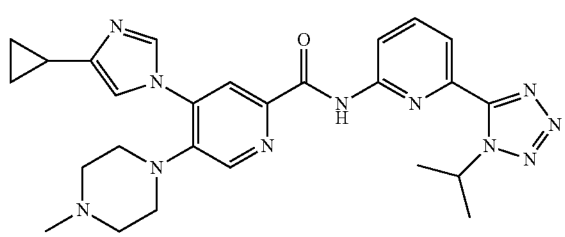 [SMILES: CC(C)n1nnnc1-c1cccc(NC(=O)c2cc(-n3cnc(C4CC4)c3)c(N3CCN(C)CC3)cn2)n1] | 514 | ¹H NMR (400 MHz, Chloroform-d) δ 10.34 (s, 1H), 8.58 (dd, J = 8.3, 1.0 Hz, 1H), 8.45 (s, 1H), 8.11-8.09 (m, 2H), 8.04-7.98 (m, 2H), 7.17 (d, J = 1.4 Hz, 1H), 5.85 (m, 1H), 3.01 (t, J = 5.1 Hz, 4H), 2.57 (t, J = 5.1 Hz, 4H), 2.38 (s, 3H), 1.96 (m, 1H), 1.75 (d, J = 6.7 Hz, 6H), 0.94 (m, 2H), 0.85 (m, 2H). |
| 48a | 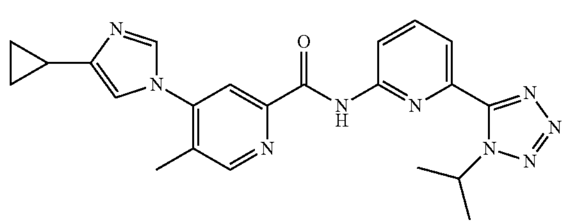 [SMILES: Cc1cnc(C(=O)Nc2cccc(-c3nnnn3C(C)C)n2)cc1-n1cnc(C2CC2)c1] | 430 | ¹H NMR (400 MHz, Chloroform-d) δ 10.43 (s, 1H), 8.69 (s, 1H), 8.59 (dd, J = 8.0, 1.0 Hz, 1H), 8.19 (s, 1H), 8.11 (dd, J = 8.0, 1.0 Hz, 1H), 8.02 (t, J = 8.0 Hz, 1H), 7.70 (s, 1H), 6.98 (s, 1H), 5.84 (m, 1H), 2.49 (s, 3H), 1.95 (m, 1H), 1.76 (d, J = 6.7 Hz, 6H), 0.95 (m, 2H), 0.89 (m, 2H). |

-continued

| Example | Structure | LC-MS [M + H]+ unless otherwise noted | H-NMR |
|---|---|---|---|
| 49a | 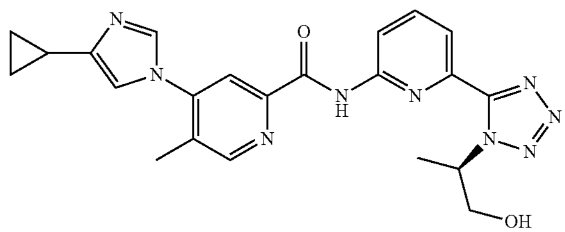 [SMILES: Cc1cnc(C(=O)Nc2cccc(-c3nnnn3[C@H](C)CO)n2)cc1-n1cnc(C2CC2)c1] | 446 | ¹H NMR (400 MHz, DMSO-d$_6$) δ 8.83 (s, 1H), 8.40 (dd, J = 8.4, 1.0 Hz, 1H), 8.17 (t, J = 8.4 Hz, 1H), 8.08 (s, 1H), 8.01-7.98 (m, 2H), 7.45 (s, 1H), 5.87 (m, 1H), 3.78 (m, 2H), 2.45 (s, 3H), 1.89 (m, 1H), 1.60 (d, J = 6.8 Hz, 3H), 0.84 (m, 2H), 0.74 (m, 2H). |
| 50a | 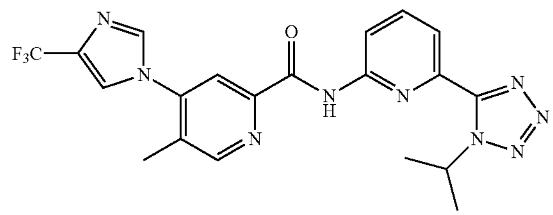 [SMILES: Cc1cnc(C(=O)Nc2cccc(-c3nnnn3C(C)C)n2)cc1-n1cnc(C(F)(F)F)c1] | 458 | ¹H NMR (400 MHz, Chloroform-d) δ 10.39 (s, 1H), 8.79 (s, 1H), 8.59 (d, J = 8.2 Hz, 1H), 8.26 (s, 1H), 8.13 (d, J = 7.5 Hz, 1H), 8.03 (t, J = 8.0 Hz, 1H), 7.83 (s, 1H), 7.59 (s, 1H), 5.83 (m, 1H), 2.49 (s, 3H), 1.76 (d, J = 6.7 Hz, 6H). |
| 51a | 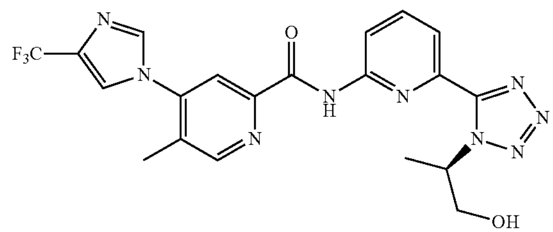 [SMILES: Cc1cnc(C(=O)Nc2cccc(-c3nnnn3[C@H](C)CO)n2)cc1-n1cnc(C(F)(F)F)c1] | 474 | ¹H NMR (400 MHz, Chloroform-d) δ 10.40 (s, 1H), 8.76 (s, 1H), 8.42 (d, J = 8.4 Hz, 1H), 8.25 (s, 1H), 8.14 (d, J = 7.7 Hz, 1H), 8.03 (t, J = 8.0 Hz, 1H), 7.84 (s, 1H), 7.59 (s, 1H), 5.88 (m, 1H), 4.20 (m, 2H), 3.16 (s, 1H), 2.49 (s, 3H), 1.73 (d, J = 6.8 Hz, 3H). |
| 52a | 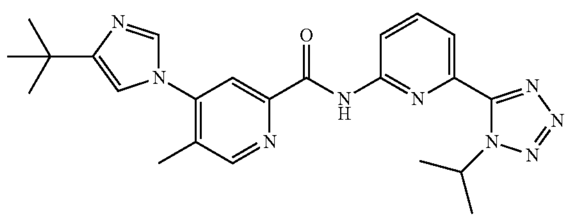 [SMILES: Cc1cnc(C(=O)Nc2cccc(-c3nnnn3C(C)C)n2)cc1-n1cnc(C(C)(C)C)c1] | 446 | ¹H NMR (400 MHz, Chloroform-d) δ 10.45 (s, 1H), 8.70 (s, 1H), 8.60 (d, J = 8.3 Hz, 1H), 8.22 (s, 1H), 8.12 (d, J = 7.5 Hz, 1H), 8.03 (t, J = 8.0 Hz, 1H), 7.74 (s, 1H), 6.95 (s, 1H), 5.86 (m, 1H), 2.51 (s, 3H), 1.76 (d, J = 6.7 Hz, 6H), 1.39 (s, 9H). |
| 53a | 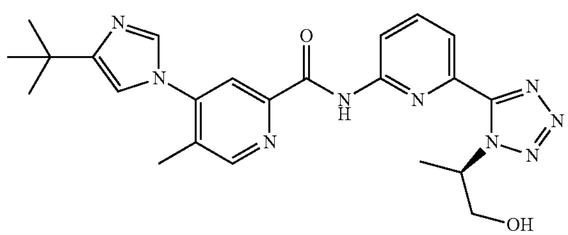 [SMILES: Cc1cnc(C(=O)Nc2cccc(-c3nnnn3[C@H](C)CO)n2)cc1-n1cnc(C(C)(C)C)c1] | 462 | ¹H NMR (400 MHz, Chloroform-d) δ 10.48 (s, 1H), 8.69 (s, 1H), 8.43 (d, J = 8.3 Hz, 1H), 8.22 (s, 1H), 8.15 (d, J = 7.6 Hz, 1H), 8.04 (t, J = 7.9 Hz, 1H), 7.75 (s, 1H), 6.95 (s, 1H), 5.88 (m, 1H), 4.20 (m, 2H), 2.51 (s, 3H), 1.74 (d, J = 6.8 Hz, 3H), 1.39 (s, 9H). |
| 54a | 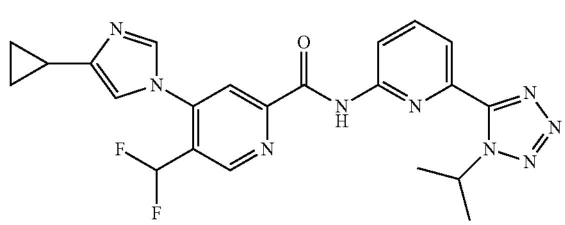 [SMILES: CC(C)n1nnnc1-c1cccc(NC(=O)c2cc(-n3cnc(C4CC4)c3)c(C(F)F)cn2)n1] | 466 | ¹H NMR (400 MHz, Chloroform-d) δ 10.43 (s, 1H), 9.17 (s, 1H), 8.60 (d, J = 8.3 Hz, 1H), 8.34 (s, 1H), 8.16 (d, J = 7.6 Hz, 1H), 8.05 (t, J = 8.0 Hz, 1H), 7.73 (s, 1H), 7.09 (s, 1H), 6.81 (t, J = 53.2 Hz, 1H), 5.85 (m, 1H), 1.96 (m, 1H), 1.77 (d, J = 6.7 Hz, 6H), 0.96 (m, 2H), 0.91 (m, 2H). |

-continued

| Example | Structure | LC-MS [M + H]+ unless otherwise noted | H-NMR |
|---------|-----------|---------------------------------------|-------|
| 55a | 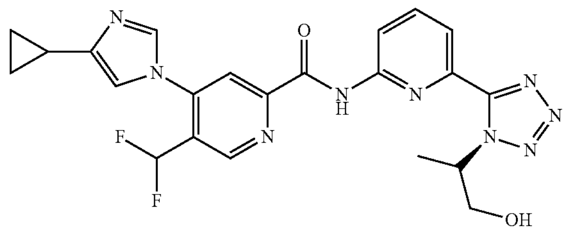 | 482 | $^1$H NMR (400 MHz, Chloroform-d) δ 10.45 (s, 1H), 9.15 (s, 1H), 8.44 (d, J = 8.3 Hz, 1H), 8.33 (s, 1H), 8.17 (d, J = 7.6 Hz, 1H), 8.05 (t, J = 8.0 Hz, 1H), 7.72 (s, 1H), 7.08 (s, 1H), 6.81 (t, J = 53.2 Hz, 1H), 5.89 (m, 1H), 4.19 (m, 2H), 3.04 (s, 1H), 1.95 (m, 1H), 1.73 (d, J = 6.8 Hz, 3H), 0.97 (m, 2H), 0.89 (m, 2H). |
| 56a | 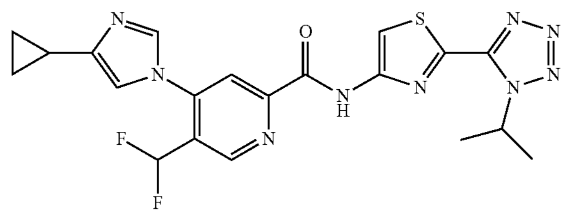 [SMILES: CC(C)n1nnnc1-c1nc(NC(=O)c2cc(-n3cnc(C4CC4)c3)c(C(F)F)cn2)cs1] | 472 | $^1$H NMR (400 MHz, Chloroform-d) δ 10.65 (s, 1H), 9.14 (s, 1H), 8.32 (s, 1H), 8.21 (s, 1H), 7.78 (s, 1H), 7.09 (s, 1H), 6.82 (t, J = 53.2 Hz, 1H), 5.87 (m, 1H), 1.97 (m, 1H), 1.76 (d, J = 6.7 Hz, 6H), 0.98 (m, 2H), 0.90 (m, 2H). |
| 57a | 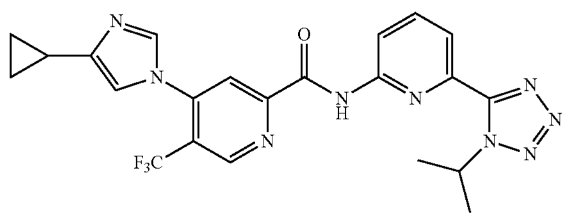 | 484 | $^1$H NMR (400 MHz, Chloroform-d) δ 10.35 (s, 1H), 9.18 (s, 1H), 8.58 (d, J = 8.4 Hz, 1H), 8.38 (s, 1H), 8.17 (d, J = 8.4 Hz, 1H), 8.11 (s, 1H), 8.07 (t, J = 8.4 Hz, 1H), 7.84 (s, 1H), 7.04 (s, 1H), 5.83 (m, 1H), 1.97 (m, my 1.76 (d, J = 6.5 Hz, 6H), 0.99 (m, 2H), 0.90 (m, 2H). |
| 58a | 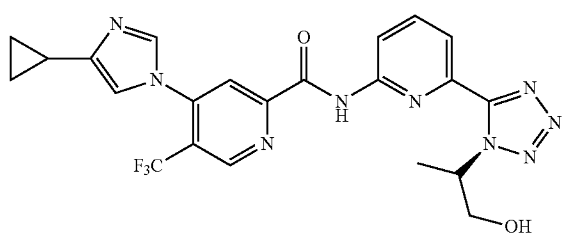 | 500 | $^1$H NMR (400 MHz, Chloroform-d) δ 10.39 (s, 1H), 9.16 (s, 1H), 8.45 (dd, J = 8.3, 1.0 Hz, 1H), 8.37 (s, 1H), 8.19 (dd, J = 8.3, 1.0 Hz, 1H), 8.06 (t, J = 8.3 Hz, 1H), 7.80 (s, 1H), 7.05 (s, 1H), 5.87 (m, 1H), 4.20 (m, 2H), 1.97 (m, 1H) 1.73 (d, J = 6.8 Hz, 3H), 0.99 (m, 2H), 0.93 (m, 2H). |
| 59a | 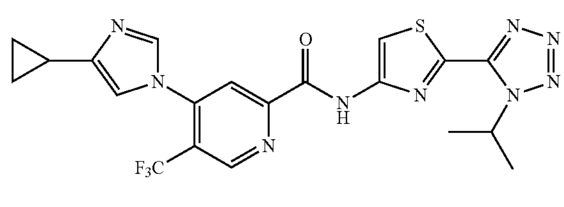 [SMILES: CC(C)n1nnnc1-c1nc(NC(=O)c2cc(-n3cnc(C4CC4)c3)c(C(F)(F)F)cn2)cs1] | 490 | $^1$H NMR (400 MHz, Chloroform-d) δ 10.60 (s, 1H), 9.13 (s, 1H), 8.35 (s, 1H), 8.21 (s, 1H), 7.70 (s, 1H), 7.28 (s, 1H), 7.04 (s, 1H), 5.85 (m, 1H), 1.95 (m, 1H), 1.75 (d, J = 6.7 Hz, 6H), 0.96 (m, 2H), 0.89 (m, 2H). |
| 60a | 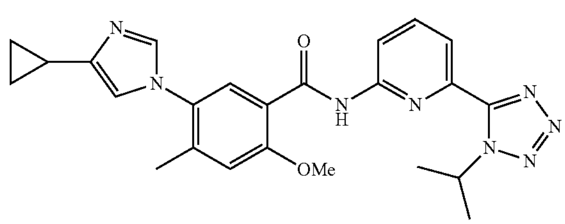 [SMILES: COc1cc(C)c(-n2cnc(C3CC3)c2)cc1C(=O)Nc1cccc(-c2nnnn2C(C)C)n1] | 459 | |

| Example | Structure | LC-MS [M + H]+ unless otherwise noted | H-NMR |
|---|---|---|---|
| 61a | 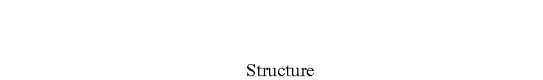 | 475 | |

Example 1b

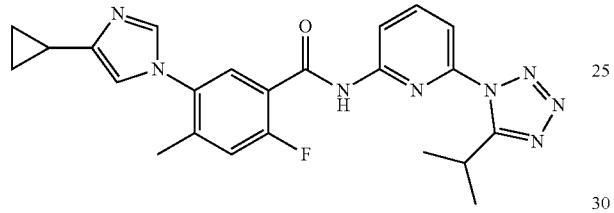

Step 1: Synthesis of 6-(5-isopropyl-1H-tetrazol-1-yl)pyridin-2-amine (compound 1b)

Route 1 for Step 1:

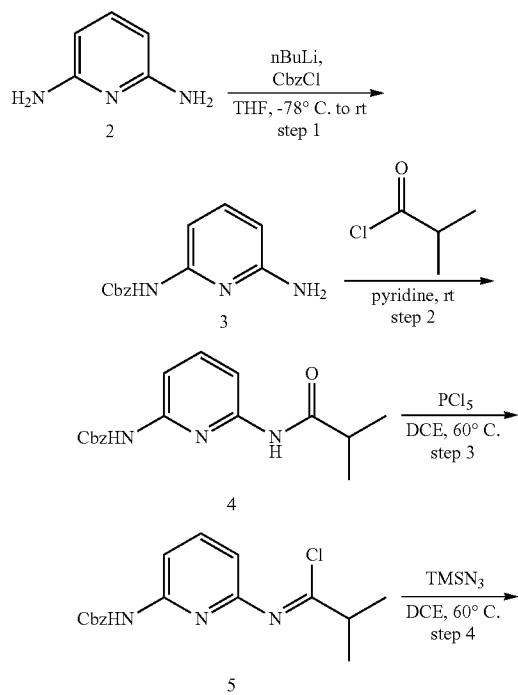

Step 1-1a. Synthesis of benzyl (6-aminopyridin-2-yl) carbamate (compound 3)

To a solution of pyridine-2,6-diamine (1.017 g, 9.32 mmol) in THF (23 mL) was slowly added 1.0 M nBuLi solution in hexane (6.41 mL, 10.25 mmol) at −78° C. The reaction was allowed to stir at the same temperature for one hour before addition of CbzCl (1.38 mL, 9.32 mmol). Then the reaction was allowed to slowly warm to room temperature and stir for additional two hours. The reaction was quenched with aq. NH$_4$Cl solution. The aqueous layer was extracted with EtOAc. The combined organic layers were dried over Na$_2$SO$_4$ and concentrated. The residue was purified by chromatography on silica gel using 0→100% EtOAc in hexanes to afford 0.93 g oil as the compound 3 (41% yield). $^1$H NMR (400 MHz, Chloroform-d) δ 7.53-7.26 (m, 8H), 6.19 (d, J=8.0 Hz, 1H), 5.20 (s, 2H), 4.38 (br, 3H).

Step 1-2a. Synthesis of benzyl (6-isobutyramidopyridin-2-yl)carbamate (compound 4)

To a solution of benzyl (6-aminopyridin-2-yl)carbamate (0.93 g, 3.82 mmol) in pyridine (13 mL) at room temperature was added isobutyryl chloride (0.48 mL, 4.59 mmol) dropwise. The reaction was allowed to stir for two hours. Concentrate and purified by 40 g column with 0→100%

EtOAc in hex to afford 0.984 mg white solid as compound 4 (82% yield). LC-MS (m/z): M+1=314.13, calcd. 314.14.

Step 1-3a and 1-4a. Synthesis of benzyl (6-(5-isopropyl-1H-tetrazol-1-yl)pyridin-2-yl)carbamate (compound 6)

To a solution of benzyl (6-isobutyramidopyridin-2-yl)carbamate (666 mg, 2.13 mmol) in DCE (11 mL) was added PCl$_5$ (531 mg, 2.55 mmol). The resulting clear solution was allowed to stir at 60° C. for overnight to afford a cloudy pale yellow solution. Concentrate to afford pale yellow solid as the compound 5. The crude was directly used in the step 4 without any purification.

To a solution of the resulting compound 5 (554 mg, 1.67 mmol) in DCE (8 mL) was added TMSN$_3$ (0.43 mL, 3.34 mmol). The resulting cloudy solution was allowed to stir at 60° C. for overnight. The crude was quenched with NaHCO$_3$ aq. solution. The aqueous layer was extracted with EtOAc. The combined organic layers were dried over Na$_2$SO$_4$ and concentrated. The residue was purified by chromatography on silica gel using 0→30% EtOAc in hexanes to afford 369.3 mg white solid as the compound 6 (65% yield). LC-MS (m/z): M+1=339.14, calcd. 339.15. $^1$H NMR (400 MHz, Chloroform-d) δ 8.14 (d, J=8.3 Hz, 1H), 7.96 (t, J=8.1 Hz, 1H), 7.60 (dd, J=7.8, 0.8 Hz, 1H), 7.46-7.35 (m, 5H), 7.31 (br, 1H), 5.26 (s, 2H), 3.85 (p, J=6.9 Hz, 1H), 1.43 (d, J=6.9 Hz, 6H).

Step 1-5a. Synthesis of 6-(5-isopropyl-1H-tetrazol-1-yl)pyridin-2-amine (compound 1b)

To a solution of benzyl (6-(5-isopropyl-1H-tetrazol-1-yl)pyridin-2-yl)carbamate (421 mg, 1.24 mmol) in EtOH (6.2 mL) was added Pd/C (21 mg). The reaction was purged with H$_2$ for 3 times and stir at room temperature under 1 atm H$_2$ for overnight. Filter through a Celite plug and concentrate. The crude was then purified by chromatography on silica gel using 0→5% MeOH in DCM to afford 218.6 mg white solid as the compound 1b (86% yield). LC-MS (m/z): M+1=205.10, calcd. 205.11. $^1$H NMR (400 MHz, Chloroform-d) δ 7.71-7.61 (m, 1H), 7.18 (dd, J=7.7, 0.7 Hz, 1H), 6.59 (dd, J=8.2, 0.7 Hz, 1H), 4.62 (s, 2H), 3.89 (p, J=6.9 Hz, 1H), 1.44 (d, J=7.0 Hz, 6H).

Route 2 for Step 1:

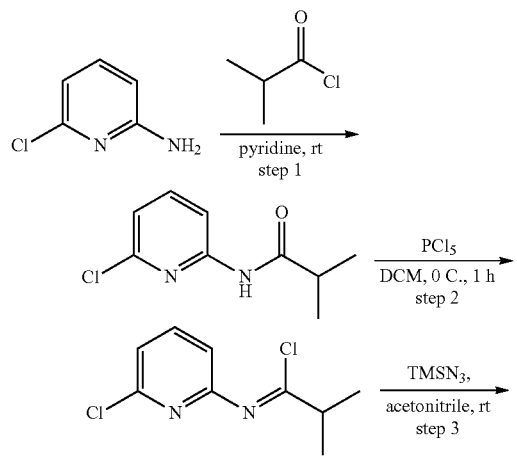

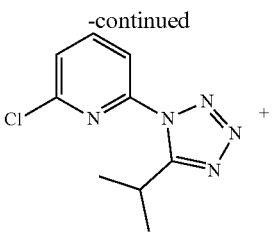

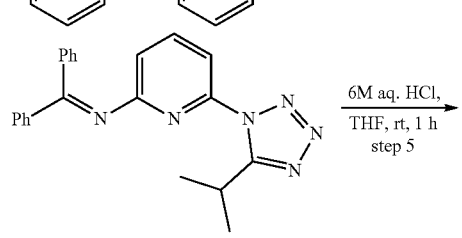

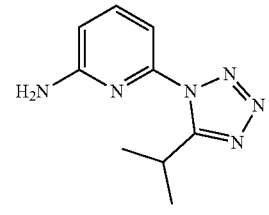

Step 1-1b: synthesis of N-(6-chloropyridin-2-yl)isobutyramide

To a solution of 6-chloropyridin-2-amine (1.04 g, 8.09 mmol) in pyridine/DCM (16.4 mL, 1/4) was added isobutyryl chloride (0.91 mL, 8.49 mmol) dropwise at 0° C. The reaction was allowed to stir at 0° C. for 30 min and then rt for 1 h. The crude reaction was diluted with DCM and washed with aq. NH$_4$Cl and brine. The organic layer was then dried over Na$_2$SO$_4$, filtered and concentrated. The crude residue was purified by chromatography on silica gel (0→20% acetone in hexanes) to provide N-(6-chloropyridin-2-yl)isobutyramide as white solid (1.523 g, 95%). $^1$H NMR (500 MHz, Chloroform-d) δ 8.19 (d, J=8.2 Hz, 1H), 7.85 (s, br, 1H), 7.68 (t, J=8.0 Hz, 1H), 7.08 (d, J=7.8 Hz, 1H), 2.62-2.48 (m, 1H), 1.29 (d, J=6.9 Hz, 6H).

Step 1-2b: synthesis of (Z)—N-(6-chloropyridin-2-yl)isobutyrimidoyl chloride To a solution of N-(6-chloropyridin-2-yl)isobutyramide (1.523 g, 7.67 mmol) in DCM (38 mL) was added PCl$_5$ (1.764 g, 8.05 mmol). The resulting clear solution was allowed to stir at rt for 1 hour. The crude was concentrated and directly used in the step 3 without any purification.

Step 1-3b: synthesis of 2-chloro-6-(5-isopropyl-1H-tetrazol-1-yl)pyridine

To a solution of (Z)—N-(6-chloropyridin-2-yl)isobutyrimidoyl chloride (0.887 g, 4.09 mmol) in MeCN (10.2 mL) was added TMSN$_3$ (1.09 mL, 8.17 mmol). The reaction was allowed to stir at 60° C. for 2 days. The crude was cooled to rt, quenched with aq. NaHCO$_3$ and extracted with EtOAc (×3). The combined organic layers were washed with brine, dried over Na$_2$SO$_4$, filtered and concentrated. The crude residue was purified by chromatography on silica gel (0→30% EtOAc in hexanes) to afford 2-chloro-6-(5-isopropyl-1H-tetrazol-1-yl)pyridine as white solid (396 mg, 43% yield). $^1$H NMR (400 MHz, Chloroform-d) δ 8.00-7.93 (m, 2H), 7.56-7.43 (m, 1H), 4.06-3.94 (m, 1H), 1.51 (d, J=6.9 Hz, 6H).

Step 1-4b: synthesis of N-(6-(5-isopropyl-1H-tetrazol-1-yl)pyridin-2-yl)-1,1-diphenylmethanimine To a solution of 2-chloro-6-(5-isopropyl-1H-tetrazol-1-yl)pyridine (102 mg, 0.456 mmol) in toluene (2.3 mL) was added diphenylmethanimine (0.115 mL, 0.685 mmol), tris(dibenzylideneacetone)dipalladium(0) (20.9 mg, 0.023 mmol), BINAP (28.4 mg, 0.046 mmol) and sodium tert-butoxide (65.8 mg, 0.685 mmol). The reaction was allowed to stir at 60° C. for overnight. The reaction was quenched with aq. NaHCO$_3$, and extracted with EtOAc (×3). The combined organic layers were washed with brine, dried over Na$_2$SO$_4$, filtered and concentrated. The crude residue was purified by chromatography on silica gel (0→20% EtOAc in hexanes) to afford N-(6-(5-isopropyl-1H-tetrazol-1-yl)pyridin-2-yl)-1,1-diphenylmethanimine as off white solid (112.4 mg, 67% yield). LC-MS [M+H]=369.16.

Step 1-5b: synthesis of 6-(5-isopropyl-1H-tetrazol-1-yl)pyridin-2-amine

To a solution of N-(6-(5-isopropyl-1H-tetrazol-1-yl)pyridin-2-yl)-1,1-diphenylmethanimine (112.4 mg, 0.305 mmol) in THF (1.5 mL) was added aq. HCl solution (6N, 0.763 mL). the reaction was then allowed to stir at rt for 1 hour. The reaction was quenched with aq. NaHCO$_3$, and extracted with EtOAc (×3). The combined organic layers were washed with brine, dried over Na$_2$SO$_4$, filtered and concentrated. The crude residue was purified by chromatography on silica gel (0→60% EtOAc in hexanes) to afford 6-(5-isopropyl-1H-tetrazol-1-yl)pyridin-2-amine as white solid (47 mg, 75% yield).

Step 2: Synthesis of 5-(4-cyclopropyl-1H-imidazol-1-yl)-2-fluoro-N-(6-(5-isopropyl-1H-tetrazol-1-yl)pyridin-2-yl)-4-methylbenzamide (Example 1b)

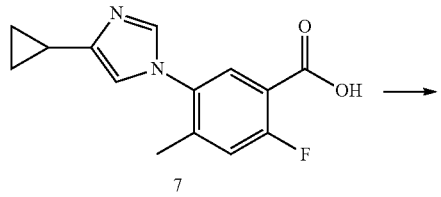

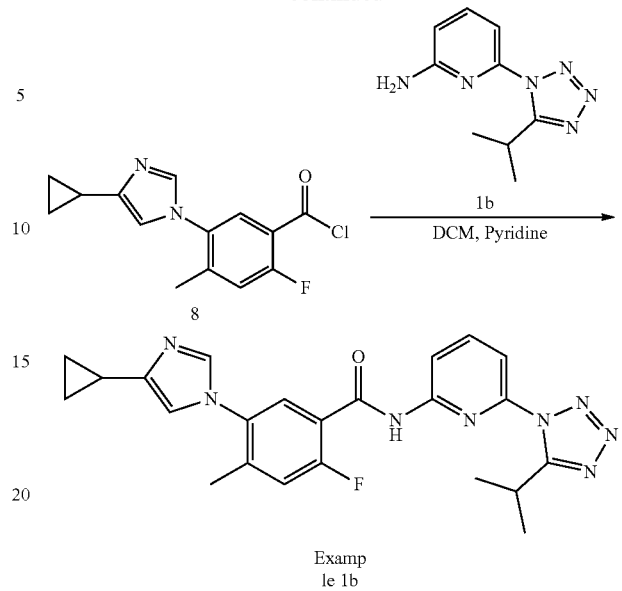

Example 1b

To a suspension of 5-(4-cyclopropyl-1H-imidazol-1-yl)-2-fluoro-4-methylbenzoic acid (89 mg, 0.343 mmol) in DCM (0.6 ml) was added 1-chloro-N,N,2-trimethylprop-1-en-1-amine (Ghosez's reagent, 0.14 mL, 1.02 mmol). The reaction mixture was stirred at room temperature for one hour to form a clear solution and then concentrated in vacuo. The residue (compound 8b) was taken into pyridine (0.6 mL) and cooled down to 0° C., and a solution of 6-(5-isopropyl-1H-tetrazol-1-yl)pyridin-2-amine (1) (50 mg, 0.245 mmol) in DCM (0.6 mL) was added. The reaction mixture was allowed to warm up to room temperature and stirred for 4 hrs. The mixture was concentrated, and then diluted with EtOAc and brine. The aqueous layer was extracted with EtOAc. The combined organic layers were dried over Na$_2$SO$_4$ and concentrated. The residue was purified by chromatography on silica gel using 0→5% MeOH in DCM to give compound of Example 1b as white solid (94 mg, 86% yield). LC-MS (m/zM+1=447.19, calcd. 447.20. $^1$H NMR (400 MHz, DMSO-d$_6$) δ 11.18 (s, 1H), 8.34 (d, J=7.7 Hz, 1H), 8.23 (t, J=8.1 Hz, 1H), 7.72 (d, J=7.8 Hz, 1H), 7.70 (d, J=1.4 Hz, 1H), 7.65 (d, J=6.6 Hz, 1H), 7.48 (d, J=10.9 Hz, 1H), 7.18 (d, J=1.4 Hz, 1H), 3.91 (p, J=6.8 Hz, 1H), 2.25 (s, 3H), 1.89-1.82 (m, 1H), 1.31 (s, 3H), 1.30 (s, 3H), 0.83-0.77 (m, 2H), 0.72-0.67 (m, 2H).

Examples 2b-6b were prepared following the similar methods as Example 1b.

| Example | Structure | LC-MS [M + H]$^+$ unless otherwise noted | H-NMR |
|---|---|---|---|
| 2b | ![structure] | 475 | $^1$H NMR (400 MHz, Chloroform-d) δ 9.11 (d, J = 15.8 Hz, 1H), 8.51 (d, J = 8.3 Hz, 1H), 8.16 (d, J = 7.1 Hz, 1H), 8.08 (t, J = 8.1 Hz, 1H), 7.75 (d, J = 7.8 Hz, 1H), 7.68 (s, 1H), 7.47-7.42 (m, 1H), 7.32 (d, J = 12.2 Hz, 1H), 3.87 (m, J = 6.9 Hz, 1H), 2.33 (s, 3H), 1.53 (d, J = 6.9 Hz, 6H). |

| Example | Structure | LC-MS [M + H]+ unless otherwise noted | H-NMR |
|---|---|---|---|
| 3b | 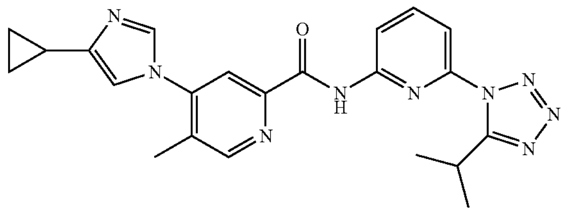 [SMILES: Cc1cnc(C(=O)Nc2cccc(-n3nnnc3C(C)C)n2)cc1-n1cnc(C2CC2)c1] | 430 | ¹H NMR (400 MHz, Chloroform-d) δ 10.44 (s, 1H), 8.68 (s, 1H), 8.59 (d, J = 8.3 Hz, 1H), 8.19 (s, 1H), 8.08 (t, J = 8.0 Hz, 1H), 7.71 (d, J = 8.0 Hz, 1H), 7.65 (s, 1H), 6.98 (s, 1H), 3.96 (m, 1H), 2.49 (s, 3H), 1.96 (m, 1H), 1.53 (d, J = 6.9 Hz, 6H), 0.95 (m, 2H), 0.90 (m, 2H). |
| 4b | 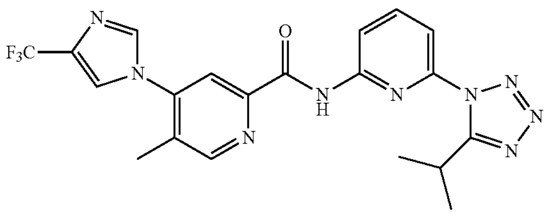 [SMILES: Cc1cnc(C(=O)Nc2cccc(-n3nnnc3C(C)C)n2)cc1-n1cnc(C(F)(F)F)c1] | 458 | ¹H NMR (400 MHz, Chloroform-d) δ 10.40 (s, 1H), 8.78 (s, 1H), 8.59 (d, J = 8.3 Hz, 1H), 8.25 (s, 1H), 8.09 (t, J = 8.1 Hz, 1H), 7.83 (s, 1H), 7.73 (d, J = 7.8 Hz, 1H), 7.58 (s, 1H), 3.96 (m, 1H), 2.49 (s, 3H), 1.54 (d, J = 6.9 Hz, 6H). |
| 5b | 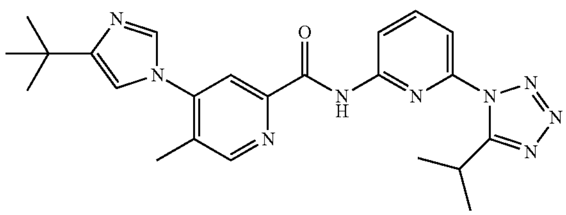 [SMILES: Cc1cnc(C(=O)Nc2cccc(-n3nnnc3C(C)C)n2)cc1-n1cnc(C(C)(C)C)c1] | 446 | ¹H NMR (400 MHz, Chloroform-d) δ 10.45 (s, 1H), 8.69 (s, 1H), 8.59 (d, J = 8.2 Hz, 1H), 8.21 (s, 1H), 8.08 (t, J = 8.1 Hz, 1H), 7.76-7.68 (m, 2H), 6.95 (s, 1H), 3.97 (m, 1H), 2.51 (s, 3H), 1.53 (d, J = 6.9 Hz, 6H), 1.39 (s, 9H). |
| 6b | 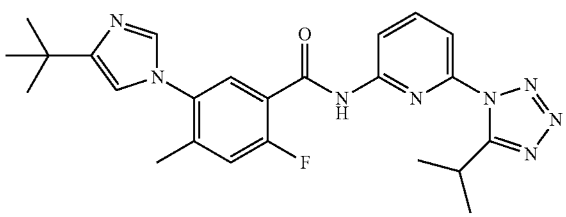 [SMILES: Cc1cc(F)c(C(=O)Nc2cccc(-n3nnnc3C(C)C)n2)cc1-n1cnc(C(C)(C)C)c1] | 463 | ¹H NMR (400 MHz, Chloroform-d) δ 9.12 (d, J = 16.1 Hz, 1H), 8.52 (d, J = 8.2 Hz, 1H), 8.13 (d, J = 7.3 Hz, 1H), 8.07 (t, J = 8.1 Hz, 1H), 7.75 (d, J = 7.8 Hz, 1H), 7.58 (s, 1H), 7.25 (d, J = 12.4 Hz, 1H), 6.79 (s, 1H), 3.88 (m, 1H), 2.33 (s, 3H), 1.53 (d, J = 6.9 Hz, 6H), 1.38 (s, 9H). |

Example 1c

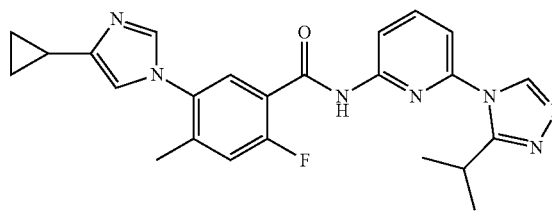

Step 1: Synthesis of 6-(3-isopropyl-4H-1,2,4-triazol-4-yl)pyridin-2-amine (compound 4c)

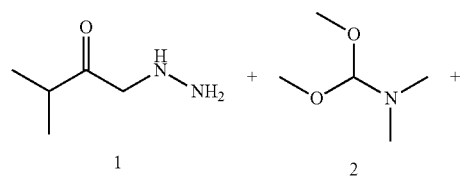

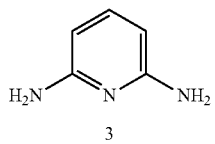

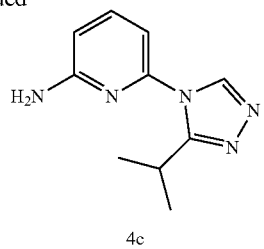

To a suspension of 1-hydrazinyl-3-methylbutan-2-one (673 mg, 5.5 mmol) in acetonitrile (4 ml) was added 1,1-dimethoxy-N,N-dimethylmethanamine (0.731 ml, 5.50 mmol), and the resulting mixture (clear solution) was warmed up to 50° C. and stirred for 30 min. A solution of pyridine-2,6-diamine (612 mg, 5.5 mmol) in acetic acid (5 ml)/acetonitrile (1 ml) was then added and the mixture was heated to 120° C. for 23 h, cooled down to rt, and concentrated. The residue was diluted with EtOAc, washed with sat.NaHCO₃, and concentrated again. The crude product was purified by chromatography on silica gel using DCM/

MeOH (100/0 to 90/10, 10 min) to give the desired product 4. LC-MS [M+H]=204.09, Calcd. 204.12; 1H NMR (400 MHz, DMSO-d$_6$) δ 8.66 (s, 1H), 7.59 (t, J=7.5 Hz, 1H), 6.65 (d, J=7.5 Hz, 1H), 6.53 (d, J=8.3 Hz, 1H), 6.43 (s, 2H), 3.49-3.41 (m, 1H), 1.21 (d, J=6.9 Hz, 6H).

Step 2: Synthesis of 5-(4-cyclopropyl-1H-imidazol-1-yl)-2-fluoro-N-(6-(3-isopropyl-4H-1,2,4-triazol-4-yl)pyridin-2-yl)-4-methylbenzamide

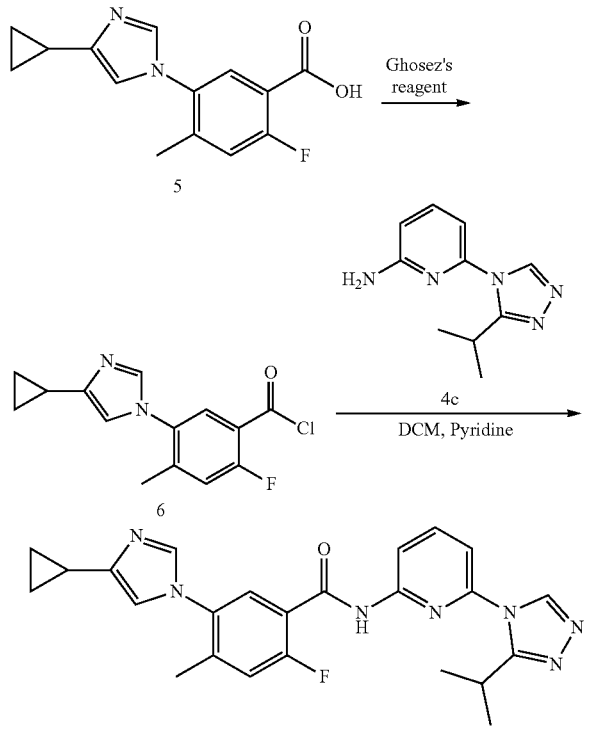

Example 1c

To a suspension of 5-(4-cyclopropyl-1H-imidazol-1-yl)-2-fluoro-4-methylbenzoic acid (5) (30.5 mg, 0.117 mmol) in DCM (1. ml) was added 1-chloro-N,N,2-trimethylprop-1-en-1-amine (Ghosez's reagent, 0.033 ml, 0.251 mmol). The reaction mixture was stirred at rt for 40 min (clear solution) and then concentrated in vacuo. The residue (compound 6) was taken into DCM (1.ml) and cooled down to 0 C, and a solution of 6-(3-isopropyl-4H-1,2,4-triazol-4-yl)pyridin-2-amine (4c) ((17 mg, 0.084 mmol) and pyridine (0.041 ml, 0.502 mmol) in DCM (1 ml) was added. The reaction mixture was allowed to warm up to rt and stirred overnight, and then concentrated. The residue was purified by chromatography on silica gel using DCM/MeOH (100/0 to 70/30, 15 min) to give a desired product (Example 1c) as a white solid. LC-MS [M–H]=444.20, calcd. 444.20. H NMR (400 MHz, DMSO-d$_6$) δ 11.24 (s, 1H), 9.33 (d, J=1.7 Hz, 1H), 8.92 (s, 1H), 8.27 (d, J=8.2 Hz, 1H), 8.17 (t, J=8.0 Hz, 1H), 7.94 (d, J=8.0 Hz, 1H), 7.77 (d, J=1.6 Hz, 1H), 7.59 (d, J=10.7 Hz, 1H), 7.52 (d, J=7.7 Hz, 1H), 3.61-3.41 (m, 1H), 2.29 (s, 3H), 2.10-2.01 (m, 1H), 1.21 (d, J=6.9 Hz, 6H), 1.05 (dt, J=8.6, 3.3 Hz, 2H), 0.92-0.83 (m, 2H).

Example 2c: N-(6-(4H-1,2,4-triazol-4-yl)pyridin-2-yl)-5-(4-cyclopropyl-1H-imidazol-1-yl)-2-fluoro-4-methylbenzamide

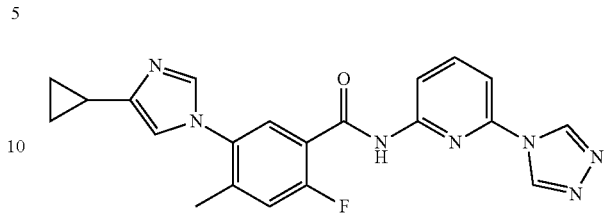

Example 2c was prepared by using similar procedure as described for compound of Example 1c. LC-MS [M–H]= 444.20, calcd. 444.20. $^1$H NMR (400 MHz, DMSO-d$_6$) δ 11.22 (s, 1H), 9.32 (d, J=1.6 Hz, 1H), 9.23 (s, 2H), 8.22-8.10 (m, 2H), 7.93 (d, J=6.4 Hz 1H), 7.79 (d, J=1.6 Hz, 1H), 7.67 (dd, J=7.2, 1.3 Hz, 1H), 7.60 (d, J=10.8 Hz, 1H), 2.30 (s, 3H), 2.08-2.02 (m, 1H), 1.11-0.99 (m, 2H), 0.92-0.83 (m, 2H).

Example 3c

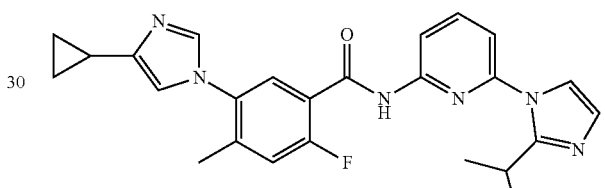

Step 1: Synthesis of 6-(2-isopropyl-1H-imidazol-1-yl)pyridin-2-amine (compound 7c)

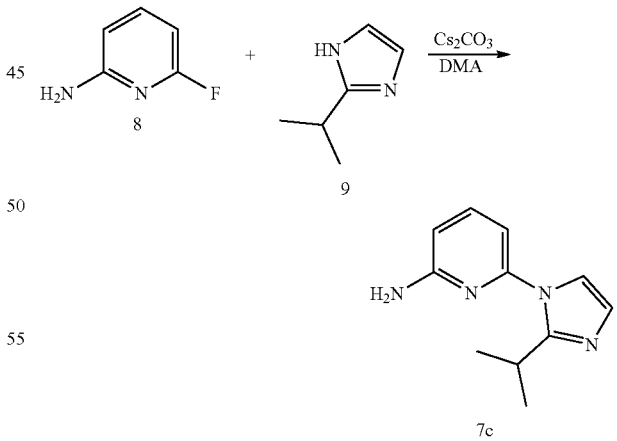

A mixture of 6-fluoropyridin-2-amine (448 mg, 4.00 mmol), 2-isopropyl-1H-imidazole (880 mg, 7.99 mmol) and cesium carbonate (3906 mg, 11.99 mmol) in DMA (4 ml) was heated to 120° C. under N$_2$ and stirred overnight, cooled down to rt, diluted with water, and extracted with EtOAc. The combine organic layers were washed with brine and concentrated. The residue was purified by chromatography on silica gel using hexane/acetone (100/0 to 50/50, 10 min) to give the desired product (7c) as an off-white solid, which was washed with EtOAc to remove some remaining SM. ¹H NMR (500 MHz, DMSO-$d_6$) δ 7.54 (t, J=7.8 Hz, 1H), 7.25 (d, J=1.3 Hz, 1H), 6.85 (d, J=1.3 Hz, 1H), 6.53 (d, J=7.4 Hz, 1H), 6.46 (d, J=8.2 Hz, 1H), 6.28 (s, 2H), 3.44 (h, J=6.8 Hz, 1H), 1.16 (d, J=6.8 Hz, 6H).

Step 2: Synthesis of 5-(4-cyclopropyl-1H-imidazol-1-yl)-2-fluoro-N-(6-(2-isopropyl-1H-imidazol-1-yl)pyridin-2-yl)-4-methylbenzamide (Example 3c)

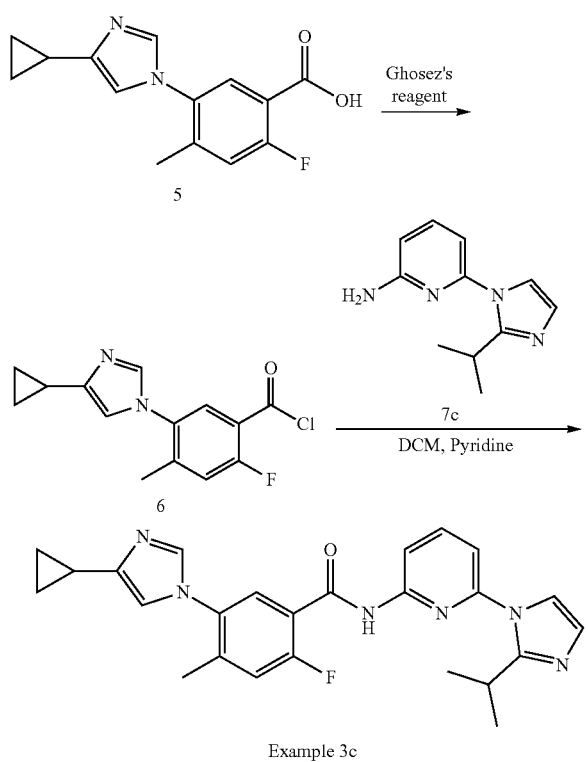

To a suspension of 5-(4-cyclopropyl-1H-imidazol-1-yl)-2-fluoro-4-methylbenzoic acid (5) (64.9 mg, 0.249 mmol) in DCM (2 ml) was added 1-chloro-N,N,2-trimethylprop-1-en-1-amine (0.071 ml, 0.534 mmol). The reaction mixture was stirred at rt for 40 min (clear solution) and then cooled down to 0 C, and a solution of 6-(2-isopropyl-H-imidazol-1-yl)pyridin-2-amine (36 mg, 0.178 mmol) and pyridine (0.086 ml, 1.068 mmol) in DCM (2 ml) was added. The reaction mixture was allowed to warm up to rt and stirred overnight, and then diluted with EtOAc, washed with sat.NaHCO₃, and concentrated. The residue was purified by chromatography on silica gel using hexane/acetone (100/0 to 20/80, 15 min) to give example 3 as a white solid. LC-MS [M+H]=445.20, calcd. 445.21. ¹H NMR (400 MHz, DMSO-$d_6$) δ 11.03 (s, 1H), 8.21 (d, J=8.1 Hz, 1H), 8.08 (t, J=8.0 Hz, 1H), 7.72-7.60 (m, 2H), 7.49-7.39 (m, 2H), 7.37-7.30 (m, 2H), 7.18 (d, J=1.4 Hz, 1H), 6.92 (d, J=1.5 Hz, 1H), 3.52 (p, J=6.8 Hz, 1H), 2.24 (s, 3H), 1.84 (td, J=8.5, 4.3 Hz, 1H), 1.15 (d, J=6.8 Hz, 6H), 0.85-0.74 (m, 2H), 0.74-0.65 (m, 2H).

Example 4c

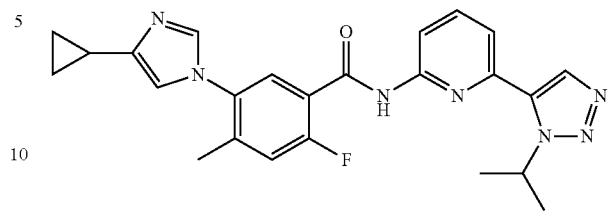

Step 1: Synthesis of 6-(1-isopropyl-1H-1,2,3-triazol-5-yl)pyridin-2-amine (compound 12c)

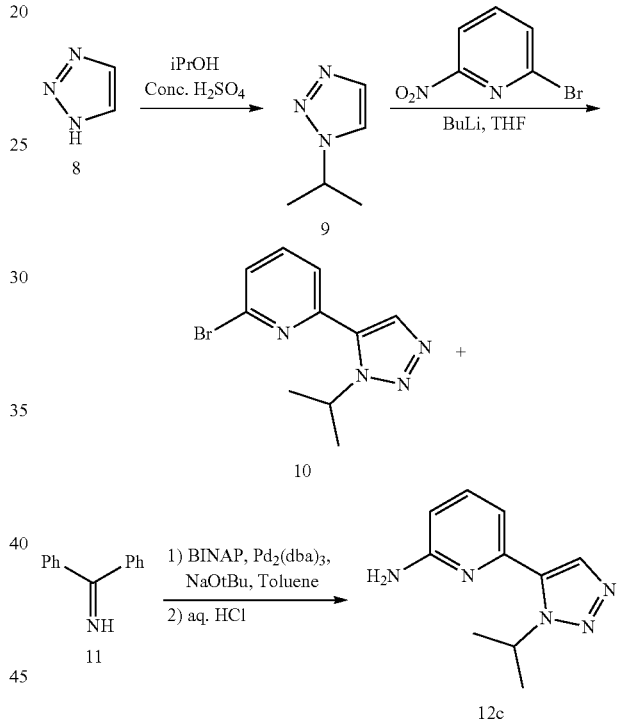

To a flask containing 1H-1,2,3-triazole (3.06 g, 44.3 mmol) and i-PrOH (3.7 ml, 48.7 mmol) at 0° C., was added 96% H₂SO₄ (16.11 ml) dropwise and stirred at 0° C. for 5 h and at rt ° C. for 43 h. The reaction mixture was poured onto ice (100 g). The mixture was extracted with DCM (3×50 mL). To the aqueous layer was added Na₂CO₃ (32 g) slowly (exothermal, bubbling) with stirring. The resulted milky mixture was extracted by DCM (50 ml×3), The combined DCM layers was washed by water (50 ml), then brine (50 ml). Dried, filtered, and concentrated to give compound 9 (2.8 g) as a colorless oil. 1H NMR (400 MHz, Chloroform-d) δ 7.67 (d, J=0.8 Hz, 1H), 7.53 (d, J=0.8 Hz, 1H), 4.85 (m, J=6.8 Hz, 1H), 1.57 (d, J=6.8 Hz, 6H).

At −78° C., n-butyllithium in Hexanes (1.6M) (315 μl, 0.504 mmol) was added to a solution of above 1-isopropyl-1H-1,2,3-triazole (56 mg, 0.504 mmol) in THF (0.97 ml). After stirring at −78° C. for 30 min, a solution of 2-bromo-6-nitropyridine (123 mg, 0.605 mmol) in THF (0.97 ml) was added dropwise. The mixture was stirred at −78 C to rt overnight and then diluted with H₂O and then extracted with ethyl acetate (20 ml×2). The combined organic layers were washed with brine and dried with Na₂SO₄. Evaporation and purification by column chromatography afforded desired product of compound 10 (13 mg). LCMS: 267.0 (M+1); 269.0 (M+1); 1H NMR (400 MHz, Chloroform-d) δ 7.95 (s, 1H), 7.64 (t, J=8.0 Hz, 1H), 7.54 (dd, J=8.0, 0.8 Hz, 1H), 7.48 (dd, J=8.0, 0.8 Hz, 1H), 5.54 (m, J=6.8 Hz, 1H), 1.65 (d, J=6.8 Hz, 6H).

To a solution of above 2-bromo-6-(1-isopropyl-1H-1,2,3-triazol-5-yl)pyridine (12 mg, 0.045 mmol), Pd$_2$(dba)$_3$ (2.057 mg, 2.246 μmol), BINAP (4.20 mg, 6.74 μmol), and sodium tert-butoxide (8.63 mg, 0.090 mmol) in Toluene (0.45 ml) at rt, was added benzophenone imine (9.8 mg, 0.054 mmol) under N₂. The mixture was stirred at 100° C. for 15 hr under N₂. The reaction was quenched with 0.1 N NaOH solution, extracted with EtOAc three times. The combined organic layers were washed by brine, dry over sodium sulfate, filtered and concentrate to give a yellow residue (27 mg). The residue was dissolved in THF (2 ml). Added 6N HCl solution (0.25 ml). The mixture was stirred for 1 hr at room temperature. Added 0.1N HCl (1 ml) and water (2 ml) solution. The mixture was extracted with EtOAc twice. Kept the aqueous layer, adjusted pH>9 with 1N NaOH solution, extracted with DCM three times. Combined the organic layers, dried over sodium sulfate, filter and concentrate to give a crude residue (11 mg). The crude residue was purified by column chromatography to give the compound 12c (6 mg) as white solid. LCMS: 204.09 (M+1); 1H NMR (400 MHz, Chloroform-d) δ 7.87 (s, 1H), 7.55 (t, J=8.0 Hz, 1H), 6.88 (d, J=8.0 Hz, 1H), 6.58 (d, J=8.0 Hz, 1H), 5.49-5.39 (m, 1H), 4.99 (s, 2H), 1.62 (d, J=6.8 Hz, 6H).

Step 2: Synthesis of 5-(4-cyclopropyl-1H-imidazol-1-yl)-2-fluoro-N-(6-(1-isopropyl-1H-1,2,3-triazol-5-yl)pyridin-2-yl)-4-methylbenzamide. (Example 4c)

Example 4c was prepared by using similar procedure as described for compound of Example 1c. LCMS: 446.20 (M+1); 1H NMR (400 MHz, Chloroform-d) δ 9.09 (d, J=15.2 Hz, 1H), 8.35 (dd, J=8.0, 0.8 Hz, 1H), 8.06 (d, J=7.2 Hz, 1H), 7.92 (s, 1H), 7.87 (t, J=8.0 Hz, 1H), 7.54 (s, 1H), 7.37 (dd, J=8.0, 0.8 Hz, 1H), 7.20 (d, J=12.0 Hz, 1H), 6.78 (d, J=1.2 Hz, 1H), 5.44 (m, J=6.8 Hz, 1H), 2.28 (s, 3H), 1.96-1.79 (m, 1H), 1.67 (d, J=6.8 Hz, 6H), 0.95-0.87 (m, 2H), 0.87-0.79 (m, 2H).

Assays

The ability (IC$_{50}$) of compounds to inhibit ASK1 kinase activity was determined by HTRF® KinEASE™ Assay System.

ASK1 was purchased from Thermofisher (Catalogue #PV4011), ATP was purchased from Sigma (Catalogue #A7699), HTRF® KinEASE™ Assay System was obtained from Cisbio (Bedford, Mass.). ½ Area plate was purchased from Perkin Elmer (Catalogue ##6005560). HTRF® KinEASE™-STK is a generic method for measuring serine/threonine kinase activities using a time-resolved fluorescence resonance energy transfer (TR-FRET) immunoassay. The IC$_{50}$ value for each compound was determined in the presence of compound (various concentration from 0 to 10 μM) and a fixed amount of ATP and peptide substrates. The test compound, 1 uM STK3 peptide substrate, and 5 nM of ASK1 kinase are incubated with kinase reaction buffer containing 50 mM HEPES pH 7.5, 0.01% BRIJ-35, 10 mM MgCl2, and 1 mM EGTA for 30 minutes. 100 uM ATP is added to start kinase reaction and incubated for 3 hours. The STK3-antibody labeled with Eu$^{3+}$-Cryptate and 125 nM streptavidin-XL665 are mixed in a single addition with stop reagents provided by the Cisbio kit used to stop the kinase reaction. Fluorescence is detected using an Envision Multilabeled 2014 reader from PerkinElmer. The Fluorescence is measured at 615 nm (Cryptate) and 665 nm (XL665) and a ratio of 665 nm/615 nm is calculated for each well. The resulting TR-FRET is proportional to the phosphorylation level. Staurosporine was used as the positive control. IC$_{50}$ was determined by XLfit 5.3.

By using above method, the inhibition of ASK1 was tested for the compound of formula (I). IC$_{50}$ ranges are as follows: A<1 nM; 1 nM B<10 nM; 10 nM<C<100 nM; 100 nM<D<1 μM; E>μM.

TABLE 5

| Example No. | IC50 |
|---|---|
| 1a | B |
| 2a | B |
| 3a | B |
| 4a | B |
| 5a | B |
| 6a | D |
| 7a | B |
| 8a | B |
| 9a | C |
| 10a | B |
| 11a | B |
| 12a | B |
| 13a | B |
| 14a | B |
| 15a | B |
| 16a | C |
| 17a | B |
| 18a | B |
| 19a | D |
| 20a | C |
| 21a | B |
| 22a | B |
| 23a | B |
| 24a | C |
| 25a | E |
| 26a | A |
| 27a | C |
| 28a | B |
| 29a | B |
| 30a | B |
| 31a | B |
| 32a | B |
| 33a | B |
| 34a | C |
| 35a | C |
| 36a | E |
| 37a | B |
| 38a | B |
| 39a | B |
| 40a | C |
| 41a | C |
| 42a | B |
| 43a | B |
| 44a | B |
| 45a | B |
| 46a | B |
| 47a | B |
| 48a | C |
| 49a | B |
| 50a | B |
| 51a | B |
| 52a | B |
| 53a | B |
| 54a | B |
| 55a | B |
| 56a | B |
| 57a | B |
| 58a | B |
| 59a | B |
| 60a | B |

TABLE 5-continued

| Example No. | IC50 |
|---|---|
| 61a | B |
| 1b | B |
| 2b | D |
| 3b | B |
| 4b | C |
| 5b | B |
| 6b | B |
| 1c | E |
| 2c | E |
| 3c | E |
| 4c | C |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by Formula (I) or a pharmaceutically acceptable salt or ester thereof:

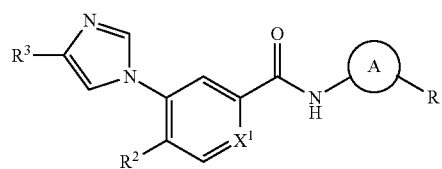

wherein;

A

is selected from

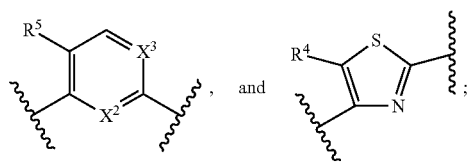

$X^1$, $X^2$ and $X^3$ are each independently selected from N or $C(R^5)$;

$R^3$, $R^4$ and $R^5$ are each independently selected from the group consisting of:
1) Hydrogen;
2) Halogen;
3) —$NO_2$;
4) Cyano;
5) Optionally substituted —$C_1$-$C_8$ alkyl;
6) Optionally substituted —$C_3$-$C_8$ cycloalkyl;
7) Optionally substituted 3- to 8-membered heterocycloalkyl; and
8) Optionally substituted —$C_1$-$C_8$ alkoxyl;

R is selected from the group consisting of

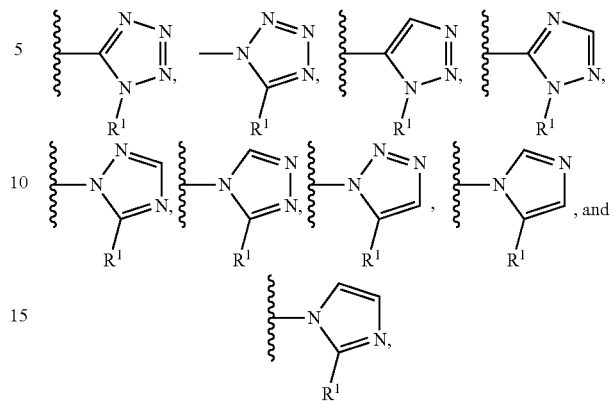

$R^1$ is

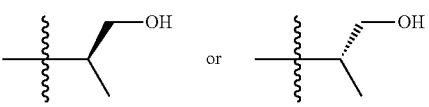

$R^2$ is selected from the group consisting of:
1) Hydrogen;
2) Halogen;
3) —$NO_2$;
4) Cyano;
5) Optionally substituted —$C_1$-$C_8$ alkyl;
6) Optionally substituted —$C_2$-$C_8$ alkenyl;
7) Optionally substituted —$C_2$-$C_8$ alkynyl;
8) Optionally substituted —$C_3$-$C_8$ cycloalkyl;
9) Optionally substituted aryl;
10) Optionally substituted arylalkyl;
11) Optionally substituted 3- to 8-membered heterocycloalkyl;
12) Optionally substituted heteroaryl;
13) Optionally substituted heteroarylalkyl;
14) —$N(R^6)(R^7)$;
15) —$S(O)_2N(R^6)(R^7)$;
16) —$N(R^6)C(O)(R^7)$; and
17) —$N(R^6)S(O)_2(R^7)$;
wherein $R^6$ and $R^7$ are independently selected from the group consisting of hydrogen, —$C_1$-$C_{15}$ alkyl; cycloalkyl, heterocycloalkyl, aryl, and heteroaryl, wherein each alkyl, cycloalkyl, heterocycloalkyl, aryl and heteroaryl is optionally substituted with 1-3 substituents independently selected from halo, alkyl, alkylamino, dialkylamino, alkylC(O)NH—, arylC(O)NH—, heteroarylC(O)NH—, —CN, alkoxy, —$CF_3$, aryl, and heteroaryl, alternatively, $R^7$ and $R^6$ are taken together with the nitrogen atom to which they are attached to form a heterocyclic.

2. The compound of claim 1, wherein $R^1$ is

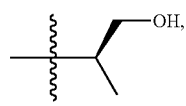

3. The compound of claim 1, wherein $R^2$ is selected from the following:

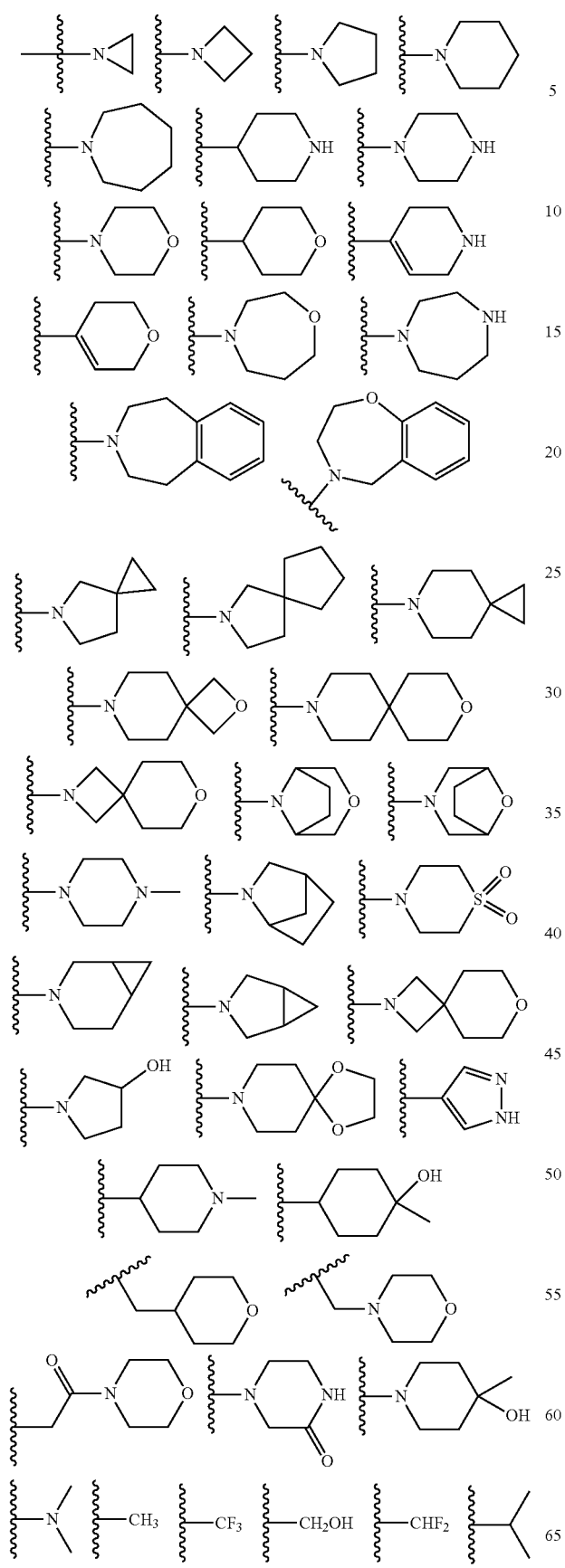
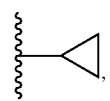
4. The compound of claim 1, wherein R³ is selected from the following:
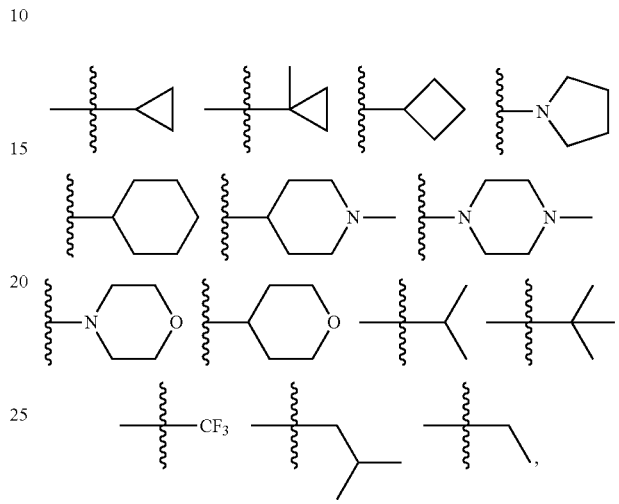
wherein each group is optionally substituted.
5. The compound of claim 1, which is represented by Formula (Ia), (Ib), (Ic), or (Id), or a pharmaceutically acceptable salt or ester thereof:
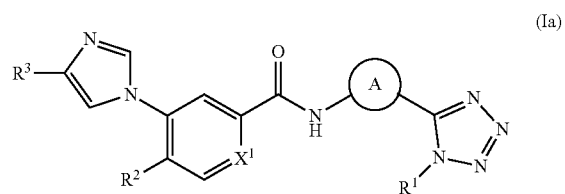
(Ia)
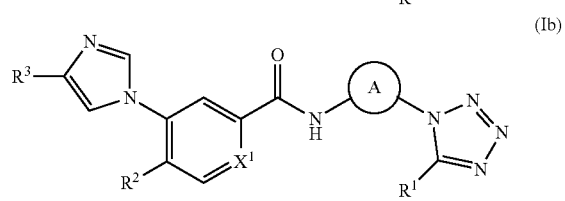
(Ib)
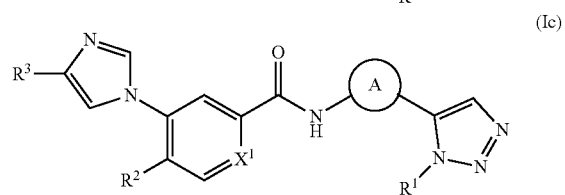
(Ic)
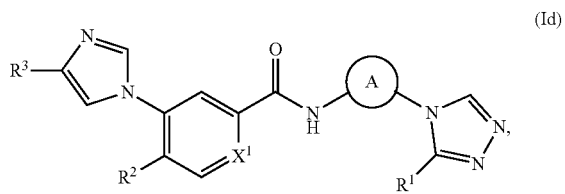
(Id)

wherein

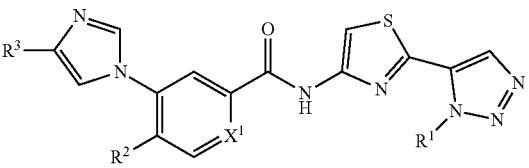

$R^1$, $R^2$, $R^3$ and $X^1$ are as defined claim 1.

6. The compound of claim 1, which is represented by one of Formulae (IIa-1) to (IIa-4) or (IIb-1) to (IIb-4), or a pharmaceutically acceptable salt or ester thereof:

(IIa-1)
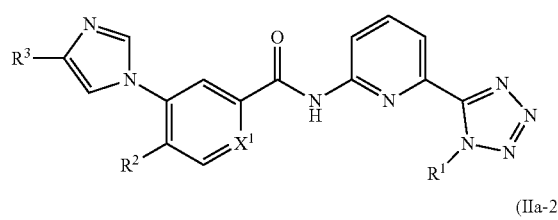

(IIa-2)
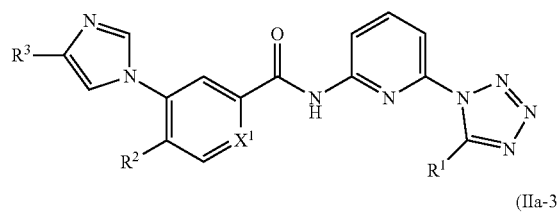

(IIa-3)
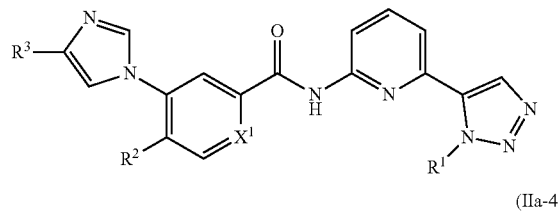

(IIa-4)
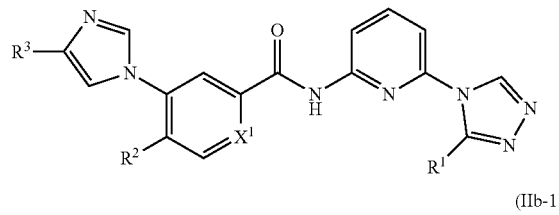

(IIb-1)
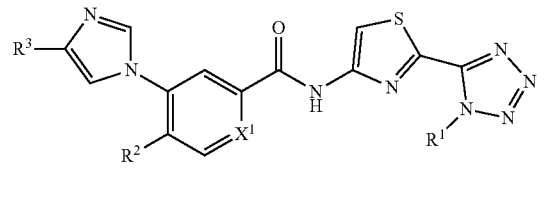

(IIb-2)
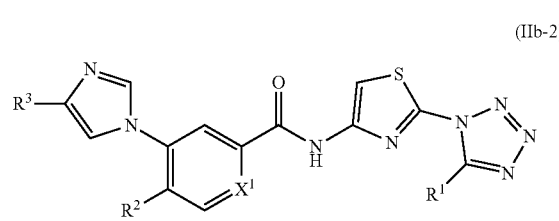

(IIb-3)
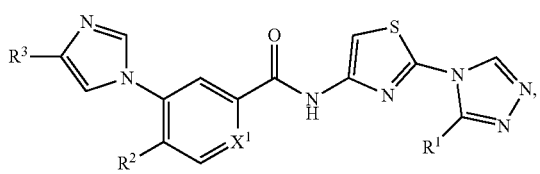

(IIb-4)
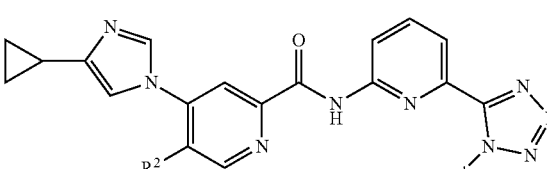

wherein $R^1$, $R^2$, $R^3$, and $X^1$ are as defined claim 1.

7. The compound of claim 1, which is selected from compounds of Formula (IVa-1), (IVa-2), (IVa-3), or (IVa-4), or a pharmaceutically acceptable salt or ester thereof:

(IVa-1)
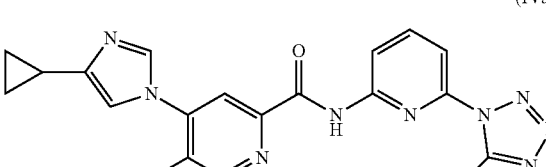

(IVa-2)
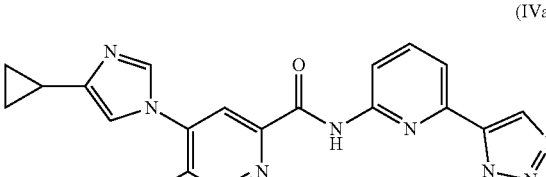

(IVa-3)

(IVa-4)

wherein $R^2$ is selected from $CH_3$, $CF_3$, dimethylamino,

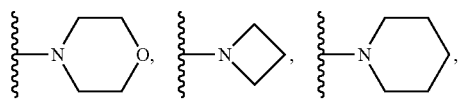

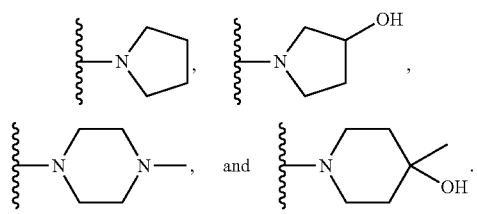

8. The compound of claim 1, which is selected from compounds of Formula (IVb-1), (IVb-2), (IVb-3), or (IVb-4), or a pharmaceutically acceptable salt or ester thereof:

(IVb-1)

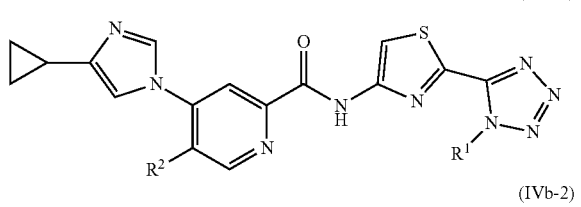

(IVb-2)

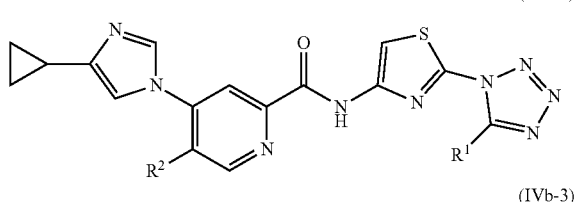

(IVb-3)

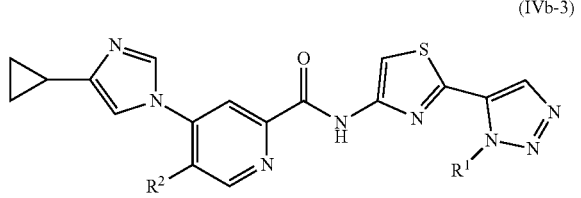

(IVb-4)

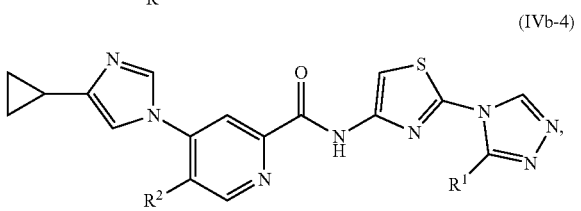

wherein $R^2$ is selected from $CH_3$, $CF_3$, dimethylamino,

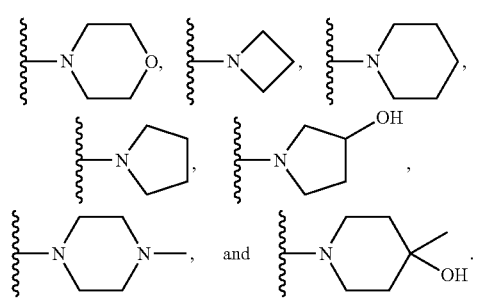

9. The compound of claim 1, which is selected from compounds of Formula (Va-1), (Va-2), (Va-3), or (Va-4), or a pharmaceutically acceptable salt or ester thereof:

(Va-1)

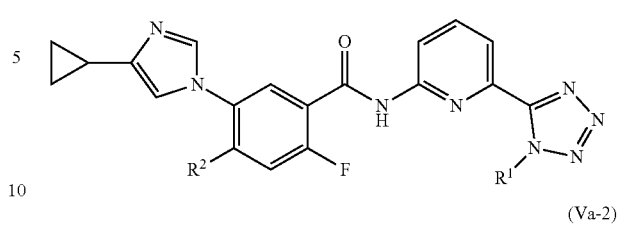

(Va-2)

(Va-3)

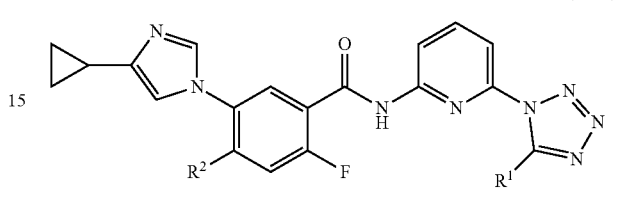

(Va-4)

wherein $R^2$ is selected from $CH_3$, $CF_3$, dimethylamino,

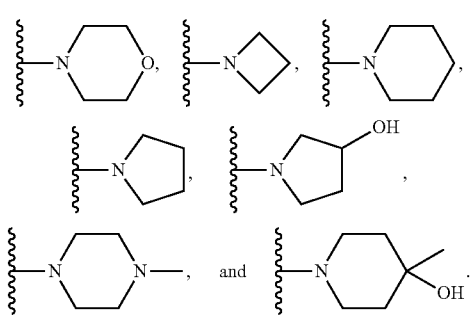

10. The compound of claim 1, which is selected from compounds of Formula (Vb-1), (Vb-2), (Vb-3), or (Vb-4), or a pharmaceutically acceptable salt or ester thereof:

(Vb-1)

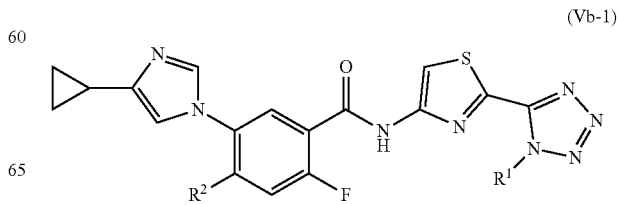

-continued (Vb-2)
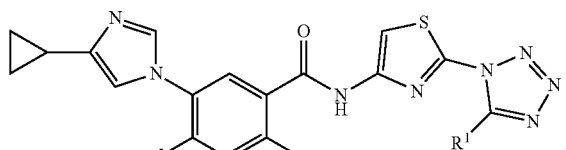

(Vb-3)
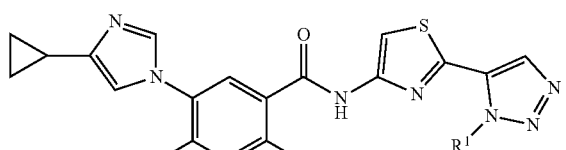

(Vb-4)
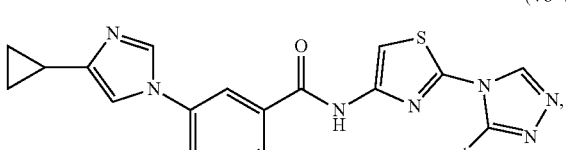

wherein R² is selected from CH₃, CF₃, dimethylamino,

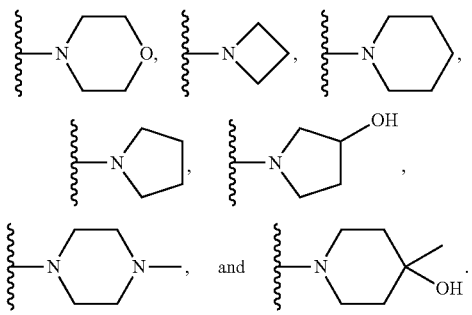

11. The compound of claim 1, which is selected from compounds of Formula (VIa-1), (VIa-2), (VIa-3), or (VIa-4), or a pharmaceutically acceptable salt thereof:

(VIa-1)
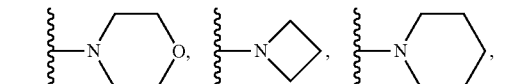

(VIa-2)
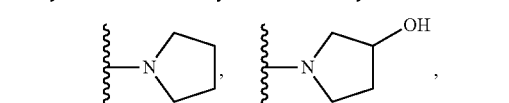

-continued (VIa-3)
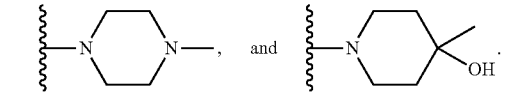

(VIa-4)

wherein R² is selected from CH₃, CF₃, dimethylamino.

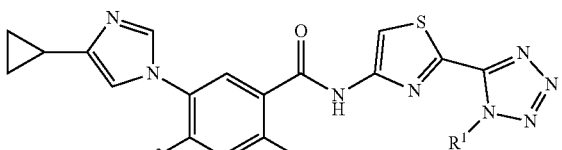

12. The compound of claim 1, which is selected from compounds of Formula (VIb-1), (VIb-2), (VIb-3), or (VIb-4), or a pharmaceutically acceptable salt or ester thereof:

(VIb-1)
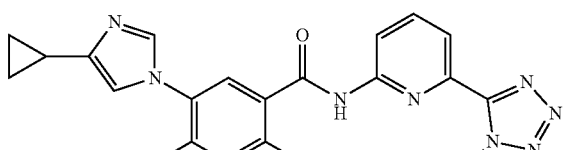

(VIb-2)
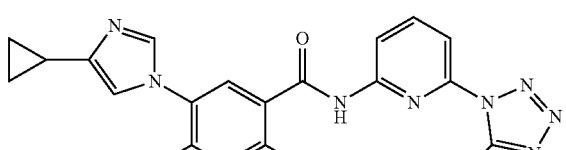

(VIb-3)
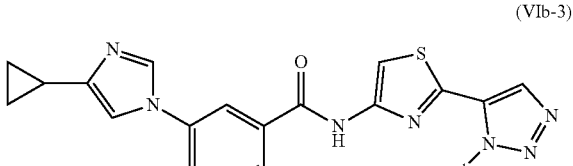

-continued (VIb-4)

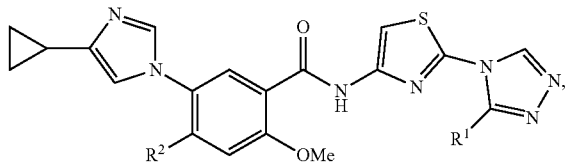

wherein R² is selected from CH₃, CF₃, dimethylamino,

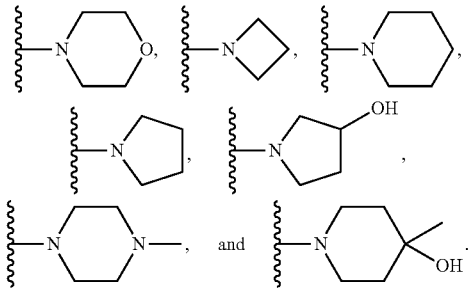

13. A pharmaceutical composition comprising a compound of claim 1 and a pharmaceutically acceptable carrier or excipient.

14. A method for treating an ASK-1 mediated disease or condition in a subject in need thereof, comprising administering to the subject a therapeutically effective amount of one or more compounds of Formula (I) according to claim 1.

15. The method according to claim 14, wherein the ASK-1 mediated disease or condition is selected from the group consisting of an autoimmune disorder, a neurodegenerative disorder, an inflammatory disease, chronic kidney disease, renal disease, cardiovascular disease, a metabolic disease, or an acute or chronic liver disease.

16. The method according to claim 15, wherein the ASK-1 mediated disease or condition is a chronic liver disease selected from the group consisting of primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, or alpha 1-antitrypsin deficiency.

17. The method according to claim 15, wherein the ASK-1 mediated disease or condition is a renal disease selected from the group consisting of diabetic nephropathy, focal segmental glomerulosclerosis (FSGS), hypertensive nephrosclerosis, chronic glomerulonephritis, chronic transplant glomerulopathy, chronic interstitial nephritis, kidney fibrosis and polycystic kidney disease.

18. The method according to claim 15, wherein the ASK-1 mediated disease or condition is a cardiovascular disease selected from the group consisting of atherosclerosis, arteriosclerosis, reperfusion/ischemia in stroke, cardiac hypertrophy, respiratory diseases, heart attacks, and myocardial ischemia or a metabolic disease selected from the group consisting of insulin resistance, Type I and Type II diabetes, and obesity.

19. The method according to claim 15, wherein the ASK-1 mediated disease or condition is a chronic kidney disease selected from the group consisting of polycystic kidney disease, pyelonephritis, kidney fibrosis and glomerulonephritis.

20. The compound of claim 1, selected from the compounds set forth below or a pharmaceutically acceptable salt or ester thereof:

| Compound | Structure |
|---|---|
| 5a | 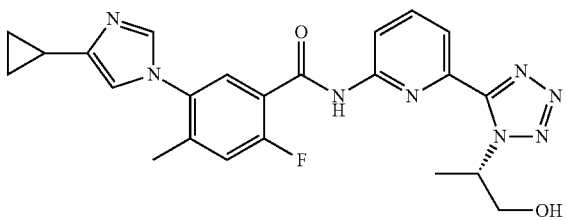 [SMILES: Cc1cc(F)c(C(=O)Nc2cccc(-c3nnnn3[C@@H](C)CO)n2)cc1-n1cnc(C2CC2)c1] |
| 6a | 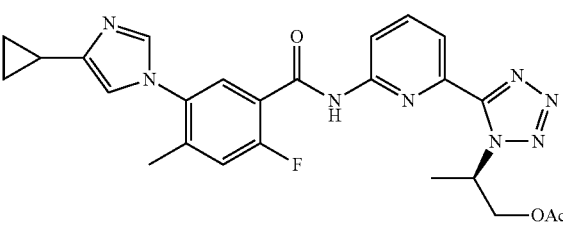 [SMILES: CC(=O)OC[C@@H](C)n1nnnc1-c1cccc(NC(=O)c2cc(-n3cnc(C4CC4)c3)c(C)cc2F)n1] |

-continued

| Compound | Structure |
|---|---|
| 7a | 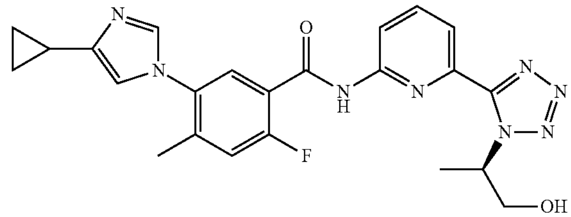 [SMILES: Cc1cc(F)c(C(=O)Nc2cccc(-c3nnnn3[C@H](C)CO)n2)cc1-n1cnc(C2CC2)c1] |
| 24a | 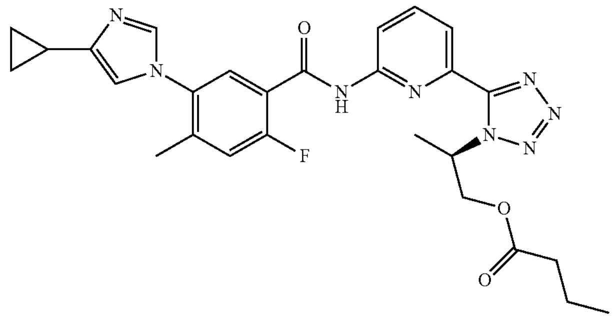 [SMILES: CCCC(=O)OC[C@@H](C)n1nnnc1-c1cccc(NC(=O)c2cc(-n3cnc(C4CC4)c3)c(C)cc2F)n1] |
| 25a | 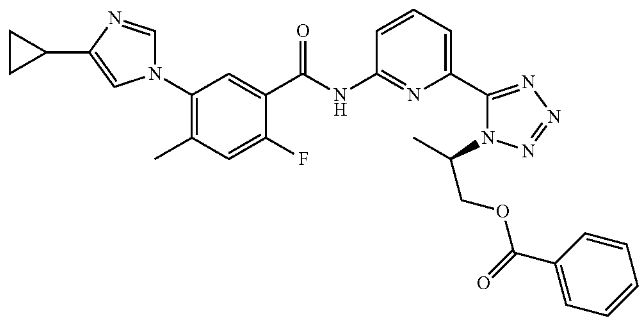 [SMILES: Cc1cc(F)c(C(=O)Nc2cccc(-c3nnnn3[C@H](C)COC(=O)c3ccccc3)n2)cc1-n1cnc(C2CC2)c1] |
| 28a | 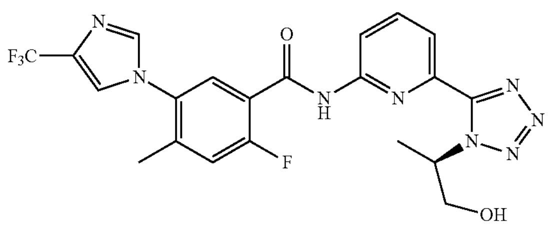 [SMILES: Cc1cc(F)c(C(=O)Nc2cccc(-c3nnnn3[C@H](C)CO)n2)cc1-n1cnc(C(F)(F)F)c1] |
| 30a | 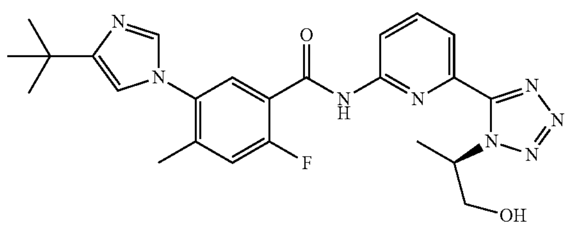 [SMILES: Cc1cc(F)c(C(=O)Nc2cccc(-c3nnnn3[C@H](C)CO)n2)cc1-n1cnc(C(C)(C)C)c1] |
| 32a | 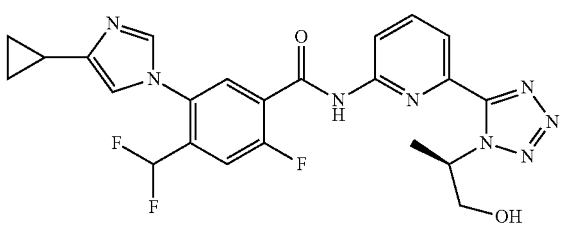 [SMILES: C[C@H](CO)n1nnnc1-c1cccc(NC(=O)c2cc(-n3cnc(C4CC4)c3)c(C(F)F)cc2F)n1] |

-continued
| Compound | Structure |
|---|---|
| 33a | 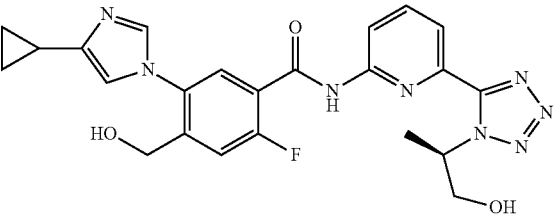 [SMILES: C[C@H](CO)n1nnnc1-c1cccc(NC(=O)c2cc(-n3cnc(C4CC4)c3)c(CO)cc2F)n1] |
| 49a | 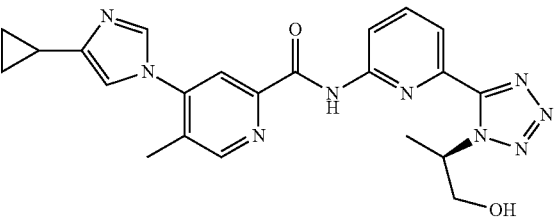 [SMILES: Cc1cnc(C(=O)Nc2cccc(-c3nnnn3[C@H](C)CO)n2)cc1-n1cnc(C2CC2)c1] |
| 51a | 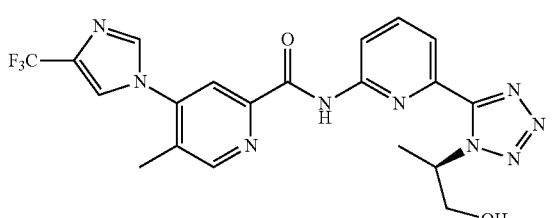 |
| 53a | 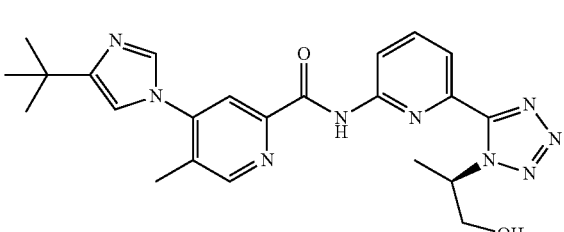 |
| 55a | 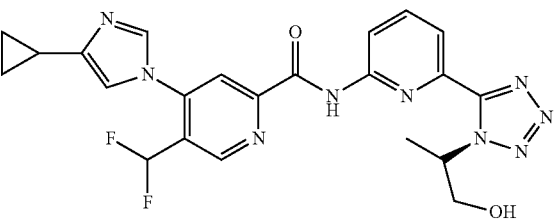 |
| 58a | 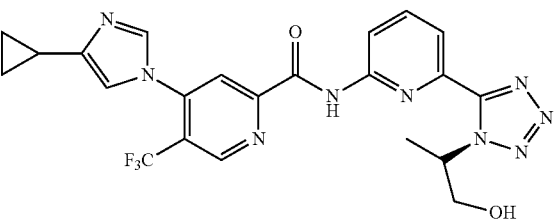 |

-continued
| Compound | Structure |
|---|---|
| 61a | 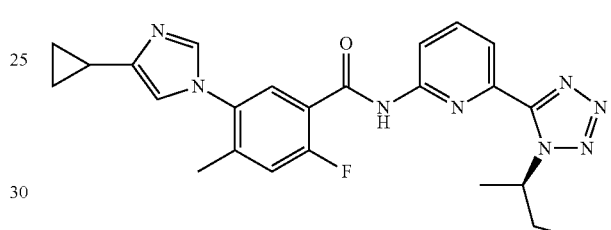 |
21. The compound of claim 20 having the structure
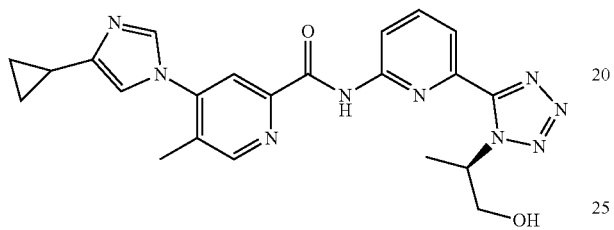
or a pharmaceutically acceptable salt thereof.
22. The compound of claim 20 having the structure
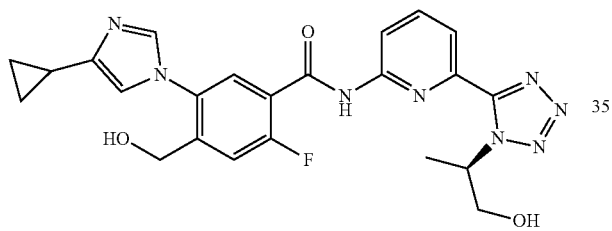
or a pharmaceutically acceptable salt thereof.
23. The compound of claim 20 having the structure
or a pharmaceutically acceptable salt thereof.
* * * * *

UNITED STATES PATENT AND TRADEMARK OFFICE
CERTIFICATE OF CORRECTION

PATENT NO. : 10,988,458 B2  
APPLICATION NO. : 16/866778  
DATED : April 27, 2021  
INVENTOR(S) : Guoqiang Wang et al.

Page 1 of 1

It is certified that error appears in the above-identified patent and that said Letters Patent is hereby corrected as shown below:

In the Claims

At Column 148

In Claim 4, Line 15, delete " 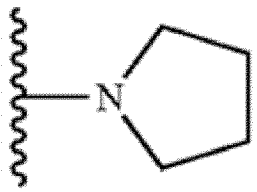 " and insert -- 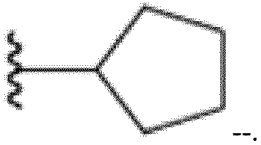 --.

Signed and Sealed this  
First Day of June, 2021

Drew Hirshfeld  
*Performing the Functions and Duties of the  
Under Secretary of Commerce for Intellectual Property and  
Director of the United States Patent and Trademark Office*